United States Patent
Isaacs et al.

(10) Patent No.: US 11,149,280 B2
(45) Date of Patent: Oct. 19, 2021

(54) ENGINEERING ORGANISMS RESISTANT TO VIRUSES AND HORIZONTALLY TRANSFERRED GENETIC ELEMENTS

(71) Applicant: Yale University, New Haven, CT (US)

(72) Inventors: Farren Isaacs, New Haven, CT (US); Natalie Ma, New Haven, CT (US); Jesse Rinehart, West Haven, CT (US); Colin Hemez, New Haven, CT (US)

(73) Assignee: YALE UNIVERSITY, New Haven, CT (US)

(*) Notice: Subject to any disclaimer, the term of this patent is extended or adjusted under 35 U.S.C. 154(b) by 0 days.

(21) Appl. No.: 17/107,555

(22) Filed: Nov. 30, 2020

(65) Prior Publication Data

US 2021/0123064 A1   Apr. 29, 2021

Related U.S. Application Data

(63) Continuation of application No. PCT/US2020/048471, filed on Aug. 28, 2020.

(60) Provisional application No. 62/927,642, filed on Oct. 29, 2019.

(51) Int. Cl.
| | |
|---|---|
| *C12N 15/70* | (2006.01) |
| *C12N 15/09* | (2006.01) |
| *C12N 15/74* | (2006.01) |
| *C12N 15/00* | (2006.01) |
| *C12N 15/63* | (2006.01) |

(52) U.S. Cl.
CPC ............ *C12N 15/70* (2013.01); *C12N 15/09* (2013.01); *C12N 15/74* (2013.01); *C12N 15/00* (2013.01); *C12N 15/63* (2013.01)

(58) Field of Classification Search
CPC ........ C12N 15/70; C12N 9/93; C12N 15/102; C12N 15/1024; C12Y 601/01
See application file for complete search history.

(56) References Cited

U.S. PATENT DOCUMENTS

| | | | |
|---|---|---|---|
| 4,495,280 A | 1/1985 | Bujard | |
| 4,868,111 A | 9/1989 | Bujard | |
| 5,362,646 A | 11/1994 | Bujard | |
| 5,464,758 A | 11/1995 | Gossen | |
| 5,589,362 A | 12/1996 | Bujard | |
| 5,650,298 A | 7/1997 | Bujard | |
| 5,654,168 A | 8/1997 | Bujard | |
| 5,789,156 A | 8/1998 | Bujard | |
| 5,814,618 A | 9/1998 | Bujard | |
| 5,888,981 A | 3/1999 | Bujard | |
| 5,922,927 A | 7/1999 | Bujard | |
| 6,004,941 A | 12/1999 | Bujard | |
| 6,087,166 A | 7/2000 | Baron | |
| 6,136,954 A | 10/2000 | Bujard | |
| 6,242,667 B1 | 6/2001 | Bujard | |
| 6,252,136 B1 | 6/2001 | Bujard | |
| 6,271,341 B1 | 8/2001 | Baron | |
| 6,271,348 B1 | 8/2001 | Bujard | |
| 6,783,756 B2 | 8/2004 | Bujard | |
| 6,852,834 B2 | 2/2005 | Chilkoti | |
| 8,153,432 B2 | 4/2012 | Church | |
| 10,501,734 B2 | 12/2019 | Isaacs | |
| 2003/0148422 A1 | 8/2003 | Doring | |
| 2017/0240908 A1 | 8/2017 | Isaacs | |

FOREIGN PATENT DOCUMENTS

| | | |
|---|---|---|
| WO | 1999058652 | 11/1999 |
| WO | 2002086075 | 10/2002 |
| WO | 2007005053 | 1/2007 |
| WO | 2008036392 | 5/2008 |
| WO | 2009048971 | 4/2009 |
| WO | 2009049223 | 4/2009 |
| WO | 2012087483 | 6/2012 |
| WO | 2013003597 | 1/2013 |
| WO | 2015048364 | 4/2015 |
| WO | 2015120287 | 8/2015 |
| WO | 2016073079 | 5/2016 |

OTHER PUBLICATIONS

Mukai, et al., "Reassignment of a rare sense codon to a non-canonical amino acid in *Escherichia coli*," Nucleic Acids Res., 43:8111 (2015).
Aerni, et al., "Revealing the amino acid composition of proteins within an expanded genetic code", Nucleic Acids Res., 43(2):e8 (2015).
Altenhoefer, et al, "The probiotic *Escherichia coli* strain Nissle 1917 interferes with invasion of human intestinal epithelial cells by different enteroinvasive bacterial pathogens", FEMS Immunol. Med. Microbiol, 40:223-229 (2004).
Ambrogelly & Palioura, "Natural expansion of the genetic code" Nature Chemical Biology, 3:29-35 (2007).
Amiram, et al., "Evolution of translation machinery in recoded bacteria enables multi-site incorporation of nonstandard amino acids," Nature Biotechnology, 33:1272-1279 (2015).
Anderson, et al., "Environmentally controlled invasion of cancer cells by engineered bacteria," J. Mol. Biol., 355:619-27 (2006).

(Continued)

*Primary Examiner* — Iqbal H Chowdhury
(74) *Attorney, Agent, or Firm* — Pabst Patent Group LLP

(57) ABSTRACT

Organisms resistant to horizontal gene transfer (HGT), and compositions and methods of use thereof are provided. The organisms are typically genomically recoded organisms (GRO), typically cells, having a genome in which at least one endogenous codon has been eliminated by reassignment of the codon to a synonymous or non-synonymous codon. The GRO typically include a recombinant expression construct for expression of at least one element of a ribosomal rescue pathway, typically lacking the eliminated codon. Typically, the disclosed cells are resistant to completed transfer and/or expression of a horizontally transferred genetic element (HTGE) from another organism compared a corresponding cell having a genome wherein the eliminated codon has not been eliminated. In some embodiments, the organism from which the HTGE is being transferred is a bacterium or a virus.

20 Claims, 8 Drawing Sheets
Specification includes a Sequence Listing.

(56) References Cited

OTHER PUBLICATIONS

Atkins and Baranov, "The distinction between recoding and codon reassignment", Genetics, 185:1535-6 (2010).
Atkins, et al., "Ribosomal frameshifting and transcriptional slippage: from genetic steganography and cryptography to adventitious use," Nucleic Acids Research, 243:gkw530 (2016).
Baba, et al, "Construction of *Escherichia coli* K-12 in-frame, single-gene knockout mutants: the Keio collection", Mol. Syst. Biol, 2:2006-8 (2006).
Bain, et al, "Ribosome-mediated incorporation of a non-standard amino acid into a peptide through expansion of the genetic code" Nature, 356:537-9 (1992).
Baltrus, et al., "Exploring the costs of horizontal gene transfer," Trends Ecol. Evol, 28, 489-495 (2013).
Baneyx & Mujacic, "Recombinant protein folding and misfolding in *Escherichia coli*," Biotechnology, 22:1399-1408 (2004).
Baranov, et al., "Augmented genetic decoding: global, local and temporal alterations of decoding processes and codon meaning," Nature Reviews Genetics, 16:517-529 (2015).
Barone, et al., "Viral contamination in biologic manufacture and implications for emerging therapies." Nature Biotechnology, vol. 38, pp. 563-572 (2020).
Bayer and Smolke, "Programmable ligand-controlled riboregulators of eukaryotic gene expression" Nat Biotechnol., 23(3):337-43 2005).
Betenbaugh, et al., "Effects of plasmid amplification and recombinant gene expression on the growth kinetics of recombinant *E. coli*", Biotechnol. Bioeng, 33:1425-36 (1989).
Bethencourt, "Virus stalls Genzyme plant." Nat. Biotechnol, 27, 681 (2009).
Bickle, "Biology of DNA restriction." Microbial Rev, 57:434-450 (1993).
Blank, et al., "An RNA polymerase mutant with reduced accuracy of chain elongation." Biochemistry, 25:5920-5928 (1986).
Boeke, et al., "Genome engineering. The genome project-write." Science, 353:126-127 (2016).
Bonde, et al., "Direct mutagenesis of thousands of genomic targets using microarray-derived oligonucleotides", ACS Synth Biol., 4(1):17-22 (2015).
Brenner, et al, "Engineering microbial consortia: a new frontier in synthetic biology", Trends Biotechnol, 26:483-9 (2008).
Cai, et al., "Intrinsic biocontainment: Multiplex genome safeguards combine transcriptional and recombinational control of essential yeast genes", PNAS, 112(6):1803-8 (2015).
Callura, et al, "Tracking, tuning, and terminating microbial physiology using synthetic riboregulators", PNAS, 107:15898-903 (2010).
Carlson, et al., "Engineered ribosomes with tethered subunits for expanding biological function." Nat Commun, 10(1):3920 (2019). doi: 10.1038/s41467-019-11427-y.
Carr, et al, "Enhanced multiplex genome engineering through co-operative oligonucleotide co-selection", Nucleic Acids Res, 40:e132 (2012).
Chadani, et al., "Ribosome rescue by *Escherichia coli* ArfA (YhdL) in the absence of trans-translation system," Molecular Microbiology, 78:796-808 (2010).
Chadani, et al., "trans-translation-mediated tight regulation of the expression of the alternative ribosome-rescue factor ArfA in *Escherichia coli*," Genes & Genetic Systems, 86:151-163 (2011).
Chin, "Expanding and reprogramming the genetic code of cells and animals", Annu Rev Biochem, 83:379-408 (2014).
Chin, et al., "Addition of p-azido-L-phenylalanine to the genetic code of *Escherichia coli*", J Am Chem Soc, 124:9026-7 (2002).
Chin, et al., "Total synthesis of *Escherichia coli* with a recoded genome." Nature, 569(7757):514-518 (2019). doi: 10.1038/s41586-019-1192-5.
Cohen, et al, "Construction of biologically functional bacterial plasmids in vitro", PNAS., 70:3240-4 (1973).
Coleman, et al., "Virus attenuation by genome-scale changes in codon pair bias," Science, 320:1784-1787 (2008).

Cooley, et al., "Structural basis of improved second-generation 3-nitro-tyrosine tRNA synthetases", Biochemistry, 53(12):1916-24 (2014).
Cruz-Vera, et al., "Nascent polypeptide sequences that influence ribosome function," Current Opinion in Microbiology, 14:160-166 (2011).
Dang, et al., Combination bacteriolytic therapy for the treatment of experimental tumors, Proc. Natl. Acad. Sci. U.S.A., 98, 15155-15160 (2001).
Davies, "Inactivation of antibiotics and the dissemination of resistance genes," Science, 264:375-382 (1994).
Davis and Chin, "Designer proteins: applications of genetic code expansion in cell biology", Nat. Rev. Mol. Cell Biol., 13:168-82 (2012).
Deng, et al., "Delineating the site of interaction on the pill protein of filamentous bacteriophage fd with the F-pilus of *Escherichia coli*." J Mol Biol, 319:603-614 (2002). [PubMed: 12054858].
Devito, "Recombineering with toIC as a selectable/counter-selectable marker: remodeling the rRNA operons of *Escherichia coli* " Nucleic Acids Res., 36:e4 (2008).
Drake, "Rates of spontaneous mutation among RNA viruses." Proc Natl Acad Sci U S A, 90:4171-4175 (1993).
Dumas, et al., "Designing logical codon reassignment—Expanding the chemistry in biology", Chem. Sci., 6:50-69 (2015).
Eggertsson, "Transfer ribonucleic acid-mediated suppression of termination codons in *Escherichia coli*", Microbiol. Rev, 52:354-74 (1988).
Ellis, et al., "High efficiency mutagenesis, repair, and engineering of chromosomal DNA using single-stranded oligonucleotides." Proc. Natl. Acad. Sci. U.S.A., 98:6742-6746 (2001).
Fan, et al, "Exploring the substrate range of wild-type aminoacyl-tRNA synthetases", ChemBioChem, 15:1805-9 (2014).
Frost, et al., "Analysis of the sequence and gene products of the transfer region of the F sex factor." Microbiol Rev, 58:162-210 (1994).
Gallagher, et al, "Rapid editing and evolution of bacterial genomes using libraries of synthetic DNA", Nat. Protoc., 9:2301-16 (2014).
Gallagher, et al,, "Multilayered genetic safeguards limit growth of microorganisms to defined environments", Nucleic Acids Res., 43(3):1945-54 (2015).
Gallagher, et al,, "Multilayered genetic safeguards restricted growth of microorganisms to synthetic environments", poster SB60, presented at conference in London, England, Jul. 9-11 (2013).
Garmory, et al., "The use of live attenuated bacteria as a delivery system for heterologous antigens," J. Drug Target, 11, 471-479 (2003).
Garza-Sanchez, et al., "tmRNA regulates synthesis of the ArfA ribosome rescue factor," Molecular Microbiology, 80:1204-1219 (2011).
Genbank accession CP006698, Synthetic *Escherichia coli* C321. deltaA, complete sequence, 4 pages, first appeared. Oct. 18, 2013, updated Jan. 21, 2015, accessed Aug. 25, 2017.
Genbank accession U00096, *Escherichia coli* str. K-12 substr. MG1655, complete genome, pp. 1-3 only accessed Feb. 5, 2021.
George et al., "Generation of phospho-ubiquitin variants by orthogonal translation reveals codon skipping," FEBS Letters, 590:1530-1542 (2016).
Getino, et al., "Synthetic Fatty Acids Prevent Plasmid-Mediated Horizontal Gene Transfer." MBio. 6:e01032-01015 (2015).
Gingold & Pilpel, "Determinants of translation efficiency and accuracy. Molecular Systems Biology," Molecular Systems Biology 7:481 (2011).
Gogarten & Townsend, "Horizontal gene transfer, genome innovation and evolution," Nature Reviews Microbiology 3:679-687 (2005).
Graille & Seraphin, "Surveillance pathways rescuing eukaryotic ribosomes lost in translation," Nature Reviews Molecular Cell Biology, 13(11):727-35 (2012) doi: 10.1038/nrm3457.
Grayhack, et al., "Phage lambda gene Q antiterminator recognizes RNA polymerase near the promoter and accelerates it through a pause site." Cell, 42:259-269 (1985).
Gregg, et al., "Rational optimization of toIC as a powerful dual selectable marker for genome engineering", Nucleic Acids Res., 42(7):4779-90 (2014).

(56) References Cited

OTHER PUBLICATIONS

Grillot-Courvalin, et al, "Functional gene transfer from intracellular bacteria to mammalian cells", Nat. Biotechnol, 16:862-6 (1998).
Grosskopf & Soyer, "Synthetic microbial communities" Current Opinion in Microbiology, 18:72-77 (2014).
Hafez, et al., "A second eukaryotic group with mitochondrion-encoded tmRNA: in silico identification and experimental confirmation." RNA Biol, 10(7): 1117-1124 (2013).
Hammerling, et al, "Bacteriophages use an expanded genetic code on evolutionary paths to higher fitness", Nature Chem. Biol, 10:178-80 (2014).
Handa et al., "YaeJ is a novel ribosome-associated protein in *Escherichia coli* that can hydrolyze peptidyl-tRNA on stalled ribosomes." Nucleic Acids Research, 39:1739-1748 (2011).
Hayes, et al., "Stop codons preceded by rare arginine codons are efficient determinants of SsrA tagging in *Escherichia coli*" PNAS, 99:3440-3445 (2002).
Heinemann, et al., "Enhanced phosphoserine insertion during *Escherichia coli* protein synthesis via partial UAG codon reassignment and release factor 1 deletion", FEBS Lett, 586:3716-22 (2012).
Hillesland & Stahl, "Rapid evolution of stability and productivity at the origin of a microbial mutualism." PNAS, 107:2124-2129 (2010).
Hsu, et al., "Structure of an *Escherichia coli* tRNA operon containing linked genes for arginine, histidine, leucine, and proline tRNAs." Journal of Bacteriology, 158:934-942 (1984).
Huang, et al., "A persistent untranslated sequence within bacteriophage T4 DNA topoisomerase gene 60." Science, 239:1005-1012 (1988).
Hudson, et al., "Ends of the line for tmRNA-SmpB." Frontiers in Microbiology, 5:421 (2014).
International Search Report in PCT/US2020/048471 dated Oct. 16,2020.
Isaacs, et al, "Precise manipulation of chromosomes in vivo enables genome-wide codon replacement", Science, 333:348-53 (2011).
Isaacs, et al, Engineered riboregulators enable post-transcriptional control of gene expression, Nat. Biotechnol, 22:841-7 (2004).
Ivanova, et al., "Stop codon reassignments in the wild." Science, 344:909-913 (2014).
Jaschke, et al. "A fully decompressed synthetic bacteriophage ØX174 genome assembled and archived in yeast."Virology, 434:278-284 (2012).
Jensen, et al, "Programmed cell death in bacteria: proteic plasmid stabilization systems", Mol. Microbiol., 17:205-210 (1995).
Jensen, et al., "A substrate-dependent biological containment system for Pseudomonas putida based on the *Escherichia coli* gef gene," Appl. Environ. Microbiol., 59,3713-3717 (1993).
Jeong, et al., "Genome-scale genetic engineering in *Escherichia coli*," Biotechnol Adv., 31(6):804-10 (2013). doi: 10.1016/j.biotechadv.2013.04.003. Epub Apr. 24, 2013. PMID: 23624241.
Johnson, et al., "Residue-specific incorporation of non-canonical amino acids into proteins: recent developments and applications.", Curr Opin Chem Biol, 14:774-80 (2010).
Johnson, et al., "RF1 knockout allows ribosomal incorporation of unnatural amino acids at multiple sites", Nat Chem Biol, 7:779-86 (2011) [Supplemental Material].
Johnson, et al., "RF1 knockout allows ribosomal incorporation of unnatural amino acids at multiple sites", Nat Chem Biol, 7:779-86 (2011).
Keiler & Feaga, "Resolving nonstop translation complexes is a matter of life or death."Journal of Bacteriology, 196:2123-2130 (2014).
Keiler and Ramadoss, "Bifunctional transfer-messenger RNA." Biochimie. 93(11): 1993-1997 (2011).
Keiler, "Mechanisms of ribosome rescue in bacteria", Nature Reviews Microbiology, 13:285-297 (2015).
Keiler, et al., "Role of a peptide tagging system in degradation of proteins synthesized from damaged messenger RNA." Science, 271:990-993 (1996).

Kimman, et al., "Evidence-based biosafety: a review of the principles and effectiveness of microbiological containment measures", Clin. Microbiol., 21(3):403-25 (2008).
Kirshenbaum, et al., "Biosynthesis of proteins incorporating a versatile set of phenylalanine analogues", Chembiochem, 3:235-7 (2002).
Knight, et al., "Rewiring the keyboard: evolvability of the genetic code." Nature Reviews Genetics, 2:49-58 (2001).
Knudsen, et. al, "Development of efficient suicide mechanisms for biological containment of bacteria", Appl. Environ. Microbiol, 57:85-92 (1991).
Kong, et al, "Regulated programmed lysis of recombinant *Salmonella* in host tissues to release protective antigens and confer biological containment", PNAS, 105:9361-6 (2008).
Kotula, et al., "Programmable bacteria detect and record an environmental signal in the mammalian gut," Proc. Natl. Acad. Sci. U.S.A., 111,4838-4843 (2014).
Krakauer & Jansen, "Red queen dynamics of protein translation" Journal of Theoretical Biology, 218:97-109 (2002).
Krishnakumar, et al., "Transfer RNA misidentification scrambles sense codon recoding" Chembiochem, 14(15):1967-72 (2013). doi: 10.1002/cbic.201300444.
Kroll, et al., "Plasmid addiction systems: perspectives and applications in biotechnology", Micro Biotech., 3(6):634-57 (2010).
Lajoie, et al, "Genomically recoded organisms expand biological functions", Science, 342:357-360 (2013).
Lajoie, et al, "Probing the limits of genetic recoding in essential genes", Science, 342:361-363 (2013b).
Lajoie, et al., "Supplemental Materials for Genomically recoded organisms expand biological functions", Science, Supplementary Materials, http://science.sciencemag.org/content/suppl/2013/10/16/342.6156.357.DC1, 78 pages, (2013).
Lau, et al., "Large-scale recoding of a bacterial genome by iterative recombineering of synthetic DNA."Nucleic Acids Research 45:6971-6980 (2017).
Li, et al., "Biological applications of expanded genetic codes", Chembiochem, 15(16):2335-41 (2014).
Li, et al., "Reduced action of polypeptide release factors induces mRNA cleavage and tmRNA tagging at stop codons in *Escherichia coli*." Molecular Microbiology, 63:116-126 (2007).
Li, et al., "The anti-Shine-Dalgarno sequence drives translational pausing and codon choice in bacteria." Nature, 484:538-541 (2012).
Liu and Schultz, "Adding new chemistries to the genetic code", Annu. Rev. Biochem., 79:413-44 (2010).
Lutz & Bujard, "Independent and tight regulation of transcriptional units in *Escherichia coli* via the LacR/ O, the TetR/O and AraC/I1-I2 regulatory elements." Nucleic Acids Research, 25:1203-1210 (1997).
Ma & Isaacs, "Genomic Recoding Broadly Obstructs the Propagation of Horizontally Transferred Genetic Elements" Cell Systems, 3:199-207 (2016).
Ma, et al., "Organisms with alternative genetic codes resolve unassignedcodons via mistranslation and ribosomal rescue," Elife. Oct. 30, 2018;7. pii: e34878. doi: 10.7554/eLife.34878, and all of the Supplementary Materials associated therewith.
Ma, et al., "Precise manipulation of bacterial chromosomes by conjugative assembly genome engineering" Nature Protocols, 9:2285-2300 (2014).
Maisnier-Patin, et al, "Compensatory adaptation to the deleterious effect of antibiotic resistance in *Salmonella typhimurium*", Mol. Microbiol, 46:355-66 (2002).
Makarova, et al., "Evolution and classification of the CRISPR-Cas systems." Nat Rev Microbiol, 9:467-477 (2011).
Mandell, et al., "Biocontainment of genetically modified organisms by synthetic protein design", Nature, 518:(7537):55-60 (2015).
Manley, "Synthesis and degradation of termination and premature-termination fragments of beta-galactosidase in vitro and in vivo." Journal of Molecular Biology, 125:407-432 (1978).
Miyake-Stoner, et al., "Generating permissive site-specific unnatural aminoacyl-tRNA synthetases", Biochemistry, 49:1667-77 (2010).
Moe-Behrens, et al., "Preparing synthetic biology for the world," Frontiers in Microbiology, (2013);4:5, doi:10.3389/fmicb.2013.00005.

(56) References Cited

OTHER PUBLICATIONS

Molin, et al, "Conditional Suicide System for Containment of Bacteria and Plasmids", Nat. Biotechnol, 5:1315-8 (1987).
Moore & Sauer, "Ribosome rescue: tmRNA tagging activity and capacity in *Escherichia coli*." Molecular Microbiology, 58:456-466 (2005).
Morgan, et al., "Bacteriophage Mu genome sequence: analysis and comparison with Mu-like prophages in Haemophilus, Neisseria and Deinococcus." J Mol Biol, 317:337-359 (2002).
Mukai, et al., "Codon reassignment in the *Escherichia coli* genetic code", Nucleic Acids Res., 38:8188-95 (2010).
Napolitano, et al., ". Emergent rules for codon choice elucidated by editing rare arginine codons in *Escherichia coli*." PNAS, 113:E5588-E5597 (2016).
NCBI Accession AP001918.1, GI: 8918823, "*Escherichia coli* K-12 plasmid F DNA, complete sequence", accessed Feb. 5, 2021.
NCBI Accession L27758.1, GI 508311, "Pseudomonas aeruginosa plasmid Birmingham IncP-alpha, complete sequence" accessed Feb. 5, 2021.
Nelson, et al., "The traY gene product and integration host factor stimulate *Escherichia coli* DNA helicase I-catalyzed nicking at the F plasmid oriT." J Biol Chem, 270:28374-28380. (1995).
Nogales, et al., "Influenza A virus attenuation by codon deoptimization of the NS gene for vaccine development." J Virol., 88:10525-10540 (2014).
Ochman, et al., "Lateral gene transfer and the nature of bacterial innovation," Nature, 405:299-304 (2000).
Odonoghue, et al., "Near-cognate suppression of amber, opal and quadruplet codons competes with aminoacyl-tRNAPyl for genetic code expansion", FEBS Lett., 586(21):3931-3937 (2012).
Ohtake, et al., "Efficient Decoding of the UAG Triplet as a Full-Fledged Sense Codon Enhances the Growth of a prfA-Deficient Strain of *Escherichia coli*", Journal of Bacteriology, 194(10):2606-2613 (2012).
Ostrov, et al., "Design, synthesis, and testing toward a 57-codon genome" Science, 353(6301):819-22 (2016). doi: 10.1126/science.aaf3639.
Ou, "Inhibition of formation of *Escherichia coli* mating pairs by f1 and MS2 bacteriophages as determined with a Coulter counter." Journal of bacteriology,114:1108-1115 (1973).
Paddon, et al., "High-level semi-synthetic production of the potent antimalarial artemisinin," Nature, 496:528-532 (2013).
Pansegrau, et al., "Complete nucleotide sequence of Birmingham IncP alpha plasmids. Compilation and comparative analysis." Journal of molecular biology, 239:623-663 (1994).
Paranchych, et al., "Stages in phage R17 infection. V. Phage eclipse and the role of F pili," Virology, 45:615-628 (1971).
Park, et al., "Expanding the genetic code of *Escherichia coli* with phosphoserine", Science, 333:1151-4 (2011).
Pech, et al., "The E Site and Its Importance for Improving Accuracy and Preventing Frameshifts. In: Atkins J. F, Gesteland R. F (Eds). Recoding: Expansion of Decoding Rules Enriches Gene Expression." New York: Springer, p. 345-362 (2010).
Petropoulos, et al., "A flexible codon in genomically recoded *Escherichia coli* permits programmable protein phosphorylation." Journal of Biological Chemistry, 289:17589-17596 (2014).
Pieper and Reineke, "Engineering bacteria for bioremediation," Curr. Opin. Biotechnol., 11: 262-70 (2000).
Pirman, "A flexible codon in genomically recoded *Escherichia coli* permits programmable protein phosphorylation," Nature Communications, 6:8130 (2015). DOI: https://doi.org/10.1038/ncomms9130, PMID: 26350500.
Richardson, et al., "Design of a synthetic yeast genome." Science, 355:1040-1044 (2017).
Roche & Sauer, "SsrA-mediated peptide tagging caused by rare codons and tRNA scarcity." The EMBO Journal, 18:4579-4589 (1999).
Ronchel and RAMOs, "Dual system to reinforce biological containment of recombinant bacteria designed for rhizoremediation," Appl Environ. Microbiol., 67,2649-56 (2001).

Rosenberger & Hilton, "The frequency of transcriptional and translational errors at nonsense codons in the lacZ gene of *Escherichia coli*." MGG Molecular & General Genetics 191:207-212 (1983).
Rovner, et al., "Recoded organisms engineered to depend on synthetic amino acids", Nature, 518:89-106 (2015).
Schaaper, et al, "Spectra of spontaneous mutations in *Escherichia coli* strains defective in mismatch correction: the nature of in vivo DNA replication errors", PNAS, 84:6220-4 (1987).
Schaub, et al., "Proteobacterial ArfA peptides are synthesized from non-stop messenger RNAs." Journal of Biological Chemistry 287:29765-29775 (2012).
Schauer, et al., "lambda N antitermination system: functional analysis of phage interactions with the host NusA protein," J Mol Biol, 194:679-690 (1987).
Schmidt and de Lorenzo, "Synthetic constructs in/for the environment: managing the interplay between natural and engineered biology," FEBS Lett., 586,2199-206 (2012).
Schmied, et al., "Controlling orthogonal ribosome subunit interactions enables evolution of new function." Nature, 564(7736):444-448 (2018).
Schultz, et al., "A genetically encoded infrared probe." J Am Chem Soc, 128:13984-5 (2006).
Seitchik, et al., "Genetically encoded tetrazine amino acid directs rapid site-specific in vivo bioorthogonal ligation with trans-cyclooctenes", J Am Chem Soc, 134:2898-901 (2012).
Seo, et al., "Transcription of an expanded genetic alphabet", J Am Chem Soc., 131(14):5046-7 (2009).
Shackelton & Holmes, "The role of alternative genetic codes in viral evolution and emergence," Journal of Theoretical Biology, 254:128-134 (2008).
Sharan, et al, "Recombineering: a homologous recombination-based method of genetic engineering", Nature Protocols, 4:206-23 (2009).
Shimizu, "ArfA recruits RF2 into stalled ribosomes." Journal of Molecular Biology, 423:624-631 (2012).
Shine & Dalgarno, "The 3'-terminal sequence of *Escherichia coli* 16S ribosomal RNA: complementarity to nonsense triplets and ribosome binding sites." PNAS, 71:1342-1346 (1974).
Smith, et al., "Efficiency of the pTF-FC2 pas poison-antidote stability system in *Escherichia coli* is affected by the host strain, and antidote degradation requires the Ion protease", J Bacteriol., 180:5458-62 (1998).
Sørensen, et al., "Studying plasmid horizontal transfer in situ: a critical review", Nature Rev. Microbiol, 3:700-10 (2005).
Steidler, et al., "Biological containment of genetically modified Lactococcus lactis for intestinal delivery of human interleukin," Nat. Biotechnol., 21(7):785-9 (2003).
Steidler, et al., "Genetically engineered probiotics," Best Pract. Res. Clin. Gastroenterol., 17, 861-876 (2003b).
Stokes, et al., "Enhancing the utility of unnatural amino acid synthetases by manipulating broad substrate specificity", Mol Biosyst, 5:1032-8 (2009).
Syvanen, et al., "Evolutionary implications of horizontal gene transfer," Annu Rev Genet, 46:341-358 (2012).
Szafranski, et al., "A new approach for containment of microorganisms: dual control of streptavidin expression by antisense RNA and the T7 transcription system", PNAS, 94:1059-63 (1997).
Thomas and Nielsen, "Mechanisms of, and barriers to, horizontal gene transfer between bacteria." Nat Rev Microbiol, 3:711-721 (2005).
Thomas and Smith, "Incompatibility group P plasmids: genetics, evolution, and use in genetic manipulation," Annu Rev Microbiol, 41:77-101 (1987).
Torres, et al, "A dual lethal system to enhance containment of recombinant micro-organisms", Microbiology, 149:3595-601 (2003).
Tu, et al., "C-terminal extension of truncated recombinant proteins in *Escherichia coli* with a 10Sa RNA decapeptide." Journal of Biological Chemistry, 270:9322-9326 (1995).
Umehara, et al., "N-acetyl lysyl-tRNA synthetases evolved by a CcdB-based selection possess N-acetyl lysine specificity in vitro and in vivo", FEBS Lett, 586:729-33 (2012).
Valentine, et al., "Characterization of mutant spectra generated by a forward mutational assay for gene A of Phi X174 from ENU-

(56) References Cited

OTHER PUBLICATIONS treated transgenic mouse embryonic cell line PX-2." Environmental and Molecular Mutagenesis, 39:55-68 (2002).

Vimberg, et al., "Translation initiation region sequence preferences in *Escherichia coli*." BMC Molecular Biology, 8:100 (2007).

Wang, et al., "Addition of the keto functional group to the genetic code of *Escherichia coli*", PNAS, 100:56-61 (2003).

Wang, et al., "Complete genome sequence of bacteriophage T5," Virology, 332:45-65 (2005).

Wang, et al., "Programming cells by multiplex genome engineering and accelerated evolution", Nature, 460:894-8 (2009).

Watson, et al., "An Mr 29000 protein is essential for mini-F maintenance in *E. coli*" Gene, 19:173-178 (1982).

Way, et al, "Integrating biological redesign: where synthetic biology came from and where it needs to go", Cell, 157:151-61 (2014).

Wu, et al, "Isolation and characterization of a glucosamine-requiring mutant of *Escherichia coli* K-12 defective in glucosamine-6-phosphate synthetase", J. Bacteriol, 105:455-66 (1971).

Wu, et al., "Multiple site-selective insertions of noncanonical amino acids into sequence-repetitive polypeptides", Chembiochem, 14:968-78 (2013).

Yamaguchi, et al., "Toxin-antitoxin systems in bacteria and archaea", Annu Rev Genet, 45:61☐79 (2011).

Yamamoto, et al., "SsrA-mediated trans-translation plays a role in mRNA quality control by facilitating degradation of truncated mRNAs." RNA, 9:408-418 (2003).

Yan, et al., "Ribosome excursions during mRNA translocation mediate broad branching of frameshift pathways." Cell, 160:870-881 (2015).

Young, et al, "An enhanced system for unnatural amino acid mutagenesis in *E. coli*", J. Mol. Biol, 395:361-74 (2010).

Young, et al., "An evolved aminoacyl-tRNA synthetase with atypical polysubstrate specificity", Biochemistry, 50:1894-900 (2011).

Zaher & Green, "Kinetic basis for global loss of fidelity arising from mismatches in the P-site codon: anticodon helix." RNA, 16:1980-1989 (2010).

Zaher & Green, "Quality control by the ribosome following peptide bond formation." Nature, 457:161-166 (2009).

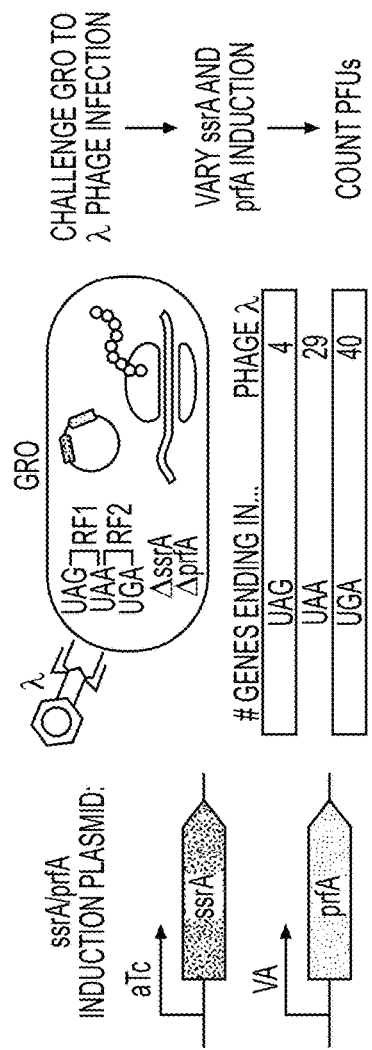
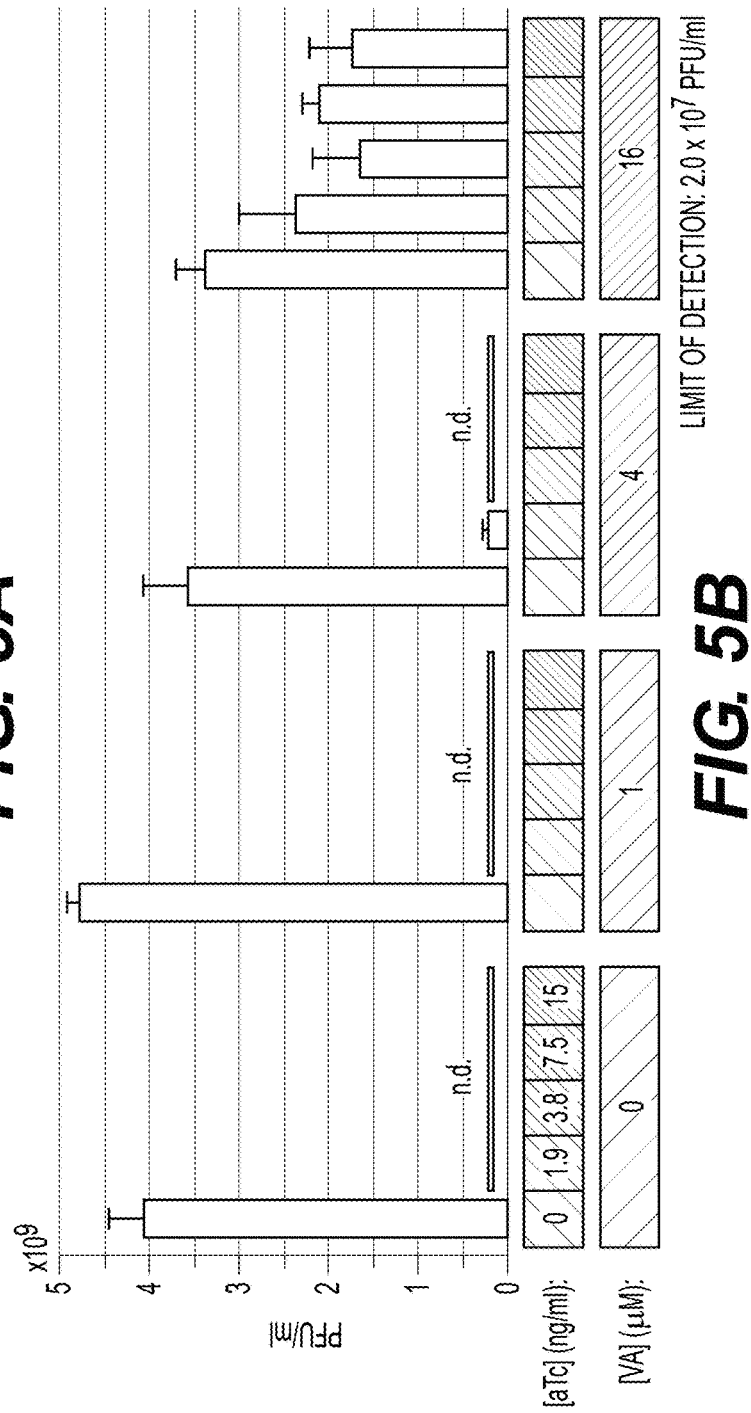
FIG. 5A
FIG. 5B

ENGINEERING ORGANISMS RESISTANT TO VIRUSES AND HORIZONTALLY TRANSFERRED GENETIC ELEMENTS

CROSS-REFERENCE TO RELATED APPLICATION

This application is a continuation of PCT/US2020/048471 filed Aug. 28, 2020, which claims benefit of and priority to U.S. Provisional Application No. 62/927,642, filed Oct. 29, 2019, which is hereby incorporated herein by reference in its entirety.

STATEMENT REGARDING FEDERALLY SPONSORED RESEARCH

This invention was made with government support under N66001-12-C-4211 and HR0011-15-C-0091 awarded by Defense Advanced Research Projects Agency, and under GM117230, GM125951 GM007499 and GM007223 awarded by the National Institutes of Health and under DE-FG02-02ER63445 awarded by the Department of Energy. The government has certain rights in the invention.

REFERENCE TO THE SEQUENCE LISTING

The Sequence Listing submitted as a text file named YU_7574_CON_ST25.txt, created on Mar. 24, 2021, and having a size of 10,899 bytes is hereby incorporated by reference pursuant to 37 C.F.R. § 1.52(e)(5).

FIELD OF THE INVENTION

The field of the invention generally relates to organisms, particularly cells, engineered to be resistant to horizontal gene transfer.

BACKGROUND OF THE INVENTION

The standard genetic code allows faithful translation of proteins across nearly all living organisms and enables exploitation of cellular machinery by horizontally transferred genetic elements (HTGEs), such as conjugative plasmids and viruses (Krakauer & Jansen, *Journal of Theoretical Biology* 218:97-109 (2002)). HTGEs also facilitate horizontal gene transfer (HGT) that can destabilize engineered organisms and compromise their functions (Baltrus, et al., *Trends Ecol. Evol.* 28,489-495 (2013), Calendar, et al. *The Bacteriophages,* 2nd ed. (Oxford University Press) (2006)), with risks ranging from inactivation mechanisms designed to isolate and contain engineered organisms (Kong et al., *Proc. Natl. Acad. Sci. USA* 105, 9361-9366, (2008); Ronchel and Ramos, *Appl. Environ. Microbiol.* 67,2649-2656 (2001)) to millions of dollars in economic damage (Bethencourt, *Nat. Biotechnol.* 27,681 (2009)). Since naturally occurring exceptions to the standard genetic code exist (Ambrogelly & Palioura, *Nature Chemical Biology* 3:29-35 (2007), Knight et al., *Nature Reviews Genetics* 2:49-58 (2001)) researchers have hypothesized that such alternative genetic codes might arise to defend against exploitation by HTGEs (Shackelton & Holmes, *Journal of Theoretical Biology* 254:128-134 (2008)). Recent research supports this hypothesis, with modification to codon usage or the genetic code reducing the ability of viruses and conjugative plasmids to exploit their hosts (Coleman et al., *Science* 320: 1784-1787 (2008), Lajoie et al., *Science* 342:357-360 (2013), Ma & Isaacs, *Cell Systems* 3:199-207 (2016)).

Given the medical, technological, and evolutionary importance of HTGE-mediated HGT (Davies, *Science* 264:375-382 (1994), Gogarten & Townsend, *Nature Reviews Microbiology* 3:679-687 (2005), Moe-Behrens et al., *Frontiers in Microbiology* 4:5 (2013), Ochman et al., *Nature* 405:299-304 (2000)), understanding the molecular basis for how alternative genetic codes impede HTGEs is important.

Thus, it is an object of the invention to provide the molecular mechanisms underlying organism susceptibility to HTGE, organisms designed to resist HTGE, and methods of use thereof.

SUMMARY OF THE INVENTION

Organisms resistant to horizontal gene transfer (HGT), and compositions and methods of use thereof are provided. The HGT-resistant organisms are typically genomically recoded organisms (GRO) having a genome in which at least one endogenous codon has been eliminated by reassignment of the codon to a synonymous or non-synonymous codon. The HGT-resistant organisms most typically are, or include, HGT-resistant cells.

The cells can also include one or more recombinant expression constructs for expression of one or more genes of one or more ribosomal rescue pathways. For example, in some embodiments, the gene or genes encode bacterial tmRNA-SmpB, ArfA, ArfB, or a combination thereof, or the corresponding gene or genes in another organism. In a preferred embodiment, the cells include a recombinant expression construct for expression of the gene encoding bacterial tmRNA or the corresponding gene(s) in another organism. In a particular embodiments, gene is ssrA.

The recombinant expression construct(s) can include a promoter, for example, a promoter heterologous to the open reading frame. The promoter can be, for example, constitutive promoter or inducible. In some embodiments, the cells includes 1 to 1,000, 1 to 500, 1 to 200, 1 to 100, 1 to 50, 1 to 25, or 1 to 20 copies of at least one of the genes. In some embodiments, one or more of the recombinant expression constructs are integrated into the genome. In some embodiments, one or more of the recombinant expression constructs can be an endogenous locus of the gene or genes under the control of a heterologous promoter. Additionally or alternatively one or more of the heterologous expression constructs are expressed extrachromosomally, from, for example, an expression vector.

In preferred embodiments, the cells exhibit an increased level of expression of one or more of the genes compared to those having only an endogenous copy of the gene at the endogenous locus under the control of the endogenous promoter. In some embodiments, expression of one or more the genes from an endogenous locus is reduced or eliminated.

The HGT-resistant cells may also include one or more additional recombinant expression constructs, e.g., for production of a recombinant protein of interest.

Any and/or all of the recombinant expression constructs can lack one or more of the eliminated codon(s).

The HGT-resistant cells are typically resistant to complete transfer and/or expression and/or propagation of a horizontally transferred genetic element (HTGE) compared to a corresponding cell having a genome wherein the codon eliminated from the HGT-resistant cell has not been eliminated. The transfer can be from another organism. In some embodiments, the organism from which the HTGE is being transferred is a bacterium or a virus. The HTGE can be, for example, an HTGE plasmid such as a conjugative plasmid, or an HTGE viral genome, or even a fragment of DNA. The virus can be a bacteriophage.

The codon eliminated from the cell's genome can be a sense codon. When a sense codon is eliminated, the gene encoding the cell's endogenous tRNA or tRNAs capable of decoding the eliminated sense codon can be mutated or deleted to reduce or eliminate recognition of the eliminated sense codon.

The eliminated codon can be a nonsense codon. When a nonsense codon is eliminated, the gene encoding the cell's endogenous factor or factors, e.g., release factor(s), capable of terminating translation at the eliminated nonsense codon can be mutated or deleted to reduce or eliminate recognition of the eliminated nonsense codon.

Any of the recombinant expression constructs can be heterologous to the cell.

The cell's genome can also include reassignment of a second, third, fourth, fifth, or more codons to a synonymous or non-synonymous codon. In preferred embodiments, the second codon and optional subsequent codons are reassigned to a synonymous codon. The second and optionally subsequent codons can be a sense codon(s), nonsense codon(s), codons not previously present or used in the organism, or combination thereof. When a second and/or subsequent codon is a sense codon, the gene or genes encoding the cell's endogenous tRNA or tRNAs capable of decoding the sense codon can be mutated or deleted to reduce or eliminate recognition of the codon. When a second and/or subsequent codon is a nonsense codon, the gene encoding the cell's endogenous release factor or factors capable of terminating translation at the nonsense codon can be mutated or deleted to reduce or eliminate recognition of the codon.

In some embodiments, the second and/or subsequent codons are present as a codon encoding an amino acid in the recombinant expression construct. In some embodiments, the recombinant expression construct includes between 1 and 100, 1 and 75, 1 and 50, 1 and 25, or 1 and 10, each inclusive, instances of the second and/or subsequent codon(s). In some embodiments, the cell further includes one or more orthogonal translation systems (OTS) each including an aminoacyl-tRNA synthetase (aaRS):tRNA pair or protein factor that terminates translation at the codon it recognizes, permitting site-specific incorporation of an amino acid at the second codon or subsequent codons or termination of translation during translation of protein encoded by recombinant expression construct. The amino acid(s) or termination function encoded by the second and/or subsequent codons can be recoded to encode canonical amino acids, synthetic amino acids (sAAs), non-standard amino acids (nsAAs), or a combination thereof.

The HGT-resistant cells can be prokaryotes or eukaryotes. The prokaryote can be a bacterium such as *E. coli* or Bacilli. The cells can be a eukaryote such as a fungi, insect, plant, or animal cells. The fungi can be, for example, a yeast, such as of the genus *Saccharomyces* or *Pichia*. The animal can be, for example, a mammal, such as a human or mouse.

Cultures including a plurality of the HGT-resistant cells are also provided. In some embodiments, the culture further includes one or more additional organisms capable of transferring a horizontally transferred genetic element (HTGE) to a corresponding non-HGT-resistant cell having a genome wherein the eliminated codon has not been eliminated. Typically, the HGT-resistant cell including the eliminated codon has greater resistance to HGT than the corresponding non-HGT-resistant cell without the eliminated codon. In some embodiments, the one or more additional organisms is one or more strains of bacteria, one or more viruses, or a combination thereof. The virus can be a bacteriophage. The HTGE can be or include, for example, an HTGE plasmid, such as a conjugative plasmid, or an HTGE viral genome. Compositions including a lysate of a plurality of the HGT-resistant cells are also provided.

Methods of expressing recombinant proteins in HGT-resistant cells are also provided. The methods typically including expressing a recombinant expression construct encoding the protein in a culture including a plurality of HGT-resistant cells. In some embodiments, the protein includes one or more instances of one or more non-standard or non-natural amino acids, typically decoded by an orthogonal translation system including a tRNA that can decode a reassigned codon eliminated from the HGT-resistant cell's genome, and reintroduced in a recombination expression construct encoding the protein. Compositions including protein prepared according to the expression methods are also provided. The composition can be, for example, a lysate of the cells.

BRIEF DESCRIPTION OF THE DRAWINGS

FIG. 3A—Comparison of doubling times for WT and GRO strains carrying listed deletions with and without GFP induction. Error bars show standard deviation centered at mean, n=3. FIG. 3B—Change in maximum optical density at 600 nm ($OD_{600}$) due to expression of UAG-GFP or UAA-GFP in wild-type (WT) and GRO strains carrying listed deletions. Error bars show standard deviation centered at mean, n=3. FIG. 3C—Quantification of GFP abundance per 1 mL of cells at $OD_{600}$ of 2.5 via western blot from biological replicates of indicated strains. Error bars show standard deviation centered at mean, n=3.

FIG. 4A is a bar graph showing the percent transfer of conjugative plasmid RK2 from a wild-type donor into wild-type (WT), GRO, or GRO with designated deletions (KO) as recipients. Data are obtained from technical triplicates generated from a single biological sample. FIG. 4B is a bar graph showing the percent increase in doubling time for strains carrying plasmid RK2 compared to strains lacking RK2. FIG. 4C is a bar graph showing the number of conjugation events for conjugative plasmid F from wild-type, GRO, or GRO with designated gene deletions as donors to a wild-type recipient. Data are obtained from technical triplicates generated from a single biological sample. FIG. 4D is a bar graph showing the relative titer (PFU/ml) on wild-type, GRO, and GRO with designated deletions of phage 2. Error bars show standard deviation centered at mean, n=3. p-values are calculated in relation to the GRO condition and are as follows: * is $p \leq 0.05$,  is $p \leq 0.01$, * is $p \leq 0.001$, and **** is $p \leq 0.0001$. FIG. 4E is a diagram showing the effects of sequential deletions of ribosomal rescue mechanisms on conjugative plasmid transfer efficiency. FIG. 4F is a diagram showing the effects of sequential deletions of ribosomal rescue mechanisms on viral susceptibility.

FIG. 5A is an illustration of an experimental assay designed to test induction of tmRNA and RF1 at varying levels using a plasmid, challenge GRO cells to lambda phage infection, and count PFUs. This assay allowed the measurement of HGT relative to the dosing of tmRNA and RF1 simultaneously. FIG. 5B is a bar graph showing data collected using the assay of FIG. 5A.

DETAILED DESCRIPTION OF THE INVENTION

I. Definitions

Figure 1A:
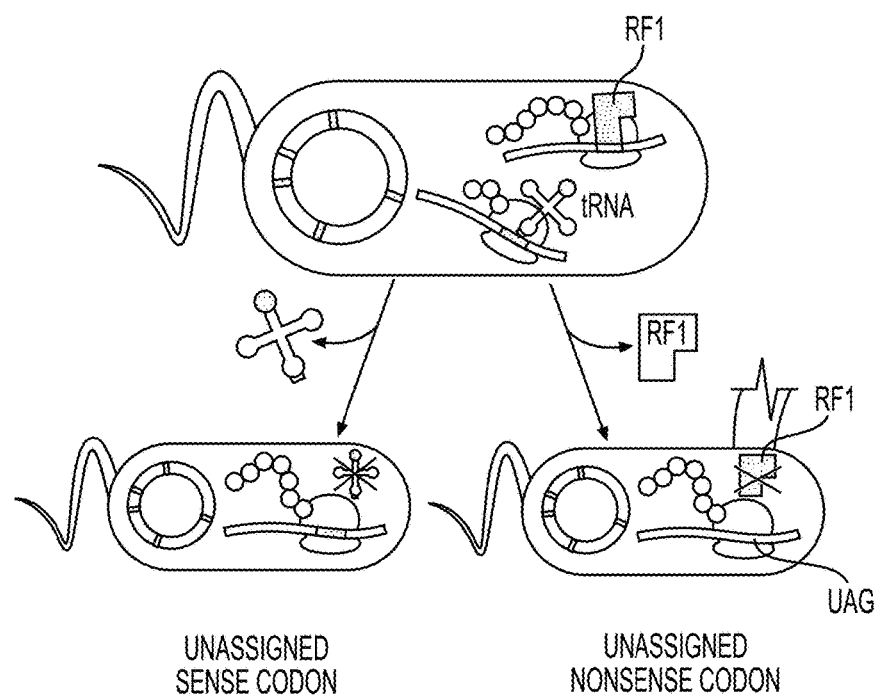
FIGS. 1A and 1B are diagrams showing UAG-ending transcript in the genomically recoded organism (GRO) may produce proteins with multiple differing C-termini when an unassigned codon is encountered in translation, thus revealing the mechanism of creating organisms resistant to HTGEs. (A) Unassigned codons arise when either the cognate tRNA or release factor recognizing a codon are removed. (B) Since the GRO lacks Release Factor 1 (RF1), ribosomal stalling at the UAG codons results in three possible fates for the nascent protein (1): (1) suppression of the codon by a near-cognate or suppressor tRNA (2) and continued translation, (2) frameshifting of bases along the mRNA transcript into a new reading frame and continued translation (3), or (3) ribosomal rescue by the ssrA-encoded tmRNA, ArfA, or ArfB proteins. If ribosomal rescue occurs via tmRNA, the resulting protein is tagged with a peptide sequence (4) for degradation, while rescue via ArfA or ArfB results in release of peptide without C-terminal modification.

As used herein, the terms "transfer RNA" and "tRNA" refers to a set of genetically encoded RNAs that act during protein synthesis as adaptor molecules, matching individual amino acids to their corresponding codon on a messenger RNA (mRNA). tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3' end of the tRNA. This amino acid is delivered to a growing polypeptide chain as the anticodon sequence of the tRNA reads a codon triplet in an mRNA.

As used herein, the term "anticodon" refers to a unit made up of typically three nucleotides that correspond to the three bases of a codon on the mRNA. Each tRNA contains a specific anticodon triplet sequence that can base-pair to one or more codons for an amino acid or "stop codon." Known "stop codons" include, but are not limited to, the three codon bases, UAA known as ochre, UAG known as amber and UGA known as opal, which do not code for an amino acid but act as signals for the termination of protein synthesis. tRNAs do not decode stop codons naturally, but can and have been engineered to do so. Stop codons are usually recognized by enzymes (release factors) that cleave the polypeptide as opposed to encode an AA via a tRNA.

As used herein, the term "suppressor tRNA" refers to a tRNA that alters the reading of a messenger RNA (mRNA) in a given translation system. For example, a nonsense suppressor tRNA can read through a stop codon.

As used herein, the term "aminoacyl tRNA synthetase (AARS)" refers to an enzyme that catalyzes the esterification of a specific amino acid or its precursor to one of all its compatible cognate tRNAs to form an aminoacyl-tRNA. These charged aminoacyl tRNAs then participate in mRNA translation and protein synthesis. The AARS show high specificity for charging a specific tRNA with the appropriate amino acid. In general, there is at least one AARS for each of the twenty amino acids.

As used herein, the term "residue" as used herein refers to an amino acid that is incorporated into a protein. The amino acid may be a naturally occurring amino acid and, unless otherwise limited, may encompass known analogs of natural amino acids that can function in a similar manner as naturally occurring amino acids.

As used herein, the terms "polynucleotide" and "nucleic acid sequence" refers to a natural or synthetic molecule including two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

As used herein, the term "vector" refers to a polynucleotide capable of transporting into a cell another polynucleotide to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector.

As used herein, the term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of gene to a transcriptional control element refers to the physical and functional relationship between the gene and promoter such that the transcription of the gene is initiated from the promoter by an RNA polymerase that specifically recognizes, binds to and transcribes the DNA.

As used herein, the terms "transformation" and "transfection" refer to the introduction of a polynucleotide, e.g., an expression vector, into a recipient cell including introduction of a polynucleotide to the chromosomal DNA of the cell.

As used herein, the term "transgenic organism" refers to any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation.

As used herein, the term "eukaryote" or "eukaryotic" refers to organisms or cells or tissues derived from these organisms belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "prokaryote" or "prokaryotic" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanocaldococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii*, and *Aeuropyrum pernix*.

As used herein, the term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "translation system" refers to the components that facilitate incorporation of an amino acid into a growing polypeptide chain (protein). Key components of a translation system generally include at least AARS and tRNA, and may also include amino acids, ribosomes, AARS, EF-Tu, and mRNA.

As used herein, the term "orthogonal translation system (OTS)" refers to at least an AARS and paired tRNA that are both heterologous to a host or translational system in which they can participate in translation of an mRNA including at least one codon that can hybridize to the anticodon of the tRNA.

As used herein, the terms "recoded organism" and "genomically recoded organism (GRO)" in the context of codons refer to an organism in which the genetic code of the organism has been altered such that a codon has been eliminated from the genetic code by reassignment to a synonymous or nonsynonymous codon.

As used herein, the term "polyspecific" refers to an AARS that can accept and incorporate two or more different non-standard amino acids.

As used herein, the terms "protein," "polypeptide," and "peptide" refers to a natural or synthetic molecule comprising two or more amino acids linked by the carboxyl group of one amino acid to the alpha amino group of another. The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus.

As used herein, "standard amino acid" and "canonical amino acid" refer to the twenty amino acids that are encoded directly by the codons of the universal genetic code denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "non-standard amino acid (nsAA)" refers to any and all amino acids that are not a standard amino acid. nsAA can be created by enzymes through posttranslational modifications; or those that are not found in nature and are entirely synthetic (e.g., synthetic amino acids (sAA)). In both classes, the nsAAs can be made synthetically. WO 2015/120287 provides a non-exhaustive list of exemplary non-standard and synthetic amino acids that are known in the art (see, e.g., Table 11 of WO 2015/120287).

As used herein, "genetically modified organism (GMO)" refers to any organism whose genetic material has been modified (e.g., altered, supplemented, etc.) using genetic engineering techniques. The modification can be extrachromasomal (e.g., an episome, plasmid, etc.), by insertion or modification of the organism's genome, or a combination thereof.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product, for example a functional RNA that does not encode a protein or polypeptide (e.g., miRNA, tRNA, etc.). The term gene as used herein with reference to genomic DNA includes intervening, non-coding regions as well as regulatory regions and can include 5' and 3' untranslated ends. The term gene as used herein with reference to recombinant expression constructs may, but need not, include intervening, non-coding regions, regulatory regions, and/or 5' and 3' untranslated ends. Thus, with respect to a recombinant expression constructs, a gene may be only an open reading frame (ORF).

As used herein, the term "construct" refers to a recombinant genetic molecule having one or more isolated polynucleotide sequences. Genetic constructs used for transgene expression in a host organism, also referred to "expression constructs", include in the 5'-3' direction, a promoter sequence; a sequence encoding a gene of interest; and a termination sequence. The construct may also include selectable marker gene(s) and other regulatory elements for expression.

As used herein, the term "vector" refers to a replicon, such as a plasmid, phage, or cosmid, into which another DNA segment may be inserted so as to bring about the replication of the inserted segment. The vectors can be expression vectors.

As used herein, the term "expression vector" refers to a vector that includes one or more expression control sequences.

As used herein, term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, the term "promoter" refers to a regulatory nucleic acid sequence, typically located upstream (5') of a gene or protein coding sequence that, in conjunction with various elements, is responsible for regulating the expression of the gene or protein coding sequence. These include constitutive promoters, inducible promoters, tissue- and cell-specific promoters and developmentally-regulated promoters.

As used herein, the terms "transformed," "transgenic," "transfected" and "recombinant" refer to a host organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

As used herein, the term "endogenous" with regard to a nucleic acid refers to nucleic acids normally present in the host.

As used here, the term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

II. Horizontal Gene Transfer-Resistant Organisms

Horizontal gene transfer-resistant organisms (also referred to as HGT-resistant organisms) are provided.

Usually, DNA passes from parent to offspring, vertically down the generations. But not always. In some cases, it can move directly from one organism to another by a process called horizontal gene transfer (HGT). HGT, also referred to as lateral gene transfer (LGT), is the movement of genetic material between unicellular and/or multicellular organisms other than by the ("vertical") transmission of DNA from parent to offspring (reproduction).

In bacteria, this happens when DNA segments from outside the bacterial cell pass into the bacterium, such as acquisition of DNA from a virus (transduction), from another cell (conjugation), or from the environment (transformation). Because the vast majority of organisms share the same genetic code, the bacteria can read this DNA with ease, as it is in the same biological language.

Horizontal gene transfer helps bacteria adapt and evolve to their surroundings, letting them swap and share genetic information that could be useful. The process also poses a threat to human health because the DNA that bacteria share can help spread antibiotic resistance, and challenges for the stability and safety of engineered organisms because horizontally-transferred DNA can disrupt engineered functions and may also destabilize the host organism (e.g., virus infections).

As used herein, HGT is used to refer to the undesired transfer of genetic material (also referred to as horizontally transferred genetic elements (HTGE)), for example from one organism to another or taken up from the environment. HGT is distinguished from desired transfer of genetic material, e.g., recombinant expression constructs, which is typically purposely introduced by a practitioner to create a recombinant or genetic engineered organism. By using the disclosed organisms, the practitioner can control the genetic material introduced into and/or expressed by the organism, and reduce or prevent the effect of undesirable genetic materials (e.g., HTGE) on the cells.

The disclosed horizontal gene transfer-resistant organisms (also referred to as HGT-resistant organisms or cells) typically include an engineered or artificially alternative genetic code. The organisms are resistant to horizontal gene transfer because they have a modified ability to read the DNA transmitted to them. The organism can be a recombinant organism containing one or more recombinant constructs purposely introduced by a practitioner.

At the molecular level, an alternative genetic code arises from reassignment of one or more codons in the genetic code, which stems from a change in the ability of an aminoacyl-tRNA or release factor (RF) to recognize codon(s) during translation. One possible alteration of the genetic code is the loss of a codon assignment through the deletion or modification of an aminoacyl-tRNA or release factor, removing the cell's ability to decode that codon (FIG. 1A). Such unassigned codons are found in alternative genetic codes in nature (Knight et al., *Nature Reviews Genetics* 2:49-58 (2001)) and have been engineered into genomically recoded organisms (GROs) derived from *Escherichia coli* (Isaacs et al., *Science* 333:348-353 (2011), Lajoie et al., *Science* 342:357-360 (2013b)). A GRO with an unassigned UAG codon (i.e. lacking all instances of the UAG codon and release factor 1, RF1) impaired the propagation of HTGEs carrying UAG-ending genes, illustrating that alternative genetic codes can obstruct HGT (Ma & Isaacs, *Cell Systems* 3:199-207 (2016)).

Figure 1B:
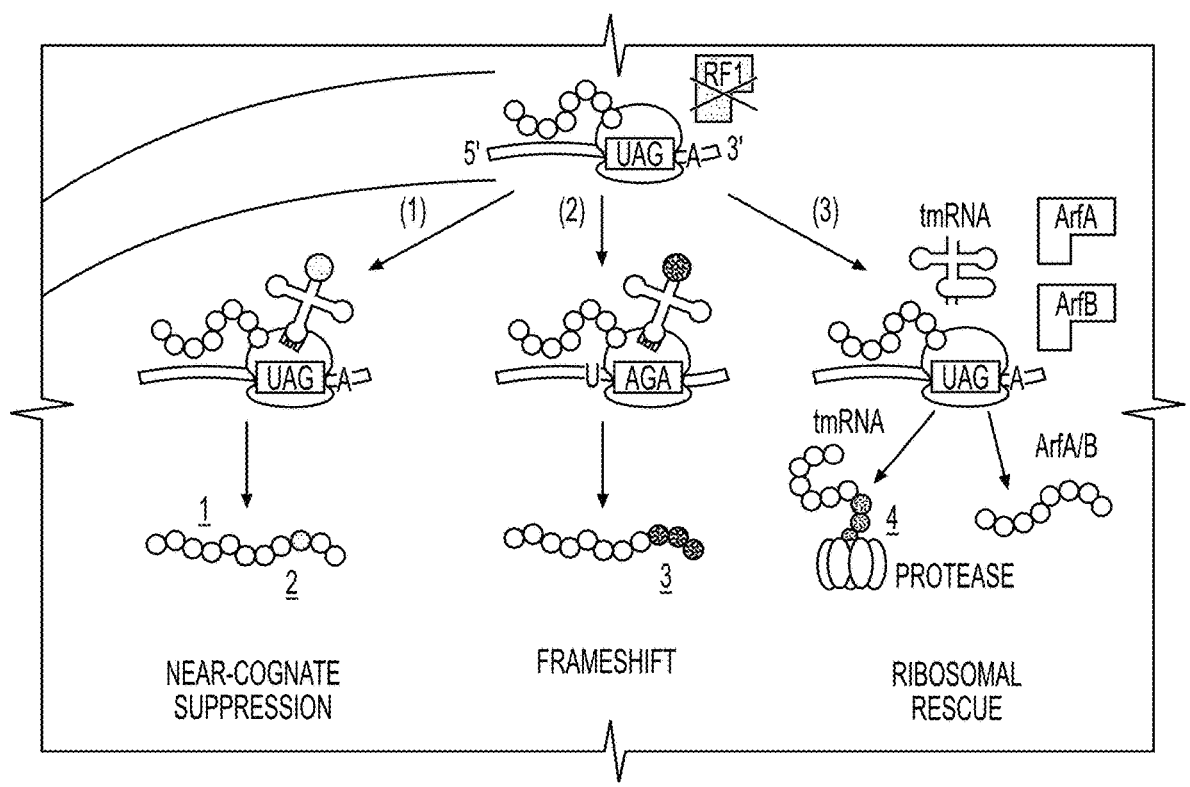

Encountering an unassigned codon during translation leads to ribosomal stalling, and without resolution, to cell death (Keiler & Feaga, *Journal of Bacteriology* 196:2123-2130 (2014)). However, the survival of organisms engineered to lack RF1 but retaining some UAG codons in their protein-coding sequences (Heinemann et al., *FEBS Letters* 586:3716-3722 (2012); Mukai et al., *Nucleic Acids Research* 38:8188-8195 (2010)) and the ability of GROs to resist exploitation by and continue growth in the presence of HTGEs (Ma & Isaacs, *Cell Systems* 3:199-207 (2016)) indicates that *E. coli* can resolve translation at unassigned UAG codons. The Examples below dissect the molecular mechanisms that resolve translation at prokaryotic ribosomes encountering these unassigned codons, each resulting in peptides with different C-terminal sequences (FIG. 1B), including: (1) suppression of the codon by a near-cognate or mutated tRNA (e.g. amber suppressor) and continued translation, (2) frameshifting of bases along the mRNA transcript into a new reading frame and continued translation, or (3) stalling that elicits one of three ribosomal rescue pathways (tmRNA-SmpB, ArfA, or ArfB) in the cell (Keiler, *Nature Reviews Microbiology* 13:285-297 (2015)).

In the most preferred embodiments, the HGT-resistant organism is a genomically recoded organism (GRO), wherein at least one codon sequence is a "blank" (i.e., it does not exist as a codon in the bacterium's genome or transcriptome), also referred to herein as an "eliminated" codon.

In some embodiments, the eliminated codons is one that is/was not previously present or used in the organism. For example, the codon was never present the organism.

The codon can be a sense or a nonsense codon.

The organisms typically are, or include cells, which themselves are HGT-resistant. Thus, the GRO can be a cell or plurality of cells.

Using this strategy to design HGT-resistant organisms creates a "genetic firewall" that prevents horizontal gene transfer of genes containing the blank codon. In this way, the organisms can be isolated from outside interference, and thus can be safer for use in, e.g., fields such as medicine and biofuel production.

The disclosed HGT-resistant organisms may be resistant to one or more different forms or types of HTGE, and/or HTGE from one or more different organisms. Such resistant may be dependent on the design of the organism, for example, the specific codon or codons eliminated from the HGT-resistant organism. In some embodiments, the organism exhibits one or more of the following: (1) the HTGE can not transfer successfully (e.g., RK2 plasmid), (2) the HTGE transfers successfully, but cannot establish itself (e.g., viruses), (3) the HTGE transfers itself and establishes itself in the host cell successfully, but then cannot be passed on to another cell (F plasmid).

The organism typically include one, two, or most preferable all three of: (1) codon reassignment that establishes an open codon, (2) elimination of translation factor(s) that decode that codon (e.g., release factors for stop codons and tRNAs for sense codons), and (3) presence of tmRNAs or homologous equivalent in the relevant organism, optionally wherein the presence of the tmRNA includes increased or overexpression thereof.

A. Features of HGT-Resistant Organisms

1. Genomically Recoded Organisms

The disclosed HGT-resistant organisms are typically genomically recoded organisms in which the genetic code of the organism has been altered such that one or more codons has been eliminated from the genetic code by reassignment to a synonymous or nonsynonymous codon.

Typically, the GRO is a cell or cells, preferably a bacterial strain, for example, an *E. coli* bacterial strain, wherein one or more codons has been replaced by a synonymous or even a non-synonymous codon. Because there are 64 possible 3-base codons, but only 20 canonical amino acids (plus stop codons), some amino acids are coded for by 2, 3, 4, or 6 different codons (referred to herein as "synonymous codons"). In a GRO, most or preferably all, of the instances of a particular codon are replaced with a synonymous (or non-synonymous) codon. Preferably, the GRO is recoded such that at least one codon is completely absent from the genome (also referred to as an eliminated codon). In some embodiments, two, three, four, five, six, seven, eight, nine, ten, or more codons are eliminated.

When a sense codon is eliminated, its elimination is preferably accompanied by mutation, or reduction or elimination of expression, of the cognate tRNA that decodes the codon during translation, reducing or eliminating the recognition of the codon by the tRNA. For example, the tRNA can be deleted from the organism, the tRNA can be mutated to recognized fewer or different codons (e.g., from recognizing AUA and AUC to just recognizing AUC), etc. In a preferred embodiments, tRNAs that decode a particular codon(s) are deleted, as in some instances (due to Wobble effect), one tRNA decodes >1 codon (e.g., AGG, AGA).

When a nonsense codon is eliminated, its elimination is preferably accompanied by mutation, reduction, or deletion of the endogenous factor or factors, for example, release factor(s), associated with terminating translation at the nonsense codon (e.g., to reduce or eliminate expression of the release factor or change the recognition specificity of codons for the release factor).

In some embodiments, wherein the organism does not have or use a certain codon(s), the unused (i.e., eliminated) codon may not be strictly considered sense or nonsense codons, but can nonetheless be utilized in the HGE-resistant strategies discussed herein. For example, an HGE-resistant organism can be created by taking a codon an organism does not have or use, but can still be recognized (see. e.g., Krishnakumar, et al., *Chembiochem.*, 14(15):1967-72 (2013). doi: 10.1002/cbic.201300444) and mutating its translation machinery, e.g., tRNA and/or factors such a release factors, to have a greater specificity, thus creating an unassigned codon.

In some embodiments, a sense codon is reassigned as a nonsense codon. Typically a release factor that recognizes the reassigned nonsense codon is also expressed by such organisms.

At least one of the eliminated codon(s) is typically a codon that is utilized by an organism by which undesired horizontal transfer of genetic material is possible. Mechanisms by which horizontal transfer is possible include, for example, (1) transformation, the genetic alteration of a cell resulting from the introduction, uptake and expression of foreign genetic material (DNA or RNA); (2) transduction, the process in which DNA is moved from one cell to another by a virus (e.g., a bacteriophage, or phage); (3) bacterial conjugation, a process that involves the transfer of DNA via a plasmid from a donor cell to a recombinant recipient cell during cell-to-cell contact; and (4) through gene transfer agents such as virus-like elements encoded by the host that are found in the alphaproteobacteria order Rhodobacterales.

Although common in prokaryotes such as bacteria, horizontal transfer also occurs in eukaryotic cells. For example, there are oncogenic viruses that lead to cancer because they carry a copy of an oncogene in their genome. Cells that are infected become cancerous because they express this oncogene. The principles and strategies discussed herein are believed to conserved and applicable across a range of organisms including prokaryotes, eukaryotes, including mammals and plants.

Thus, examples of organisms that can facilitate HGT include, but are not limited to, viruses, bacteria, archaeons, and eukaryotes. Examples of non-organism materials that can facilitate HGT include, but are not limited to, conjugative plasmids and transposons. Transfer can be between like organisms (e.g., one bacterium to another) and/or different organisms (virus to plant, bacterium to insect, etc.) and/or non-organisms (uptake of DNA from the environment).

HTGE can include, for example, plasmids including conjugative plasmids, transposons, and viral genomes.

The GRO is designed such that when the transferred gene or genes, or a component or components needed to complete the transfer, are encoded by one or more the eliminated codons, the transferred gene cannot be expressed in the GRO, and in some cases the transfer of the genetic material cannot even be completed. When the transferred genetic material is expressed by the GRO's translation machinery, ribosomal (and associated translation factors) stalling occurs at the eliminated codon.

As discussed in more detail below, removal of two or more codons from the GRO also allows reintroduction of one or more deleted codons in a gene of interest, provided at least one codon remains eliminated. The reintroduced codon is typically dedicated to a standard or non-standard amino acid, which in the presence of the appropriate orthogonal translation machinery, can be incorporated into a nascent peptide chain of during translation of an mRNA including the codon. Thus, when expression of recombinant constructs are desirable, a translation system can also be introduced to accommodate read-through of the reintroduced codon. However, preferably, as described in more detail below, the GRO, including the desirable recombinant expression constructs, maintains at least one eliminated codon, such that translation of undesirable transferred genetic material by the GRO's translation system continues to stall, while translation of the desirable heterologous expression construct is rescued.

When a GRO has two, three, or more codons replaced with a synonymous or non-synonymous codon, such GROs allow for reintroduction of the one, two, or more deleted codons in one or more recoded genes of interest, each of which may be, but is not necessarily, dedicated to a different non-standard amino acid. Such GROs can be used in combination with the appropriate orthogonal translation machinery to produce polypeptides having two, three, or more different non-standard amino acids, while also being resistant undesired HGT by maintaining at least one eliminated codon important for undesirable horizontal gene transfer or expression of transferred material thereof. In some embodiments, the undesired HGT is a horizontally transferred genetic element (HTGE). In some embodiments, two, three, four, five, or more codons remain eliminated from the GRO and are not reintroduced in the expression construct.

Exemplary design scenarios include, but are not limited to, (1) GRO with only one missing codon, (2) GRO with 2 or more missing codons, with one codon left missing as barrier to HGT, (3) GRO with 2 or more missing codons, with 2 or more codons left missing as barrier to HGT. Furthermore, in some embodiments in which 2 or more codons have been reassigned the translation systems can be re-engineered such that they encoded for different amino acids: e.g., recode Arg and Iso and then re-assign Arg-translation for Iso codons and Iso-translation for Arg codons. The foregoing are illustrative of the disclosed design principles that can also be applied to other sense and nonsense codon combinations, etc.

Different organisms often show particular preferences for one of the several codons that encode the same amino acid, and some codons are considered rare or infrequent. Preferably, the replaced codon is one that is rare or infrequent in the genome. The replaced codon can be one that codes for an amino acid (i.e., a sense codon) or a translation termination codon (i.e., a stop codon). GRO that are suitable for use as host or parental strains for the disclosed systems and methods are known in the art, or can be constructed using known methods. See, for example, Isaacs, et al., *Science*, 333, 348-53 (2011), Lajoie, et al., *Science* 342, 357-60 (2013), Lajoie, et al., *Science*, 342, 361-363 (2013). Chin, et al., *Nature*, 569(7757):514-518 (2019). doi: 10.1038/s41586-019-1192-5, Ostrov, et al., *Science*, 353(6301):819-22 (2016). doi: 10.1126/science.aaf3639. See also the Sc2.0 project focused on synthesizing a new version of *Saccharomyces cerevisiae* refer to as Sc2.0.

In some embodiments, the eliminated codon is one that codes for a rare stop codon. In a particular embodiment, the GRO is one in which all instances of the UAG (TAG) codon have been removed and replaced by another stop codon (e.g., TAA, TGA), and preferably wherein release factor 1 (RF1; terminates translation at UAG and UAA) has also been deleted, eliminating translational termination at UAG codons (Lajoie, et al., *Science* 342, 357-60 (2013)). In a particular embodiment, the GRO is C321.Δ A [321 UAG→UAA conversions and deletion of prfA (encodes RF1)] (genome sequence at GenBank accession CP006698), or a further modified strain thereof. In this GRO the UAG is eliminated. That is, UAG has been transformed from a nonsense codon (terminates translation). UAG is a preferred codon for elimination or recoding because it is the rarest codon in *Escherichia coli* MG1655 (321 known instances) and a rich collection of translation machinery capable of incorporating non-standard amino acids has been developed for UAG (Liu and Schultz, *Annu. Rev. Biochem.*, 79:413-44 (2010), discussed in more detail below).

Stop codons include TAG (UAG), TAA (UAA), and TGA (UGA). Although recoding to UAG (TAG) is discussed in more detail above, it will be appreciated that either of the other stop codons (or any sense codon) can be elimination and optionally reintroduced using the same strategy. Accordingly, in some embodiments, a sense codon is eliminated, e.g., AGG or AGA to CGG, CGA, CGC, or CGG (arginine), e.g., as the principles can be extended to any set of synonymous or even non-synonymous codons, that are coding or non-coding. The foregoing is non-limiting example.

Similarly, the cognate translation machinery can be removed/mutated/deleted to remove natural codon function (e.g., nonsense codons UAG RF1; UGA-RF2; tRNA corresponding to an eliminated sense codon, etc). The OTS system, particularly the antisense codon of the tRNA, can be designed to match a reintroduced codon, provided at least one codon remains eliminated. See also, Chin, et al., *Nature*, 569(7757):514-518 (2019). doi: 10.1038/s41586-019-1192-5, e.g., isoleucine, and Ostrov, et al., *Science*, 353(6301): 819-822 (2016) DOI: 10.1126/science.aaf3639, which describes reducing the number of codons in *E. coli* from 64 to 57 by removing instances of the UAG stop codon and excising two arginine codons, two leucine codons, and two serine codons Prokaryotes useful as GRO cells include, but are not limited to, gram negative or gram positive organisms such as *E. coli* or Bacilli, and although the most preferred host organism is a bacterial GRO, it will be appreciated the methods and compositions disclosed herein can be adapted for use on other host GRO organisms, including, but not limited to, eukaryotic cells, including e.g., yeast, fungi, insect, plant, animal, human, etc. cells, and HTGEs themselves, such as viruses.

2. Ribosomal Rescue Pathways

Stalling can elicit one or more of three ribosomal rescue pathways: tmRNA-SmpB, ArfA, or ArfB in *E. coli*, or the corresponding gene/pathway in other organisms. The tmRNA-SmpB system acts as the primary rescue mechanism in prokaryotes, resolving ribosomal stalling that arises from the translation of mRNAs lacking a stop codon due to mRNA degradation, frameshifting, and stop codon readthrough (Keiler, *Nature Reviews Microbiology* 13:285-297 (2015)). tmRNA-SmpB can also rescue ribosomes stalled on intact mRNAs for structural reasons (Cruz-Vera et al., *Current Opinion in Microbiology* 14:160-166 (2011), Keiler, *Nature Reviews Microbiology* 13:285-297 (2015), Li et al., *Nature* 484:538-541 (2012)). The ssrA-encoded tmRNA associates with SmpB to form the tmRNA-SmpB complex, which adds a C-terminal degradation tag to peptides on stalled ribosomes (Tu et al., *Journal of Biological Chemistry* 270:9322-9326 (1995)). ArfA and ArfB, the secondary ribosomal rescue systems, alleviate stalling and release the stalled ribosome's nascent peptide without modification (Chadani et al., *Molecular Microbiology* 86:37-50 (2012), Shimizu, *Journal of Molecular Biology* 423:624-631 (2012)). tmRNA, ArfA, and ArfB all act on nonstop ribosomal complexes, which are stalled ribosomes that have reached the 3' end of an mRNA because of stop-codon readthrough or because of the loss of a stop codon due to 3' exonuclease degradation (Keiler, *Nature Reviews Microbiology* 13:285-297 (2015)). A possible fourth outcome identified from in vitro studies is loss of translational fidelity after the ribosome encounters rare or unassigned codons (Gingold & Pilpel, *Molecular Systems Biology* 7:481 (2011)), followed by untemplated termination by release factor 2 (RF2) (Zaher & Green, *Nature* 457:161-166 (2009)).

Studies of ribosomal stalling arising at rare codons (Hayes et al., *PNAS* 99:3440-3445 (2002)) or in contexts of depleted or inefficient cognate decoding elements (George et al., *FEBS Letters* 590:1530-1542 (2016), Li et al., *Molecular Microbiology* 63:116-126 (2007), Roche & Sauer, *The EMBO Journal* 18:4579-4589 (1999)) indicate that a number of these mechanisms may resolve translation at unassigned codons. In the experiments detailed in the Examples below, a GRO is utilized as a model and demonstrates that unassigned UAG codons in mRNA transcripts (1) elicit suppression, ribosomal frameshifting, and ribosomal rescue, (2) can induce ribosomal frameshifting from at least −3 to +19 nucleotides, and (3) lead to total loss of translational fidelity. By selectively deleting ribosomal rescue pathways in the GRO, the tmRNA system is shown to be primarily responsible for rescuing ribosomes stalled at unassigned codons, with deletion of the tmRNA restoring expression of UAG-ending genes and re-enabling propagation of UAG-containing plasmids and viruses in the GRO.

The results below shows that loss of one or more of these pathways can rescue translation of the transferred DNA. Thus, preferably, one, two, or preferably all three of these pathways are intact in the HGT-resistant GRO. In some embodiments, the GRO expresses one or more redundancies to the tmRNA-SmpB, ArfA, and/or ArfB pathway. For example, in some embodiments, the GRO expresses an alternative, or second or subsequent gene encoding tmRNA, SmpB, ArfA, and/or ArfB. The gene can have the same, or a different, but preferably synonymous sequence to the endogenous gene(s). The alternative and/or additional genes can be expressed from the GRO's genome, extrachromosomally, or a combination thereof. The additional copy or copies of the gene(s) can be expressed from a construct or constructs inserted into the genome or from extrachromosomal expression constructs (e.g., plasmids) as discussed in more detail elsewhere herein (e.g., below with respect to translation systems). In some embodiments, the gene(s) are expressed from a single or multicopy plasmid having one or more copies of one or more genes encoding one or more elements of a ribosomal rescue pathway, e.g., tmRNA, SmpB, ArfA, and/or ArfB, or the corresponding genes/system in another organism. For example, in some embodiments, introduce multiple, redundant copies of tmRNAs across multiple sites throughout the host genome protects against loss of genetic isolation should a single copy be mutated or deleted.

In some embodiments, the one or more genes encode elements of a ribosomal rescue pathway that are autologous to the organism, heterologous to the organism, or a combination thereof. Thus, in some embodiments, one or more genes encoding one or more elements of a ribosomal rescue pathway that are expressed are from the ribosomal rescue pathways of different organisms.

Additionally or alternatively, one or more of the endogenous genes encoding one or more elements of a ribosomal rescue pathway, e.g., tmRNA, SmpB, ArfA, and/or ArfB, or the corresponding genes/system in another organism, are engineered (e.g., at the genomic locus) to be placed under the control of a heterologous promoter. The promoter can be, for example, a constitutive promoter or a regulated promoter, e.g., an inducible promoter, and may allow for increased expression of the gene(s), controlled expression of the gene(s), or both compared the endogenous promoter's activity.

The experiments below demonstrate that an unassigned stop codon acts as a barrier to HGT, but also that this barrier can be breached by mutation or deletion of the tmRNA that results in production of a functional protein. Thus, additional layers of ribosomal rescue pathways can be provided to prevent HGT in the event of mutation in the endogenous pathway(s).

In some embodiments, the endogenous gene locus for one or more genes controlling one or more ribosomal rescue pathways is deleted and reintroduced only as a heterologous expression construct so that the practitioner can control the level of the gene(s)'s expression, either by copy number, promoter activity, or both.

An organism with an unassigned sense codon would lead to premature termination at an unassigned sense codon, likely producing a nonfunctional, truncated peptide. Thus, an organism with an unassigned sense codon may have even greater barriers to HGT than an organism with an unassigned stop codon.

The organisms typically contain one or more intact rescue systems, typically comprising recombinant expression of one or more elements thereof, that intervene when protein translation stalls on the blank codon. Rescue pathways include, but are not limited to, tmRNA-SmpB, ArfA, or ArfB, in *E. coli*, and their equivalents in other prokaryotic and eukaryotic organisms. Genes encoding the tmRNA-SmpB, ArfA, and ArfB, systems in *E. coli* including ssrA, arfA, and arfB, respectively. Thus, in preferred embodiments, one, two, or preferably all three of these genes in an *E. coli* GRO, or the related host genes in a non-*E. coli* GRO, are intact and expressed, and optionally, overexpressed. Similarly, prokaryotic or eukaryotic systems that lead to degradation of the stalled protein, such as the Dom34-Hbs1 system, may be left intact or introduced to create barriers to HTGEs (Graille and Seraphin, *Nat Rev Mol Cell Biol.*, 13(11):727-35 (2012). doi: 10.1038/nrm3457). Additional and alternative pathways that can be employed in the disclosed compositions and methods include, but are not limited to, eukaryotic surveillance pathways such as nonstop decay (NSD), no-go decay (NGD) and non-functional 18S-rRNA decay (18S-NRD) (see, e.g., Graille and Seraphin, et al., *Nat Rev Mol Cell Biol.,* 2012 November; 13(11):727-35. doi: 10.1038/nrm3457).

In some embodiments, the organisms have an altered and/or increased level of expression of one or more ribosomal rescue system genes, particularly tmRNA, or its corresponding element in another organism, compared to those having only an intact endogenous ribosomal rescue system. tmRNA is conserved throughout bacteria, and the ssrA gene specifying tmRNA is also found in plastid genomes of diverse photosynthetic eukaryotes and mitochondrial of jakobids, a group of free-living, bacterivorous (see, e.g., Hafez, et al., *RNA Biol.,* 10(7): 1117-1124 (2013), and Keiler and Ramadoss, *Biochimie.* 93(11): 1993-1997 (2011)). The results presented below show the existence of a trade-off between tmRNA expression and RF1 abundance, and demonstrate the ability of robustly-expressed tmRNA to confer GRO resistance to HTGEs even in the presence of moderate levels of native UAG codon termination. It is believed that tmRNA expression levels can be tuned using synthetic promoters to confer optimal levels of HTGE resistance across a wide range of applications.

Thus, although in the GRO, when a sense codon is eliminated, its elimination is preferably accompanied by mutation, or reduction or elimination of expression, of the cognate tRNA that decodes the codon during translation, reducing or eliminating the recognition of the codon by the tRNA, such elimination may not be necessary when one or more elements of a ribosomal rescue pathway is robustly expressed. Likewise, although when a nonsense codon is eliminated, its elimination is preferably accompanied by mutation, reduction, or deletion of the endogenous factor or factors, for example, release factor(s), associated with terminating translation at the nonsense codon (e.g., to reduce or eliminate expression of the release factor or change the recognition specificity of codons for the release factor), such elimination may not be necessary when one or more elements of a ribosomal rescue pathway is robustly expressed.

B. Translation Systems

The disclosed HGT-resistant organisms can be used for a multitude of research, manufacturing, and industrial based purposes, any of which may include their expression of biomolecules including recombinant proteins. Thus, in some embodiments, the organisms are adapted for expression of one or more genes (i.e., recombinant genes) of interest, e.g., from a recombinant expression construct. The recombinant expression constructs include those capable of expressing elements of ribosomal rescue pathway, as well as other (e.g., additional) constructs for expressing other genes of interest, for example for recombinant protein production.

The recombinant construct can be a heterologous construct. In some embodiments, host cells are genetically engineered (e.g., transformed, transduced, or transfected) with the vectors encoding gene(s) of interest which can be, for example, a cloning vector or an expression vector. The vector can be, for example, in the form of a plasmid, a bacterium, a virus, a naked polynucleotide, or a conjugated polynucleotide. The expression construct can also be integrated directly into the GRO's genome.

Typically, the vectors and/or other expression constructs including those integrated into the genome are designed to avoid use of the codon eliminated from the GRO. Thus, preferably, the vectors and other expression constructs do not include at least one codon eliminated from the GRO, and preferable the at least one eliminated codon is one that is expressed by, e.g., a gene or gene(s) for which HGT is a concern or possible or likely to occur. However, in some embodiments, the GRO includes two or more eliminated codons. In such embodiments, the expression constructs may include one or more, but not all, of the eliminated constructs. In such embodiments, the reintroduction of the one or more, but not all, codons in the expression construct, and thus also during expression of its heterologous mRNA. Such GRO can be used in combination with the appropriate orthogonal translation machinery to produce polypeptides having two, three, or more different non-standard amino acids. See, e.g., WO 2015/120287 and WO 2016/073079. Such GRO may include reintroduction of the two, three, or more eliminated codons in one or more recoded genes of interest, each dedicated to a different non-standard amino acid, while also maintaining one, two, three or more eliminated codons to reduce or prevent HGT.

1. Recombinant Expression Systems a. Extrachromosomal Expression

Host cells can be genetically engineered (e.g., transformed, transduced or transfected) with the vectors encoding a protein of interest, alone or in combination with other translation system components including, but not limited to, tRNA, EF-Tu, AARS, or combinations, which can be, for example, a cloning vector or an expression vector. In some embodiments, two or more of components are expressed from the same vector.

The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface. Methods of expressing recombinant proteins in various recombinant expression systems including bacteria, yeast, insect, and mammalian cells are known in the art, see for example *Current Protocols in Protein Science* (Print ISSN: 1934-3655 Online ISSN: 1934-3663, Last updated January 2012). Plasmids can be high copy number or low copy number plasmids. In some embodiments, a low copy number plasmid generates between about 1 and about 20 copies per cell (e.g., approximately 5-8 copies per cell). In some embodiments, a high copy number plasmid generates at least about 100, 500, 1,000 or more copies per cell (e.g., approximately 100 to about 1,000 copies per cell).

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized for gene and protein expression. Viral based expression systems are well known in the art and include, but are not limited to, baculoviral, SV40, retroviral, or vaccinia based viral vectors.

Mammalian cell lines that stably express proteins can be produced using expression vectors with appropriate control elements and a selectable marker. For example, the eukaryotic expression vectors pCR3.1 (Invitrogen Life Technologies) and p91023(B) (see Wong et al. (1985) *Science* 228: 810-815) are suitable for expression of recombinant proteins in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

U6 and H1 are exemplary promoters that can be used for expressing bacterial tRNA in mammalian cells.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NSO system). The transfected cells can be cultured such that the polypeptide of interest is expressed, and the polypeptide can be recovered from, for example, the cell culture supernatant or from lysed cells.

b. Expression by Genomic Integration

Any one or more of a nucleic acid encoding a gene of interest, tRNA, EF-Tu, AARS, or combinations can be expressed from one or more genomic copies. Methods of engineering a microorganism or cell line to incorporate a nucleic acid sequence into its genome are known in the art.

For example, cloning vectors expressing a transposase and containing a nucleic acid sequence of interest between inverted repeats transposable by the transposase can be used to clone and stably insert the gene of interest into a bacterial genome. Stable insertion can be obtained using elements derived from transposons including, but not limited to Tn7, Tn9, Tn10, and Tn5. Additional methods for inserting heterologous nucleic acid sequences in *E. coli* and other gram-negative bacteria include use of specialized lambda phage cloning vectors that can exist stably in the lysogenic state, homologous recombination, and transposition.

Nucleic acids that are delivered to cells which are to be integrated into the host cell genome can contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods needed to promote homologous recombination are known to those of skill in the art.

Integrative plasmids can be used to incorporate nucleic acid sequences into yeast chromosomes. See for example, Taxis and Knop, *Bio/Tech.*, 40(1):73-78 (2006), and Hoslot and Gaillardin, *Molecular Biology and Genetic Engineering of Yeasts.* CRC Press, Inc. Boca Raton, Fla. (1992).

Methods of incorporating nucleic acid sequence into the genomes of mammalian lines are also well known in the art using, for example, engineered retroviruses such lentiviruses.

2. Orthogonal Translation System

Expression of an expression construct including an eliminated codon in combination with expression of genes encoding orthogonal AARS and tRNA that recognizes that eliminated codon will result in site specific incorporation of canonical or non-standard amino acids into the target polypeptides or proteins encoded by the specific recoded gene(s) of interest transfected or integrated into the organism. In some embodiments, host cells are genetically engineered (e.g., transformed, transduced, or transfected) with the vectors encoding orthogonal AARS, tRNA and/or recoded gene(s) of interest which can be, for example, a cloning vector or an expression vector. The vector can be, for example, in the form of a plasmid, a bacterium, a virus, a naked polynucleotide, or a conjugated polynucleotide.

Thus, translation systems may include most or all of the translation machinery of the host organism and additionally include a heterologous aminoacyl-tRNA synthetase (AARS)-rRNA pair (also referred to as an orthogonal translation system (OTS)) that can incorporate one or more non-standard amino acids into a growing peptide during translation of the recoded gene of interest. AARS are enzymes that catalyze the esterification of a specific cognate amino acid or its precursor to one or all of its compatible cognate tRNAs to form an aminoacyl-tRNA. An AARS can be specific for a single amino acid or a non-standard amino acid, or can be polyspecific for two or more non-standard amino acids, canonical amino acids, or a combination thereof. Typically, heterologous AARS can recognize, bind to, and transfer at least one non-standard amino acid to a cognate tRNA. Accordingly, the AARS can be selected by the practitioner based on the non-standard amino acid on interest. Some of the disclosed systems include two or more heterologous AARS.

tRNA is an adaptor molecule composed of RNA, typically about 76 to about 90 nucleotides in length that carries an amino acid to the protein synthetic machinery. Typically, each type of tRNA molecule can be attached to only one type of amino acid, so each organism has many types of tRNA (in fact, because the genetic code contains multiple codons that specify the same amino acid, there are many tRNA molecules bearing different anticodons which also carry the same amino acid). The heterologous tRNA used in the disclosed systems is typically one that can bind to the selected heterologous AARS and receive a non-standard amino acid to form an aminoacyl-tRNA. Because the transfer of the amino acid to the tRNA is dependent in-part on the binding of the tRNA to the AARS, these two components are typically selected by the practitioner based on their ability to interact with each other and participate in protein synthesis including the non-standard amino acid of choice in the host organism. Therefore, a selected heterologous AARS and tRNA are often referred to herein together as a heterologous AARS-tRNA pair, or an orthogonal translation system. Preferably, the heterologous AARS-tRNA pair does not cross-react with the existing host cell's pool of synthetases and tRNAs, or do so a low level (e.g., inefficiently), but is recognized by the host (e.g., endogenous) and/or orthogonal (see, e.g., Carlson, et al., *Nat Commun.*, 10(1):3920 (2019). doi: 10.1038/s41467-019-11427-y, Schmied, et al., *Nature*, 564(7736):444-448 (2018). doi: 10.1038/s41586-018-0773-z) ribosomes. Therefore, preferably the heterologous AARS cannot charge an endogenous tRNA with a non-standard amino acid (or does so a low frequency), and/or an endogenous AARS cannot charge the heterologous tRNA with a standard amino acid (or does so a low frequency). Furthermore, preferably, the heterologous AARS cannot charge its paired heterologous tRNA with a standard amino acid (or does so at low frequency).

The heterologous tRNA also includes an anticodon that recognizes the codon in the heterologous mRNA that encodes the non-standard amino acid or other target amino acid of choice. In the most preferred embodiments, the anticodon is one that hybridizes with a codon that is reduced or deleted in the host organism and reintroduced by the heterologous mRNA.

The OTS can be derived from a bacterial or eukaryotic species (e.g., yeast translational components in bacteria). In some embodiments, the AARS-tRNA pair can be from an achaea, such as *Methanococcus maripaludis, Methanocaldococcus jannaschii, Methanopyrus kandleri, Methanococcoides burtonii, Methanospirillum hungatei, Methanocorpusculum labreanum, Methanoregula boonei, Methanococcus aeolicus, Methanococcus vannieli, Methanosarcina mazei, Methanosarcina barkeri, Methanosarcina acetivorans, Methanosaeta thermophila, Methanoculleus marisnigri, Methanocaldococcus vulcanius, Methanocaldococcus fervens*, or *Methanosphaerula palustris*, or can be variant evolved therefrom.

Suitable heterologous AARS-tRNA pairs for use in the disclosed systems and methods are known in the art. For example, Table 1 and the electronic supplementary information provided in Dumas, et al., *Chem. Sci.*, 6:50-69 (2015), provide non-natural amino acids that have been genetically encoded into proteins, the reported mutations in the AARS that enable their binding to the non-natural amino acid, the corresponding tRNA, and a host organism in which the translation system is operational. See also (Schultz, et al., *J Am Chem Soc*, 128:13984-5 (2006)), Liu and Schultz, Annu. Rev. *Biochem.*, 79:413-44 (2010), Davis and Chin, *Nat. Rev. Mol. Cell Biol.*, 13:168-82 (2012), which provide additional examples of AARS-tRNA pairs which can be used in the disclosed systems and methods. See, e.g., WO 2015/120287 and WO 2016/073079.

The AARS and tRNA can be provided separately, or together, for example, as part of a single construct. In a particular embodiment, the AARS-tRNA pair is evolved from a *Methanocaldococcus jannaschii* aminoacyl-tRNA synthetase(s) (AARS)/suppressor tRNA pairs and suitable for use in an *E. coli* host organism. See, for example, Young, *J. Mol. Biol.*, 395(2):361-74 (2010), which describes an OTS including constitutive and inducible promoters driving the transcription of two copies of a *M. jannaschii* AARS gene in combination with a suppressor tRNA(CUA)(opt) in a single-vector construct.

During protein synthesis, tRNAs with attached amino acids are delivered to the ribosome by proteins called elongation factors (EF-Tu in bacteria, eEF-1 in eukaryotes), which aid in decoding the mRNA codon sequence. If the tRNA's anticodon matches the mRNA, another tRNA already bound to the ribosome transfers the growing polypeptide chain from its 3' end to the amino acid attached to the 3' end of the newly delivered tRNA, a reaction catalyzed by the ribosome. Accordingly, the heterologous AARS-tRNA pair should be one that can be processed by the host organism's elongation factor(s). Additional or alternatively, the system can include additional or alternative elongation factor variants or mutants that facilitate delivery of the heterologous aminoacyl-tRNA to the ribosome.

It will also be appreciated that methods of altering the anticodon of tRNA are known in the art. Any suitable tRNA selected for use in the disclosed systems and methods can be modified to hybridize to any desired codon. For example, although many of the heterologous tRNA disclosed here and elsewhere have a CUA anticodon, CUA can be substituted for another stop anticodon (e.g., UUA or UCA), or anticodon for any desired sense codon. The tRNA anticodon can be selected based on the GRO and the sequence of the heterologous mRNA as discussed in more detail above, and in combination with the selection of the one or more codon which will remain eliminated to reduce or prevent undesired HGT.

C. Rationally Designed Genetic Material

Rationally designed genetic materials, and methods of use thereof with HGT-resistant organisms are also provided. Such genetic material is similar to HTGE, but are typically intentionally introduced to the HGT-resistant organism and can typically be transferred to, expressed by, and/or propagated by them alone. Thus, in some embodiments, the organism are used in combination with genetic material engineered to be able to only pass between engineered cells and not wild cells.

Non-exhaustive examples are rationally designed genetic material and uses thereof include, but are not limited to, (1) live viruses that are recoded to propagate only on recoded human cells for use in vaccines, because they cannot successfully complete infection in humans, and (2) using genetic materials to propagate "changes in programming" in engineered cells in open environments. The virus/plasmid can only propoagate/function in engineered cells, so it passes from engineered cell to engineered cell and changes its function from, say, producing a plant-growth promoting hormone to fixing nitrogen.

III. Methods of Making GRO

In some embodiments preparation of the disclosed GRO include plasmid construction and transfection into the GRO. Basic molecular biology techniques are well known and the art and can be employed in plasmid construction. For example, genes and other constructs of interest can be amplified by PCR including restriction sites and can be inserted into an expression plasmid by restriction digestion-based cloning techniques. Inserts can also be amplified using primers that added homologies to the vector termini and designed to anneal to the vector. Genome integration of heterologous expression constructs, delete or recoding cassettes, etc. can also be carried by methods known in the art. In some embodiments, double-stranded DNA recombination is carried out using λ-red recombineering as previously described (Sharan, et al., *Nat. Protoc.*, 2009; 4:206-223 (2009)). Briefly, dsDNA containing the cassette of interest can be amplified from purified plasmids using primers that added about 50-bp genome homology arms at both ends, targeting specific genomic loci for integration. These fragments can be transformed into a recombination-competent strain. In some embodiments, recombinants are isolated by TolC negative selection as described in DeVito, et al., *Nucleic Acids Res.*, 36:e4 (2008). Briefly, strains are transformed with dsDNAs designed to replace tolC with a desired cassette. After dsDNA recombination and recovery, cultures are incubated with purified colicin E1 protein. Counter-selected cultures are then plated on solid media and single colonies can be screened for the expected recombination by PCR or by growth in SDS to confirm loss of resistance.

Other methods of genome modification include ssDNA recombination (Ellis, et al., *Proc. Natl. Acad. Sci. U.S.A.,* 98:6742-6746 (2001), Wang, et al., *Nature,* 460:894-898 (2009)). Briefly, a 5'-phosphorothioated oligonucleotide can be targeted to the lagging strand of the replication fork at the desired chromosomal locus. The oligonucleotide can include the modification to be made (e.g., insertion, deletion, mutation or one or more nucleotides). Recombination can be verified by Sanger sequencing the insertion loci as-needed. Exemplary parental strains and other reagents are described in more detail in the Examples below.

Any suitable combination of the disclosed methods and reagents and other methods and reagents known in the art can be used to create the disclosed GRO.

Methods of deleting, interrupting, and mutating organismal genomes are also known in the art. The mutagenesis can be random, semi-random, targeted, or a combination thereof. Preferably, the mutagenesis includes substituting one or more specific residues. In some embodiments, the mutagenesis includes one or more rounds of MAGE-based evolution. MAGE refers to multiplex automated genome evolution, and generally includes introducing multiple nucleic acid sequences into one or more cells such that the entire cell culture approaches a state involving a set of changes to each genome or targeted region (Wang et al., *Nature,* 460:894 (2009)). The method can be used to generate one specific configuration of alleles or can be used for combinatorial exploration of designed alleles optionally including additional random, i.e., not-designed, changes. This can be used with any of a variety of devices that allow the cyclic addition of many DNAs in parallel in random or specific order, with or without use of one or more selectable markers.

Compositions and methods for carrying out MAGE are described in U.S. Pat. No. 8,153,432. Briefly, MAGE-based methods typically include introducing multiple nucleic acid sequences into a cell including the steps of transforming or transfecting a cell(s) using transformation medium or transfection medium including at least one nucleic acid oligomer containing one or more mutations, replacing the transformation medium or transfection medium with growth medium, incubating the cell in the growth medium, and repeating the steps if necessary or desired until multiple nucleic acid sequences have been introduced into the cell. In some embodiments, the one or more nucleic acid oligomers is a pool of oligomers having a diversity of different random or non-random mutations at the location(s) of desired mutagenesis. Cells are transfected with a variety of combination of nucleotides leading to the formation of a diverse genomic library of mutants. The diversity of the library can be increased by increasing the number of MAGE cycles. The oligomers can be single-stranded DNA. In preferred embodiments, multiple mutations are generated in a chromosome or in a genome.

Genetic diversity of the mutants can be tuned by the number of cycles of mutagenesis. For example, increasing the number of cycles of mutagenesis generally increases the diversity of the library. In particular embodiments, a library is prepared by one or more cycles of MAGE, for example, 1, 2, 3, 4, 5, 6, 7, 8, 9, 10, 11, 12, 13, 14, 15, or more cycles, with or without intervening cycles of selection. In a particular embodiment, a library of mutants is prepared by, for example, between 1 and 50, between 3 and 15, between 5 and 9 cycles of MAGE. The cycles can occur without intervening rounds of selection to increase the diversity of library prior to selection. The methods can also be modified to include additional or alternative steps to improve genetic diversity. See, for example, Carr, et al., *Nucleic Acids Research,* 1; 40(17):e132, 12 pages (2012), and Gregg, et al., *Nucleic Acids Research,* 42(7):4779-90 (2014).

Genetic diversity can also be tuned by selecting the number and diversity of the oligonucleotides introduced during any step of the mutagenesis processes. It will be appreciated that the number of oligonucleotides can be increased, that the oligonucleotides can include one or multiple mutations per oligonucleotide and therefore target multiple position (e g, amino acid positions encoded by the target DNA); that the oligonucleotides can introduce various types of mutations (mismatches, insertions, deletions and with varying degrees of degeneracy (4N-A, T, G, C, 2 selected therefrom, or 3 selected therefrom) or specificity (N equals specific nt).

In general, MAGE experiments can be divided into three classes, characterized by varying degrees of scale and complexity: (i) many target sites, single genetic mutations; (ii) single target site, many genetic mutations; and (iii) many target sites, many genetic mutations. In the first class, MAGE has been used to recode all 321 instances of the TAG stop codon for the synonymous TAA codon using 321 discrete ssDNAs. This project yielded a strain of *E. coli* with only 63 'active' codons and a 64th 'blank' codon available for site-specific incorporation of nonstandard amino acids, or as disclosed herein, left as a 'blank codon' (i.e., eliminated codon) as a barrier to horizontal gene transfer.

In the second class, MAGE can be used to explore the effects of all possible amino acid substitutions at a single target locus. In such an experiment, it is possible, for example, to use a single degenerate ssDNA containing the NNN triplet at its center to introduce all possible amino acid substitutions. In the third class, MAGE has been used to construct diverse cell populations containing combinations of alleles across many loci involved in the biosynthesis of lycopene or aromatic amino acids. In this implementation, discrete oligos designed to knockout competing pathways by deletion can be mixed with degenerate oligos designed to randomize target positions in the coding sequence or regulatory regions of key pathway enzymes. The highly diverse population resulting from a MAGE experiment can be used downstream to screen or select for mutants with a prescribed phenotype (e.g., overproduction of a metabolite or small molecule).

Although MAGE-based mutagenesis is one example, suitable alternative methods of mutagenesis which are well known in the art can be used to create a library of variants. Exemplary methods includes, but are not limited to, error prone PCR, PCR or overlap-elongation PCR with degenerate primers, custom DNA synthesis of degenerate DNA fragments encoding the library of interest.

Additional and alternative methods of engineering a microorganism or cell line to incorporate a nucleic acid sequence into its genome are known in the art, and include, but are not limited to the genomic and extrachromosomal cloning techniques discussed above with respect to protein expression constructs.

IV. Methods of Using HGT-Resistant Organisms

The disclosed HGT-resistant organisms can be used across an array of biomedical, environmental and biotechnology applications—for instance as cellular chassis for the delivery of therapeutic compounds, for bioremediation, or simply for safe and secure cell-based production (e.g., protein production). This technology represents an important new avenue for the development of strains that can safely and securely produce industrial or medical compounds in vitro, produce therapeutic compounds in vivo, facilitate research into dangerous pathogens (i.e., as a host for viral reverse genetic systems), and may even permit release of engineered organisms for the purpose of remediation, sensing, agriculture, energy production, waste management, and medicine. For example, the disclosed HGT-resistant organisms can improve efficiency of engineered organisms, which are now being used in closed systems, such as the production of pharmaceuticals, fuels, and new chemicals. Importantly, the HGT-resistant organisms can also be used in open systems, particularly when bolstered by an additional safeguard, which include improved food production, designer probiotics to combat a host of diseases, and specialized microorganisms that clean up oil spills and landfills.

The HGT-resistant organisms can be further modified to carryout the particular task or application. For example, production of a therapeutic protein would generally include modifying the HGT-resistant organisms to include an expression construct the expresses the desired protein. Likewise, methods of bioremediation, energy production, etc., can include similar steps of modifying the HGT-resistant organisms to express an enzyme or even an entire metabolic or synthetic pathway need to carry out the desired application. Such enzymes, pathways, etc. are known in the art. The additional constructs can be expressed episomally or integrated into the genome of the organism as discussed herein and otherwise known in the art.

As introduced above, in preferred embodiments, the HGT-resistant organisms is used to express a recombinant protein. The transfected cells can be cultured such that the polypeptide of interest is expressed, and the polypeptide can be recovered from, for example, the cell culture supernatant or from lysed cells.

Other assays, methods, and applications in which the disclosed HGT-resistant organisms can be employed or adapted are known in the art. See, for example, Moe-Behrens, et al., "Preparing synthetic biology for the world," *Frontiers in Microbiology* (2013); 4:5, doi:10.3389/fmicb.2013.00005.; Paddon, et al., "High-level semi-synthetic production of the potent antimalarial artemisinin," *Nature,* 496:528-532 (2013); Pieper and Reineke, "Engineering bacteria for bioremediation," *Curr. Opin. Biotechnol.,* 11, 262-270 (2000); Steidler, L., et al., "Genetically engineered probiotics," *Best Pract. Res. Clin. Gastroenterol.,* 17, 861-876 (2003); Schmidt, M. and de Lorenzo, "Synthetic constructs in/for the environment: managing the interplay between natural and engineered biology," *FEBS Lett.,* 586, 2199-2206 (2012); Steidler, et al., "Biological containment of genetically modified *Lactococcus lactis* for intestinal delivery of human interleukin," *Nat. Biotechnol.,* 21(7):785-789 (2003); Ronchel, M. C. and Ramos, J. L., "Dual system to reinforce biological containment of recombinant bacteria designed for rhizoremediation," *Appl. Environ. Microbiol.,* 67, 2649-2656 (2001); Jensen, et al., "A substrate-dependent biological containment system for *Pseudomonas putida* based on the *Escherichia coli* gef gene," *Appl. Environ. Microbiol.,* 59, 3713-3717 (1993); Garmory, et al., "The use of live attenuated bacteria as a delivery system for heterologous antigens," *J. Drug Target.,* 11, 471-479 (2003); Anderson, et al., "Environmentally controlled invasion of cancer cells by engineered bacteria," *J. Mol. Biol.,* 355, 619-627 (2006); Dang, et al., Combination bacteriolytic therapy for the treatment of experimental tumors, *Proc. Natl. Acad. Sci. U.S.A.,* 98, 15155-15160 (2001); and Kotula, et al., "Programmable bacteria detect and record an environmental signal in the mammalian gut," *Proc. Natl. Acad. Sci. U.S.A.,* 111, 4838-4843 (2014).

The disclosed HGT-resistant organisms can also be combined with one or more additional biocontainment strategies including, but not limited to, engineered riboregulators, reliance on synthetic amino acids, engineered toxicity and addiction can link a cell's viability to the presence of synthetic or supplemental agents for the purpose of containing GROs. See e.g., WO 2016/073079. In addition to being resistant to HGT, a bacterial strain with such a 'synthetic auxotrophy' would also be unable to grow effectively outside a controlled environment where the supplemental agent(s) is available.

Additionally or alternatively, the HGT-resistant organisms can be engineered to include a one or more 'kill switches' such that if the codon that was removed (e.g., UAG) and/or its translation factor (e.g., RF1) is reintroduced into the host, it would induce a system that would kill that particular cell. This ensures that if one of the protective measures (the deletion of translation factors) were reintroduced into the cell, there would be a kill-switch mechanism that would destroy the host.

Examples of application of the disclosed organisms include:
   Production of ultra-safe, effective vaccines—recoded viruses matched to recoded cells that can't replicate in native human cells but structurally/protein-wise look the same as the wild-type virus.
   Ability to push "new programs" through recoded genetic elements readable only by engineered organisms. The organisms pick up the engineered genetic elements and change their gene expression or protein production because of this
   Production of plant hormones or increasing bioavailability of nutrients (e.g., nitrogen fixation, conversion of insoluble phosphate into soluble phosphate, breakdown of minerals to free potassium, etc.) for improved crop production
   Preventing escape of engineered genes into the environment (e.g., a dangerous gene will not be carried on by an HTGE into a natural organism, which then acquires a new function that could turn it into a potential pathogen).

Bioremediation generally, and more specifically with respect to, landfills and oil spills, breakdown of perchlorates or other organic compounds in the soil, conversion of toxic metals to non-bioavailable forms, etc.

The disclosed compositions and methods can be further understood through the following numbered paragraphs.

1. A cell comprising:
   a genome wherein in at least one endogenous codon has been eliminated, optionally by reassignment of the codon to a synonymous or non-synonymous codon,
   and one or more recombinant expression constructs for expression of one or more genes of one or more ribosomal rescue pathways.

2. The cell of paragraph 1, wherein the gene(s) encode bacterial tmRNA-SmpB, ArfA, ArfB, or a combination thereof, or the corresponding gene or genes in another organism.

3. The cell of paragraph 2, wherein the gene(s) encode bacterial tmRNA or the corresponding gene(s) in another organism.

4. The cell of any one of paragraphs 1-3, wherein at least one of the genes is ssrA.

5. The cell of any one of paragraphs 1-4, wherein one or more of the recombinant expression constructs comprise a constitutive promoter.

6. The cell of any one of paragraphs 1-5, wherein one or more of the recombinant expression constructs comprise an inducible promoter.

7. The cell of any one of paragraphs 1-6, comprising 1 to 1,000 copies of at least one of the genes.

8. The cell of any one of paragraphs 1-7 comprising 1 to 20 copies of at least one of the genes.

9. The cell of any one of paragraphs 1-8 wherein one or more of the recombinant expression constructs is integrated into the genome.

10. The cell of paragraph 9, wherein one or more of the recombinant expression constructs comprises an endogenous locus of the gene or genes under the control of a heterologous promoter.

11. The cell of any one of paragraphs 1-10, wherein one or more of the heterologous expression constructs are expressed extrachromosomally.

12. The cell of paragraph 11, wherein the heterologous expression construct is expressed extrachromosomally from an expression vector.

13. The cell of any one of paragraphs 1-12 comprising an increased level of expression of one or more of the genes compared to those having only an endogenous copy of the gene at the endogenous locus under the control of the endogenous promoter.

14. The cell of any one of paragraphs 1-13, wherein expression of one or more the genes from an endogenous locus is reduced or eliminated.

15. The cell of any one of paragraphs 1-14, wherein the codon was reassigned to a synonymous codon.

16. The cell of any one of paragraphs 1-15, wherein the eliminated codon is a sense codon.

17. The cell of paragraph 16, wherein the gene encoding the cell's endogenous tRNA or tRNAs capable of decoding the eliminated sense codon is mutated or deleted to reduce or eliminate recognition of that codon.

18. The cell of any one of paragraphs 1-15, wherein the eliminated codon is a nonsense codon.

19. The cell of paragraph 18, wherein the gene encoding the cell's endogenous release factor or factors capable of terminating translation at the eliminated nonsense codon is mutated or deleted to reduce or eliminate recognition of that codon.

20. The cell of any one of paragraphs 1-19, wherein one or more, preferably all, of the recombinant expression constructs lack the eliminated codon.

21. The cell of any one of paragraphs 1-20, further comprising one or more additional recombinant expression construct encoding a protein of interest for recombinant protein expression, preferably wherein the additional recombinant expression construct lacks the eliminated codon.

22. The cell of any one of paragraphs 1-21, wherein the cell's genome comprises reassignment of a second codon to a synonymous or non-synonymous codon.

23. The cell of paragraph 22, wherein the second codon was reassigned to a synonymous codon.

24. The cell of paragraphs 22 or 23, wherein the second codon is a sense codon.

25. The cell of paragraph 24, wherein the gene encoding the cell's endogenous tRNA or tRNAs capable of decoding the sense second codon is mutated or deleted to reduce or eliminate recognition of that codon.

26. The cell of paragraphs 22 or 23, wherein the second codon is a nonsense codon.

27. The cell of paragraph 26, wherein the gene encoding the cell's endogenous release factor or factors capable of terminating translation at the nonsense second codon is mutated or deleted to reduce or eliminate recognition of that codon.

28. The cell of any one of paragraphs 22-27, wherein the second codon is present as a codon encoding an amino acid in the additional recombinant expression construct.

29. The cell of paragraph 28, wherein the recombinant expression construct comprises between 1 and 100, 1 and 75, 1 and 50, 1 and 25, or 1 and 10 each inclusive, instances of the second codon.

30. The cell of any one of paragraphs 24-29, further comprising an orthogonal translation system (OTS) comprising an aminoacyl-tRNA synthetase (aaRS):tRNA pair, permitting site-specific incorporation of an amino acid at the second codon during translation of protein encoded by recombinant expression construct.

31. The cell of paragraph 30, wherein the amino acid is a canonical amino acid.

32. The cell of paragraph 30, wherein the amino acid is a synthetic amino acid (sAA) or non-standard amino acid (nsAA).

33. The cell of any one of paragraphs 1-21 wherein the cell is resistant to completed transfer, propagation, expression, and/or subsequent passage of a horizontally transferred genetic element (HTGE) compared the corresponding cell comprising a genome wherein the eliminated codon has not been eliminated, lacking the one or more recombinant expression constructs, or a combination thereof.

34. The cell of paragraph 33, wherein the HTGE is a bacterium, virus, plasmid, or fragment of DNA.

35. The cell of paragraphs 33 or 34, wherein the HTGE is passed to the cell from another organism.

36. The cell of any one of paragraphs 1-35, wherein the cell is a prokaryote or a eukaryote. 37. The cell of paragraph 36, wherein the cell is a prokaryote.

38. The cell of paragraph 37, wherein the prokaryote is a bacterium.

39. The cell of paragraph 38, wherein the bacterium is an *E. coli* or Bacilli.

40. The cell of paragraph 36, wherein the cell is a eukaryote.

41. The cell of paragraph 40, wherein the eukaryote is a fungi, insect, or animal cell.

42. The cell of paragraph 41, wherein the fungi is a yeast.

43. The cell of paragraph 41, wherein the animal is a mammal.

44. The cell of any one of paragraphs 1-43 wherein the genome comprises 1, 2, 3, 4, 5, 6, 7, 8, 9, 10, or more codons that have been eliminated and are not reintroduced into the cell.

45. A culture comprising a plurality of the cells of any one of paragraphs 1-44.

46. The culture of paragraph 45, further comprising one or more additional organisms capable of transferring a horizontally transferred genetic element (HTGE) to the corresponding cell comprising a genome wherein the eliminated codon has not been eliminated.

47. The culture of paragraph 46, wherein the one or more additional organisms is one or more strains of bacteria, one or more viruses, or a combination thereof.

48. The culture of paragraphs 46 or 47, wherein the HTGE is an HTGE plasmid or an HTGE viral genome.

49. The culture of paragraph 48, wherein the HTGE plasmid is a conjugative plasmid.

50. The culture of any one of paragraphs 45-49, wherein the culture is in a closed culture system.

51. The culture of any one of paragraphs 45-49 wherein the culture is in an open system.

52. A composition comprising lysate of a plurality of the cells of any one of paragraphs 1-44.

53. A method of expressing a protein of interest comprising expressing a recombinant expression construct encoding the protein of interest in a culture comprising a plurality of the cells of any one of paragraphs 1-44.

54. The method of paragraph 53, wherein the protein comprises one or more instances of one or more non-standard or non-natural amino acids.

55. A composition comprising protein prepared according to a method comprising expression of the recombinant expression construct encoding the protein in a culture comprising a plurality of the cells of any one of paragraphs 1-44.

56. The composition of paragraph 55, comprising or consisting of a lysate of the cells.

EXAMPLES

Ma, et al., "Organisms with alternative genetic codes resolve unassignedcodons via mistranslation and ribosomal rescue," *Elife*. 2018 Oct. 30; 7. pii: e34878. doi: 10.7554/eLife.34878, and all of the Supplementary Materials associated therewith are specifically incorporated by reference herein in their entireties.

Materials and Methods used in the Examples 1-3.
Strains and Media

Key Resources Table

| Reagent type (species) or resource | Designation | Source or reference | Identifiers | Additional Information | Issacs Lab Reference # | Full genotype of strains | # UAG Codons | RF1 status | Ribosomal rescue gene knockout | ssrA tag status |
|---|---|---|---|---|---|---|---|---|---|---|
| Gene (*Escherichia coli*) | pUAG-GFP | this paper | eGFP-6xHis-UAG; Plasmid NJM88; Strain NJM1242 | eGFP protein with a C-terminal 6-His tag for protein purification, terminating translation in a UAG codon. | Plasmid NJM88; Strain NJM1242 | N/A | N/A | N/A | N/A | N/A |
| Gene (*E. coli*) | pUAA-GFP | this paper | eGFP-6xHis-UAA; Plasmid NJM89; Strain NJM1249 | eGFP protein with a C-terminal 6-His tag for protein purification, terminating translation in a UA codon. | Plasmid NJM89; Strain NJM1249 | N/A | N/A | N/A | N/A | N/A |
| Genetic reagent (*E. coli*) | RK24 | 10.1126/science.1205822; 10.1016/j.cels.2016.06.009 | pRK24; Strain NJM699 | Conjugative RK2 plasmid (10.1006/imbi.1994.1404), but lacks functional AmpR gene. | Strain NJM699 | N/A | N/A | N/A | N/A | N/A |
| Genetic reagent (*E. coli*) | F | Yale University Coli Genetic Stock Center (CGSC), Strain #4401 | pF; Strain EMG2; Strain CGSC #4401; Strain NJM426 Strain NJM473 | Conjugative F plasmid, as described by PMID: 4568763. Obained from the Yale CGSC. | Strain NJM426; Strain NJM473 | N/A | N/A | N/A | N/A | N/A |
| Genetic reagent (*E. coli*) | pZE21_UAG-GFP | this paper | pZEtR-eGFP-cHis-TAG-v02; Plasmid NJM88; Strain NJM1242 cHis-TAA-v02; | pZE21 plasmid with pLtetO promoter driving inducible expression of eGFP with a C-terminal 6-His tag and terminating in UAG codon. Inducible with anhydro-tetacyline. | Plasmid NJM88; Strain NJM1242 | N/A | N/A | N/A | N/A | N/A |
| Genetic reagnet (*E. coli*) | pZE21_UAA-GFP | this paper | pZEtR-eGFP-Plasmid NJM89; Strain NJM1249 | pZE21 plasmid with pLtetO promoter driving inducible expression of eGFP with a C-terminal 6-His tag and terminating in UAA condon, Inducible with anhydro-tetracycline. | Plasmid NJM89; Strain NJM1249 | N/A | N/A | N/A | N/A | N/A |

-continued

| Reagent type (species) or resource | Designation | Source or reference | Identifiers | Additional Information | Issacs Lab Reference # | Full genotype of strains | # UAG Codons | RF1 status | Ribosomal rescue gene knockout | ssrA tag status |
|---|---|---|---|---|---|---|---|---|---|---|
| Genetic reagent (Enterpbacteria phage λ) | λ.CI857 | Coli Genetic Stock Center (CGSC), Yale University (contact John Wertz directly) | λ.CI857; phage; Phage NJM102 | Phage λ with temperature-sensitive CI repressor gene; when incubated at 37° C. phage becomes obligate lytic | Phages NJM102 | N/A | N/A | N/A | N/A | N/A |
| Cell line (E. coli) | GRO.DD | this paper | C31GIB. tmRNA-DD; Strain #987 | MG1655-derived strain with all 321 UAG codons mutated to UAA, deletion of RF1, and tmRNA tag C-terminal amino acids mutated from AA to DD. Retains lambda red cassette for recombineering. Investigated in FIG. 2. | Strain #987 | ΔmutS: zeo. Δ(ybhB-bioAB):[c1857. Δ(cro-ea59): tet(R-bla]. ΔprfA. tolC. tmRNA$_{DD}$ | 0 | +RF1 | n/a | DD |
| Cell line (E. coli) | GRO. DD.prfA+ | this paper | C31GIB. prgA+. tmRNA-DD; Strain #996 | MG1655-derived strain with all 321 UAG codons mutated to UAA, retains RFF1, and tmRNA tag C-terminal amino acids mutated from AA to DD. Retains lambda red cassette for recombineering. investigated in FIG. 2. | Strain #996 | ΔmutS: zeo. Δ(ybhB-bioAB):[c1857. Δ(cro-ea59): tet(R-bla]. tolC. tmRNA$_{DD}$ | 0 | ΔRF1 | n/a | DD |
| Cell line (E. coli) | ECNR2 | 10.1016/j.cels .2016.06.009 | ECNR2. ΔmutS: zeocin.Δ λRed; Strain #795 | MG1655-derived strain that contains 321 UAG codons and retains RF1. Investigated in FIGS. 3 and 4. | Strain #795 | ΔmutS: zeo. | 321 | +RF1 | n/a | AA |
| Cell line (E. coli) | GRO.AA | 10.1016/j.cels .2016.06.009 | C31.final ΔmutS: zeocin. ΔprfA. ΔλRed; Strain #796 | MG1655-derived strain with all 321 UAG codons mutated to UAA, deletion of RF1. Investigated in FIGS. 3 and 4. | Strain #796 | ΔmutS: zeo. ΔprfA (GenBank ID: CP006698) | 0 | ΔRF1 | n/a | AA |
| Cell line (E. coli) | GRO. AA.ΔarfB | this paper | C31GIB. arfB. ΔλRed; Strain #1230 | MG1655-derived strain with all 321 UAG codons mutated to UAA, deletion of RF1, and deletion of arfB. Investigated in FIGS. 3 and 4. | Strain #1230 | ΔmutS: zeo. ΔprfA. arfB:tolC | 0 | ΔRF1 | ΔssrA | AA |
| Cell line (E. coli) | GRO.AA. ΔssrA | this paper | C31GIB. ΔssrA: tolC. ΔλRed; Strain #1231 | MG1655-derived strain with all 321 UAG codons mutated to UAA, deletion of RF1, and deletion of ssrA. Investigated in FIGS. 3 and 4. | Strain #1231 | ΔmutS: zeo. ΔprfA. ssrA:tolC | 0 | ΔRF1 | ΔarfA | AA |
| Cell line (E. coli) | GRO.AA. ΔarfA | this paper | C31GIB. ΔarfA: tolC. ΔλRed; Strain #1232 | MG1655-derived strain with all 321 UAG codons mutated to UAA, deletion of RF1, and deletion of arfA. Investigated in FIGS. 3 and 4. | Strain #1232 | ΔmutS: zeo. ΔprfA. arfA:tolC | 0 | ΔRF1 | ΔarfB | AA |

-continued

Key Resources Table

| Reagent type (species) or resource | Designation | Source or reference | Identifiers | Additional Information | Issacs Lab Reference # | Full genotype of strains | # UAG Codons | RF1 status | Ribosomal rescue gene knockout | ssrA tag status |
|---|---|---|---|---|---|---|---|---|---|---|
| Cell line (*E. coli*) | GRO.AA. ΔssrA. ΔarfB | this paper | C31GIB. ΔarfB. ssrA:tolC. ΔλRed; Strain #1233 | MG1655-derived strain with all 321 UAG codons mutated to UAA, deletion of RF1, and deletion of ssrA and arfB. Investigated in FIGS. 3 and 4. | Strain #1233 | ΔmutS: zeo. ΔprfA. ΔarfB. ssrA:tolC | 0 | ΔRF1 | ΔssrA. ΔarfB | AA |
| Cell line (*E. coli*) | GRO.AA ΔarfA. ΔarfB | this paper | C31GIB. ΔarfB. arfA:tolC. ΔλRed; Strain #1234 | MG1655-derived strain with all 321 UAG condons mutated to UAA, deletion of RF1, and deletion of arfA and arfB. Investigated in FIGS. 3 and 4. | Strain #1234 | ΔmutS: zeo. ΔprfA. ΔarfB. arfA:tolC | 0 | ΔRF1 | ΔarfA. ΔarfB | AA |
| Antibody | mouse anti-GFP antibody | other | Invitrogen (Ref#: 332600, Lot#: 1513862A) | Invitrogen (Ref#: 332600, Lot#: 1513862A); (5.5 μL antibody in 3 mL Milk + TBST) | N/A | N/A | N/A | N/A | N/A | N/A |
| Antibody | goat anti-mouse antibody | other | AbCam (Ref#: ab7023, Lot#: GR1578 27-1 | AbCam (Ref#: ab7023, Lot#: GR157827-1); (2.2 μL antibody in 10 mL Milk + TBST) | N/A | N/A | N/A | N/A | N/A | N/A |
| Recombinant DNA reagent | ssrA:tolC | this paper; for use, see tolC positive/ negative selection in 10.1038/nprot .2014.081 | dsDNA NJM111 | The *E. coli* native tolC gene used to delete ssrA gene via recombineering (10.1038/nprot. 2008.227). | dsDNA NJM111 | N/A | N/A | N/A | N/A | N/A |
| Recombinant DNA reagent | arfA:tolC | this paper; for use, see tolC positive/ negative selection in 10.1038/nprot .2014.081 | dsDNA NJM112 | The *E. coli* native tolC gene used to delete arfA gene via recombineering (10.1038/nprot. 2008.227). | dsDNA NJM112 | N/A | N/A | N/A | N/A | N/A |
| Recombinant DNA reagent | arfB:tolC | this paper; for use, see tolC positive/ negative selection in 10.1038/nprot .2014.8081 | dsDNA NJM113 | The *E. coli* native tolC gene used to delete arfB gene via recombineering (10.1038/nprot. 2008.227). | dsDNA NJM1113 | N/A | N/A | N/A | N/A | N/A |
| Software algorithm | Doubling time algorithm | 10.1126/ science.1241459 | Growth_ Analyze_ GK.m | Doubling time used in 10.1126/ science.241459, written by Gleb Kuznetsov in the lab of Dr. George Church | N/A | N/A | N/A | N/A | N/A | N/A |
| Software algorithm | MaxQuant v1.5.1.2 | other | N/A | Commercial software for mass spectometry analysis. | N/A | N/A | N/A | N/A | N/A | N/A |
| Software algorithm | Graphpad Prism 7 | other | N/A | Commercial software for statistical analysis and graphing, provided through Yale University. | N/A | N/A | N/A | N/A | N/A | N/A |

All bacteria used in this study are derived from *E. coli* ECNR2, which is in turn derived from *E. coli* MG1655 (GenBank ID: U00096) in which mutS is replaced by a zeocin resistance cassette (Wang et al., *Nature* 460:894-898 (2009), Lajoie et al., *Science* 342:357-360 (2013b)). Additionally, the native bioAB genes found in MG1655 were replaced by the lambda red cassette in ECNR2. This strain is designated ECNR2.AA (see Table 1 for full genotype). For experiments expressing UAG-GFP and UAA-GFP for mass spectrometry, strains with all 321 UAG codons changed to UAA (designated 'GRO' strains) were used to control for potential differences in protein expression arising from these mutations (GenBank ID for GRO.AA: CP006698). For all other experiments, control strains labeled wild-type (WT) were MG1655 derivatives retaining all 321 UAG codons. All deletions of ssrA, arfA, and arfB were generated with a tolC resistance cassette via recombineering (Sharan et al., *Nature Protocols* 4:206-223 (2009)). Modification of the ssrA tag from AANDENYALAA (SEQ ID NO:16) to AANDENYALDD (SEQ ID NO:15) (AA→DD) to increase stability of tagged proteins was performed with MAGE as described previously (Gallagher et al., *Nature Protocols* 9:2301-2316 (2014), Wang et al., *Nature* 460:894-898 (2009)). All modifications to strains made in this study were validated through Sanger sequencing (GeneWiz; South Plainfield, N.J.).

All protein expression assays and conjugation assays were performed in LB Lennox at pH 7.5. All phage assays were performed in Tryptone-KCl (TK) media as described previously (Jaschke et al., *Virology* 434:278-284 (2012), Ma & Isaacs, *Cell Systems* 3:199-207 (2016), Valentine et al., *Environmental and Molecular Mutagenesis* 39:55-68 (2002)).

Phages and Plasmids

For viral relative titers, phage λ cI857 was used and was obtained from Dr. John Wertz at the Yale *Coli* Genetic Stock Center (CGSC) because it is obligately lytic at 37° C., preventing possible confounding factors from lysogeny. The conjugative plasmid RK2 described in Isaacs et al., *Science* 333:348-353 (2011) was used, which is a derivative of the RK2 plasmid described in Pansegrau et al., *Journal of molecular biology* 239:623-663 (1994) carrying $bla^R$ instead of $kan^R$. The complete nucleotide sequence for the plasmid is available in NCBI database, Accession L27758.1 and GI 508311. The F plasmid was obtained from the Yale CGSC (NCBI Accession AP001918.1, GI: 8918823) and added $Kan^R$ from plasmid pZE21 for antibiotic selection.

To create the UAG-GFP and UAA-GFP constructs for protein expression, an eGFP construct with a C-terminal 6×His tag was cloned downstream of pLtetO into a modified pZE21 vector with kanamycin resistance ($kan^R$) carrying a copy of the tet repressor gene (tetR) to prevent leaked gene expression. The stop codon of the eGFP construct was then modified to end in either a UAG or UAA stop codon.

Protein Expression and Purification

To obtain GFP for analysis via mass spectrometry, UAG-GFP and UAA-GFP constructs were transformed into wild-type and GRO strains carrying the AA→DD modification in the ssrA tag to prolong the half-life of tagged peptides. Experiments in the absence of the AA→DD modification yielded no peptides with ssrA degradation tags (data not shown). 50 mL cultures of each strain were grown at 33° C. in LB Lennox with 30 µg/mL kanamycin to an $OD_{600}$ of 1.0 and induced protein expression with the addition of 30 ng/uL anhydrotetracycline (aTC). After incubation overnight, cells were pelleted and resuspended in sterile phosphate buffer solution, then cells were lysed via sonication. Cell debris was then pelleted by centrifugation and GFP purified from supernatant via a nickel resin affinity column. To concentrate protein and exchange buffer for subsequent trypsin digest, GFP was concentrated via Millipore Amicon spin columns.

For whole western blots on whole cell lysates, UAG-GFP and UAA-GFP constructs were transformed into wild-type, GRO, and GRO strains with deletions of the ribosomal rescue systems. 5 mL cultures were then grown of each strain at 33° C. in LB Lennox with kanamycin overnight, then diluted all cultures $OD_{600}$ of 0.15 in fresh media containing 30 µg/mL kanamycin and 30 ng/uL aTC for 20 hr. To quantify protein expression and compare across strains, the $OD_{600}$ of all cultures was normalized to 2.5 and pelleted 1 mL of this culture, which were placed in the −80 C for 2 hr. Cell pellets were then re-suspended in lysis buffer described previously (Aerni et al., *Nucleic Acids Research* 43:e8 (2015)), incubated for 10 min on ice, centrifuged lysate, and ran 1:10 dilutions of resulting supernatant on gels for western blot analysis. Overnight starter cultures were diluted to an $OD_{600}$ of 0.15 into three separate culture tubes, and cells within each tube were induced in parallel for GFP expression. GFP was purified from each of these cultures in parallel.

Mass Spectrometry and Proteomic Analysis

Trypsin digest, sample preparation for mass spectrometry, and liquid chromatography elution gradients were performed as described previously (Aerni et al., *Nucleic Acids Research* 43:e8 (2015)). Desalted peptides were injected onto a 75 µm ID PicoFrit column (New Objective) packed to 50 cm in length with 1.9 µm ReproSil-Pur 120 Å C18-AQ (Dr. Maisch). Samples were eluted over a 90 min gradient using an EASY-nLC 1000 UPLC (Thermo) paired with a Q Exactive Plus (Thermo), using the following parameters: (MS1) 70,000 resolution, $3\times10^6$ AGC target, 300-1700 m/z scan range; (MS2) 17,500 resolution, $1\times10^6$ AGC target, top 10 mode, 1.6 m/z isolation window, 27 normalized collision energy, 90 s dynamic exclusion, unassigned and +1 charge exclusion. Peptide identification from collected spectra was performed using MaxQuant v1.5.1.2 (Cox & Mann, *Nature Biotechnology* 26:1367-1372 (2008)). Samples were searched using custom databases representing potential translational outcomes in response to the UAG codon within the GFP reporter construct, as well as the *E. coli* proteome (EcoCyc K-12 MG1655 v17). The searches considered carbamidomethyl (Cys) as a fixed modification and the following variable modifications: acetyl (N-terminal), oxidation (Met), deamidation (Asn, Gln), and phosphorylation (Ser/Thr/Tyr). Discovered peptides had a minimum length of five amino acids and could contain up to three trypsin miscleavage events. A 1% false discovery rate was used. The mass spectrometry proteomics data and the custom search databases have been deposited to the ProteomeXchange Consortium via the PRIDE partner repository (Vizcaí no et al., *Nature Biotechnology* 32:223-226 (2014)) with the dataset identifier PXD009643. Mass spectrometry spectra were manually validated by identifying all spectra with an MS/MS score over 15 and verifying the presence sufficient b- and/or y-ion series.

Western Blot Experiments and Analysis

Figure 3A:
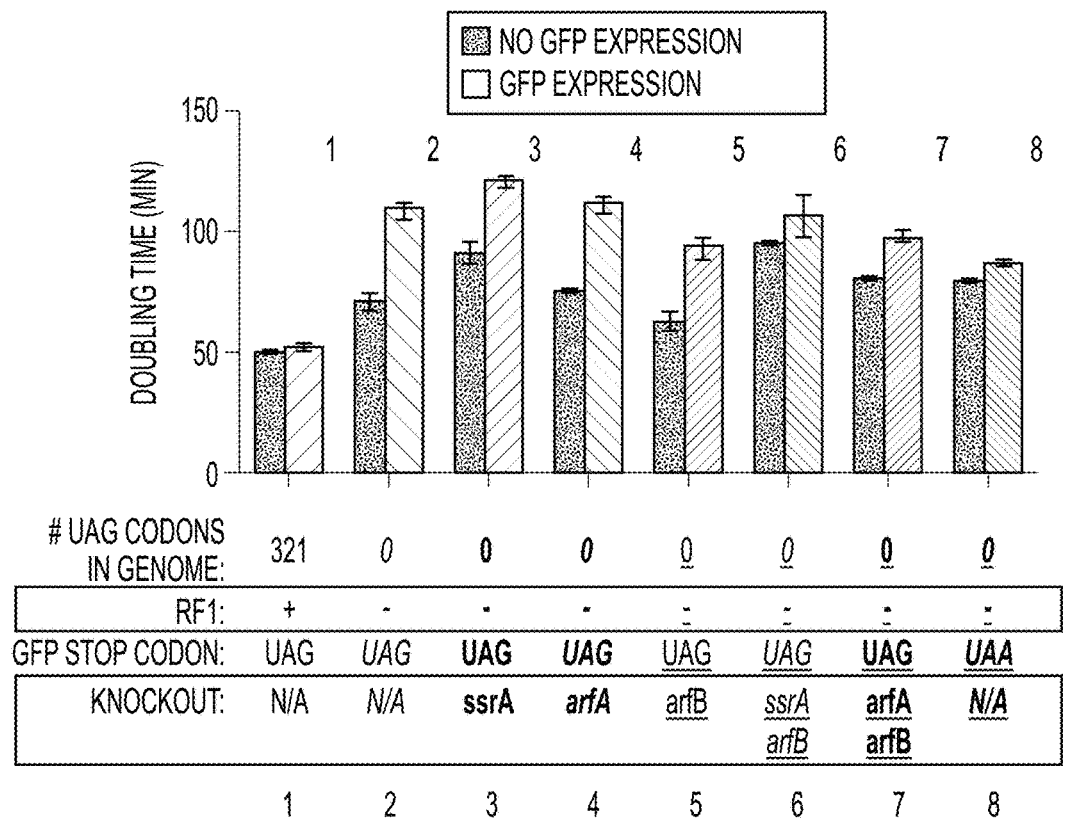
FIGS. 3A, 3B, and 3C are bar graphs showing that deletion of both ssrA and arfB restores protein production in the genomically recoded organism.
Figure 3B:
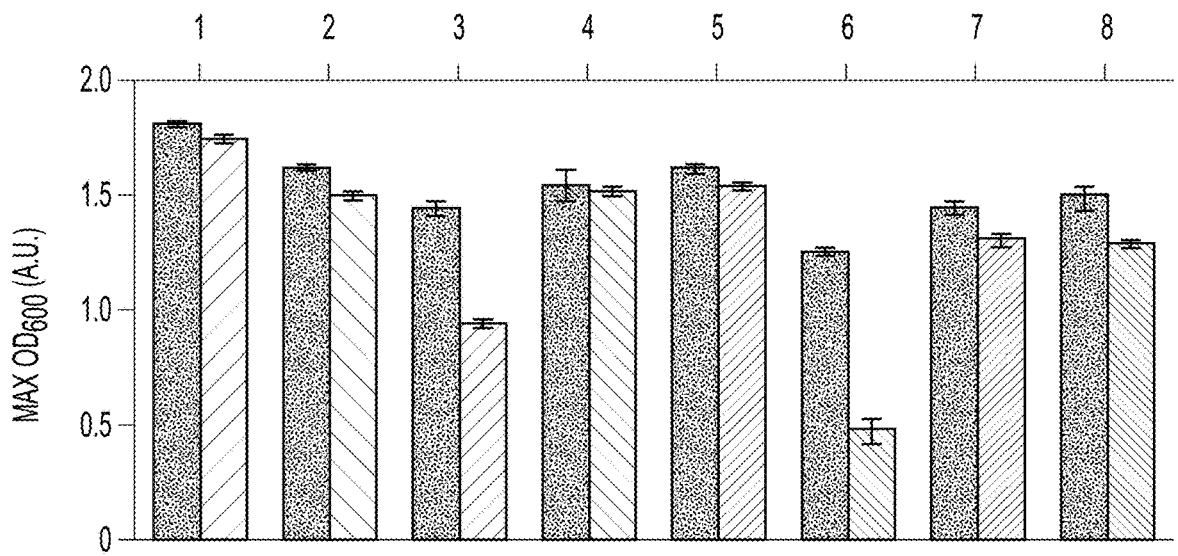

Western blots were run as described previously using SDS-PAGE gels (Pirman et al., *Nature Communications* 6:8130 (2015)). GFP-6×His standards of known amount (1, 10, 50, and 100 ng) were ran alongside experimental samples and used these standards to generate linear-range calibration curves to quantify protein abundance in experimental samples (FIGS. 3D and 3E). Because the antibody signal appeared sublinear in the 0-10 ng regime when linear regression was performed using all standards, separate linear fits were the 1-10 ng standards and the 10-100 ng standards. Experimental sample concentrations were then determined using these linear approximations. 20 of the 24 experimental samples quantified fell within or slightly above the 10-100 ng range (with the highest-intensity sample quantified as 136 ng), and 3 of the 24 samples fell within the 1-10 ng range. The one remaining sample, which had a weaker intensity than that of the 1 ng standard, was quantified through a linear approximation between the intensity of the 1 ng sample and of a blank lane with an assumed intensity of zero.

GFP-6×His was expressed as described above, normalized cell cultures to an $OD_{600}$ of 2.5, and lysed cells using BugBuster protein extraction reagent (Merck, Darmstadt, Germany). 10 µl of 1/150 diluted lysate was ran per lane of the SDS-PAGE gel. Primary mouse anti-GFP antibody was obtained from Invitrogen (Ref #: 332600, Lot #: 1513862A; RRID:AB_2234927) and goat anti-mouse antibody from AbCam (Ref #: ab7023, Lot #: GR157827-1; RRID: AB_955413). Western blots were developed using Bio-Rad Clarity Western ECL Blotting Substrate and Imaged on a GE Amersham Imager 600. Quantification of western blot bands was performed as described previously (Pirman et al., *Nature Communications* 6:8130 (2015)). Three western blots in parallel were repeated for each strain induced in separate culture tubes (i.e. biological triplicates, see Protein expression and purification).

Viral Relative Titers

To quantify relative titers, 100-fold dilutions of phage were mixed with 300 µL of mid-log ($OD_{600}$=0.5) cells in 3 mL of TK soft agar and poured onto TK solid agar plates. Starter cultures of cells were diluted to an $OD_{600}$ of 0.5 into three separate culture tubes, and cells within each tube were infected with phage lambda in parallel (i.e. biological triplicate). Each tube was plated on a separate TK solid agar plate. The plates were incubated overnight at 37° C., and counted plaques the next day.

Quantifying Conjugation

The conjugation conditions used were described previously (Ma & Isaacs, *Cell Systems* 3:199-207 (2016), Ma et al., *Nature Protocols* 9:2285-2300 (2014)). Briefly, cultures of donor and recipient cells were grown to late log in antibiotics selecting for plasmid or recipient and then rinsed and re-suspended in media to remove antibiotics. After concentrating cells to an $OD_{600}$ of 20, donors and recipients were mixed in 1:1 ratio and spotted onto pre-warmed LB Lennox agar plates in 2×20 µL and 6×10 µL pattern. For F, plates were incubated at 37° C. for 2 hr, then rinsed cells off plate, diluted serially 10-fold, and plated serial dilutions on plates containing antibiotic selecting for conjugants and incubated overnight at 37° C. For RK2, plates were incubated at 37° C. for 1 hr, then plated on agar plates selecting for the recipient. To quantify the rate of transfer, 86 colonies were picked from plates selecting for the recipient strain and patched them onto plates selecting for both recipient and conjugative plasmid, incubated plates overnight at 37° C., and counted the number of patched colonies that grew. After the conjugation, colonies were plated three times to generate technical triplicates.

Statistical and Data Analysis

All t-tests and one-way ANOVA tests for statistical significance were performed in GraphPad Prism 7. Doubling times and maximum $OD_{600}$ values were calculated from growth curve data using MATLAB (Newton, Mass.) code generated inhouse.

Experimental Replicates

The definitions for biological and technical replicates were used as outlined in Blainey et al., *Nature Methods* 11:879-880 (2014). Biological replicates consist of parallel measurements of different biological samples subjected to the same experiment, and technical replicates are parallel measurements of a single biological sample subjected to experimentation. Data represented in (FIGS. 3A-3C, 4B and 4D) are biological replicates; data represented in (FIGS. 4A and 4C) are technical replicates. Data for all 96-well plate assays (FIGS. 3A, 3B and 4B) were obtained as biological replicates: One well of each sample was grown overnight as a starter culture in a 96-well plate. Starter cultures were then inoculated into three separate wells in a separate 96-well plate.

Example 1. Suppression, Ribosomal Frameshifting, and tmRNA-Mediated Peptide Tagging Occur at Unassigned Codons Materials and Methods In prior work, an *Escherichia coli* strain was constructed in which all UAG codons were mutated to UAA, permitting the deletion of release factor 1 (RF1) and resulting in an organism that lacks a codon assignment of UAG. This genomically recoded organism (GRO) (Isaacs et al., *Science* 333:348-353 (2011), Lajoie et al., *Science* 342:357-360 (2013b)) exhibited resistance to multiple viruses and failure to propagate conjugative plasmids (Lajoie et al., *Science* 342:357-360 (2013b), Ma & Isaacs, *Cell Systems* 3:199-207 (2016)) attributable to the unassigned UAG codon, but the molecular mechanisms that resolve unassigned UAG codons during translation remained unknown. Two main experiments were conducted to uncover these mechanisms: (1) analysis of proteins translated from UAG-ending transcripts via mass spectrometry and western blots and (2) phenotypic assays to assess whether gene deletions of specific rescue factors restored the ability of conjugative plasmids and viruses to exploit the GRO. It was tested whether the tmRNA-mediated response may resolve ribosomal stalling at the UAG codon. Also the degradation tag encoded by the tmRNA from AANDENYALAA (SEQ ID NO:16) (AA-tag) was mutated to AANDENYALDD (SEQ ID NO:15) (DD-tag) for protein expression for mass spectrometry experiments. This mutation increases the half-life of protein products released by tmRNA (Keiler et al., *Science* 271:990-993 (1996), Roche & Sauer, *The EMBO Journal* 18:4579-4589 (1999)), enabling their detection via mass spectrometry.

The assembled plasmids (pUAG-GFP and pUAA-GFP) encoding green fluorescence protein (GFP) genes with C-terminal 6×-His tags positioned immediately upstream of a UAG or UAA stop codon were used. GFP was then expressed from pUAG-GFP and pUAA-GFP in GRO cells containing the RF1-encoding prfA gene (GRO.DD.prfA+) or in GRO cells lacking prfA and consequentially without UAG assignment (GRO.DD) (FIG. 2A; Table 1; see also Key Resources Table for a list of plasmids used in this study). The proteins were then purified by nickel affinity chromatography, then were trypsin digested, and used in tandem mass spectrometry to collect peptide mass data as described previously (Aerni et al., *Nucleic Acids Research* 43:e8 (2015), Amiram et al., *Nature Biotechnology* 33:1272-1279 (2015)). To distinguish between mechanisms of ribosomal rescue and mistranslation at the UAG codon, mass spectrometry data was searched with theoretical peptide libraries detailed in Table 2 to identify evidence for suppression, ribosomal frameshifting, rescue via tmRNA tagging, and loss of translational fidelity.

TABLE 1

Strains used in Examples 1-3

| Strain Abbreviation* | Ancestor (source)† | Genotype | # UAG Codons‡ | RF1 Status§ | Ribosomal rescue gene deletion | ssrA tag Status# |
|---|---|---|---|---|---|---|
| GRO.DD.prfA+ | GRO.AA (this study) | ΔmutS:zeo.Δ(ybhB-bioAB):[λcI857.Δ(cro-ea59):tetR-bla] | 0 | +RF1 | n/a | DD |
| GRO.DD | GRO.AA (this study) | ΔmutS:zeo.Δ(ybhB-bioAB):[λcI857.Δ(cro-ea59):tetR-bla], ΔprfA, ΔtolC | 0 | ΔRF1 | n/a | DD |
| ECNR2.AA | E. coli MG1655 (Wang et al., 2009) | MG1655 ΔmutS:zeo.Δ(ybhB-bioAB):[λcI857.Δ(cro-ea59):tetR-bla] | 321 | +RF1 | n/a | AA |
| GRO.AA | ECNR2.AA (Lajoie et. al., 2013b) | ΔmutS:zeo.Δ(ybhB-bioAB):[λcI857.Δ(cro-ea59):tetR-bla], ΔprfA, ΔtolC | 0 | ΔRF1 | n/a | AA |
| GRO.AA.ΔssrA | GRO.AA (this study) | ΔmutS:zeo.Δ(ybhB-bioAB):[λcI857.Δ(cro-ea59):tetR-bla], ΔprfA, ΔtolC | 0 | ΔRF1 | ΔssrA | AA |
| GRO.AA.ΔarfA | GRO.AA (this study) | ΔmutS:zeo.Δ(ybhB-bioAB):[λcI857.Δ(cro-ea59):tetR-bla], ΔprfA, ΔtolC | 0 | ΔRF1 | ΔarfA | AA |
| GRO.AA.ΔarfB | GRO.AA (this study) | ΔmutS:zeo.Δ(ybhB-bioAB):[λcI857.Δ(cro-ea59):tetR-bla], ΔprfA, ΔtolC | 0 | ΔRF1 | ΔarfB | AA |
| GRO.AA.ΔssrA.ΔarfB | GRO.AA (this study) | ΔmutS:zeo.Δ(ybhB-bioAB):[λcI857.Δ(cro-ea59):tetR-bla], ΔprfA, ΔtolC | 0 | ΔRF1 | ΔssrA, ΔarfB | AA |
| GRO.AA.ΔarfA.ΔarfB | GRO.AA (this study) | ΔmutS:zeo.Δ(ybhB-bioAB):[λcI857.Δ(cro-ea59):tetR-bla], ΔprfA, ΔtolC | 0 | ΔRF1 | ΔarfA, ΔarfB | AA |

*All strains derived from ECNR2, as described in Wang et al. (2009).
†See Key Resources Table for additional information on strains and sources. The GenBank accession number for E. coli MG1655 is U00096, and the GenBank accession number for GRO.AA is CP006698.
‡Out of a total of 321 in the original ECNR2 strain.
§RF1 terminates translation at UAG and UAA. Deletion of RF1 eliminates recognition of UAG during translation; translational termination continues through RF2, which recognizes UAA and UGA.
The ssrA gene encodes the tmRNA, which appends the ssrA degradation tag to stalled ribosomes. The wild-type sequence is AANDENYALAA (SEQ ID NO: 16); mutation of the C-terminus to AANDENYALDD (SEQ ID NO: 15) slows degradation of peptides to enable detection by mass spectrometry.

TABLE 2

Components of peptide library constructed to search and analyze tandem mass spectrometry data. The LEHHHHHHXXX (SEQ ID NO: 1) library was separate from the library that contained the entries of the first three rows of the table.

| Library component | Example peptides (from FIG. 2A) | Enables detection of . . . |
|---|---|---|
| Any one of 20 canonical amino acids inserted at the UAG codon | LEHHHHHHQGAR (SEQ ID NO: 2) | Near-cognate suppression |
| Any length of C-tail following UAG codon to the next non-UAG stop codon or to 38 amino acids | ALGDPMVR (SEQ ID NO: 3) | Readthrough, frameshifting, and rescue by ArfA or ArfB |
| AANDENYALDD (SEQ ID NO: 15) degradation tag | LEHHHHHHGDAAND ENYALDD (SEQ ID NO: 4) | Rescue by tmRNA-SmpB downstream of the UAG codon, whichever came first |

TABLE 2-continued

Components of peptide library constructed to search and analyze tandem mass spectrometry data. The LEHHHHHHXXX (SEQ ID NO: 1) library was separate from the library that contained the entries of the first three rows of the table.

| Library component | Example peptides (from FIG. 2A) | Enables detection of . . . |
| --- | --- | --- |
| All peptides of form LEHHHHHHXXX (SEQ ID NO: 1), where X is any amino acid | LEHHHHHHQLD (SEQ ID NO: 5) | Loss of translational fidelity |

Results

In the GRO lacking UAG assignment, the UAG codon elicited a combination of ribosomal rescue mechanisms and mistranslation events, including tmRNA-mediated tagging, near-cognate suppression, and frameshifting. The mutated ssrA DD-tag appended directly to the C-terminus of GFP (LEHHHHHHAANDENYALDD (SEQ ID NO:6)) appeared in both UAG- and UAA-ending transcripts in GRO.DD and GRO.DD.prfA+(FIGS. 2A and 2B), consistent with previous reports that overexpressed proteins are targeted for degradation by the tmRNA (Baneyx & Mujacic, Biotechnology 22:1399-1408 (2004), Li et al., *Molecular Microbiology* 63:116-126 (2007), Moore & Sauer, *Molecular Microbiology* 58:456-466 (2005), Tu et al., *Journal of Biological Chemistry* 270:9322-9326 (1995)). Both samples also contained the unmodified C-terminus of GFP (LEHHHHHH (SEQ ID NO:7)). In GRO.DD.prfA+, this is likely due to translational termination via RF1, while in GRO.DD this may represent rescue of nonstop ribosomes by ArfA/ArfB, release of nascent peptides undergoing translation at the time of cell lysis, or spontaneous dissociation of the ribosome, although this last event is estimated to occur fewer than once per 100,000 codon decoding events (Keiler & Feaga, *Journal of Bacteriology* 196:2123-2130 (2014)). While these were the only C-terminal fragments detected in GRO.DD expressing UAA-GFP and in GRO.DD.prfA+ expressing UAG-GFP, GRO.DD [pUAG-GFP] contained greater than 30 unique C-terminal sequences (Supplementary file 2).

Figures 2A, 2B:
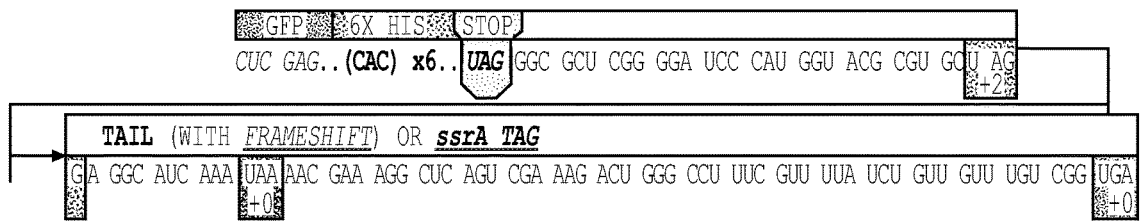
FIG. 2A is a schematic of the GFP construct with a C-terminal 6x-His tag and a UAG stop codon, showing 102 nucleotides downstream of the UAG codon and the positions of other stop codons in the downstream tail (SEQ ID NO:17).
FIG. 2B is a list of peptides identified from the C-terminus of a UAG-ending GFP construct expressed in the GRO. Purified GFP protein was digested with trypsin, processed via MS/MS, and the resulting data were computationally searched using libraries encoding all possible suppressor tRNA recognitions and all possible subsequent reading frames. Peptides are mapped to the C-terminus of the original GFP construct and grouped by reading frame, with the number of bases skipped listed in the left column. First two amino acids represent GFP, followed by the C-terminal 6xHis tag and unframeshifted readthrough, highlighted text represents the position of a UAG stop codon, followed by frameshifted readthrough, and underlined text represents the tmRNA tag. Black dashes represent ribosomal frameshifts. The peptide sequences charted in FIG. 2B are also provided according to the foregoing abbreviated convention as SEQ ID NOS: 17, 18, 7, 6, 2, 19-23, 37, 24, 3, 25-27, 38, 40, 28, 29, 9, 30, 41, 31, 32, 42, 33, 34, 11, 5, 13, 12, 14, 35, and 36 from top to bottom as-illustrated.

The peptide fragments detected from GRO.DD [pUAG-GFP] demonstrated a combination of near-cognate suppression, ribosomal frameshifting, and tmRNA tagging (FIG. 2B). Two previously known suppression events were identified glutamine (Q) and tyrosine (Y) (Aerni et al., *Nucleic Acids Research* 43:e8 (2015), Lajoie et al., *Science* 342:357-360 (2013b)), and observed two new suppressors, aspartic acid (D) and valine (V). Ribosomal frameshifting of up to −3 (LEHHHHHHH (SEQ ID NO:8)) and +19 nucleotides (LEHHHHHHMVR (SEQ ID NO:9)) were identified, as determined by the presence of fragments from all three reading frames appended to the C-terminal peptide of LEHHHHHH (SEQ ID NO:7). Additionally, the LEHHHHHHHH (SEQ ID NO:10) peptide may indicate a −6 frameshift, although it is impossible to determine whether this peptide arises from a −6 frameshift or two −3 frameshifts between histidine incorporation. Also detected were peptides encoded as far downstream as +82 nucleotides after the UAG codon, illustrating that the ribosome can continue translation after encountering the unassigned UAG codon provided that stalling at the UAG codon is resolved. Lastly, the modified ssrA DD-tag at both the site of the UAG codon and downstream on multiple peptides was identified.

Prior research in vitro revealed that a mistranslation event increases the likelihood of subsequent mistranslation events and termination by release factor 2 (RF2) (Zaher & Green, *Nature* 457:161-166 (2009)). It was investigated whether peptides representing such mistranslation events could be detected. Given the difficulty of distinguishing such peptides from suppression or frameshifting with one or two amino acids, a hypothetical peptide library containing all combinations of LEHHHHHHXXX (SEQ ID NO:1) was created, wherein X is any amino acid incorporated at the three residue positions directly downstream of the UAG codon. The search with this library returned 23 unique peptides, 14 of which met the scoring threshold of 15 (Aerni et al., *Nucleic Acids Research* 43:e8 (2015)). Five of these peptides (LEHHHHHHEKP (SEQ ID NO:11), LEHHHHHHQLD (SEQ ID NO:5), LEHHHHHHQQR (SEQ ID NO:12), LEHHHHHHSLK (SEQ ID NO:13), and LEHHHHHHYQR (SEQ ID NO:14)) could only arise from the mRNA transcript through two or more frameshift events after stalling at the UAG codon had already resolved, indicating they instead arise from loss of translational fidelity and spontaneous termination of translation following mistranslation at the UAG codon. Manual verification produced the amino acid sequences of LEHHHHHHQQR (SEQ ID NO:12) and LEHHHHHHYQR (SEQ ID NO:14), noting a 35 Da shift in mass between the Q and Y in the third position from the C-terminus.

It is improbable that these fragments arose from routine errors in mRNA transcription because this would require at least two transcriptional errors in a nine-nucleotide span. The transcription error rate in *E. coli* is estimated to be ~1 in 10,000 bases (Blank et al., *Biochemistry* 25:5920-5928 (1986), Rosenberger & Hilton, *MGG Molecular & General Genetics* 191:207-212 (1983)) and these strains have no known mutations that would lead to greater error rates in transcription. Second, it is possible that ArfA or ArfB may have terminated translation in these peptides due to 3' exonuclease shortening of the mRNA transcript as the ribosome is stalled at the UAG codon (Keiler & Feaga, *Journal of Bacteriology* 196:2123-2130 (2014), Yamamoto et al., *RNA* 9:408-418 (2003)). However, this does not explain the non-encoded tripeptides appended to the LEHHHHHH (SEQ ID NO:7) peptide. Lastly, the peptides LEHHHHHHQQR (SEQ ID NO:12), LEHHHHHHSLK (SEQ ID NO:13), and LEHHHHHHYQR (SEQ ID NO:14) may have been part of longer peptides that were cleaved off during trypsin digest. In this case, translation may have continued past the C-terminal R or K observed in these peptides, but this consideration would not apply to LEHHHHHHEKP (SEQ ID NO:11) and LEHHHHHHQLD (SEQ ID NO:5) and again does not explain the non-encoded tripeptide sequence observed appended to LEHHHHHH (SEQ ID NO:7). Given this, it was tested whether these five peptides resulted from loss of translational fidelity after stalling at the UAG codon that may lead to (1) spontaneous termination of translation due to the untemplated action of RF2 following mistranslation or (2) ArfA- or ArfB-mediated release predicated on 3' exonuclease degradation of the mRNA. The rare event of spontaneous hydrolysis of the peptide from the ribosome is also possible.

Example 2. ssrA and arfB Mediate Degradation of Proteins Containing Unassigned UAG Codons Materials and Methods Since mass spectrometry data indicated that a combination of mechanisms could resolve stalled translation at the unassigned UAG codon, targeted deletions of the ribosomal rescue systems (ssrA, arfA, and arfB) was generated in strains with wild-type ssrA sequence (GRO.AA) to determine whether protein production from UAG-ending transcripts in ΔRF1 cells could be restored to levels seen in +RF1 cells. Using recombineering (Sharan et al., *Nature Protocols* 4:206-223 (2009)), single and double deletions were produced of the ssrA, arfA, and arfB genes that encode the ribosomal rescue systems. Efforts to generate a double deletion of ssrA and arfA failed (data not shown) because the resulting phenotype is synthetic lethal (Chadani et al., *Molecular Microbiology* 78:796-808 (2010)). Each deletion strain was transformed with the UAG-GFP construct under a highly expressing, inducible pLtetO promoter (Lutz & Bujard, *Nucleic Acids Research* 25:1203-1210 (1997)) and induced GFP expression for 20 hr, measuring the effect of protein expression on cellular growth through doubling time and maximum optical density at 600 nm ($OD_{600}$) (FIGS. 3A and 3B). To quantify protein expression, whole-cell lysate from equal cell numbers were assayed, as determined by $OD_{600}$, for abundance of protein via anti-GFP western blot alongside GFP standards of known concentration as described previously (FIG. 3C) (Pirman et al., *Nature Communications* 6:8130 (2015)). As positive controls were included (1) a wild-type strain (ECNR2) expressing the UAG-GFP construct and (2) GRO.AA expressing UAA-GFP.

Results

Expression of UAG-GFP impaired GRO growth rate and cell density, generating a 54% increase in doubling time and 8% reduction in maximum $OD_{600}$ compared to cells not expressing UAG-GFP, and a 25% greater doubling time and 14% lower maximum $OD_{600}$ compared to cells expressing UAA-GFP. In contrast, ECNR2 exhibited only a 7% increase in doubling time and a 5% reduction in maximum $OD_{600}$ when expressing UAG-GFP. Although deletion strains experienced reduced growth rate as measured by doubling time compared to the GRO.AA, they exhibited a less pronounced increase in doubling time when expressing UAG-GFP (increases in doubling time between 12% and 50%) as compared to the GRO.AA (54% increase in doubling time) (FIG. 3A). However, deletion of ssrA reduced fitness during protein expression as measured by maximum $OD_{600}$, with GRO.AA.ΔssrA demonstrating a 34% reduction in max $OD_{600}$ and GRO.AA.ΔssrA.ΔarfB demonstrating a 61% decrease in max $OD_{600}$. This is potentially due to increased presence of misfolded or prematurely truncated peptides that are ordinarily tagged and degraded by the tmRNA. Interestingly, deletion of arfB produces a 50% increase in doubling time during protein expression, showing ArfB may play a role in ribosomal rescue during high levels of ribosomal stalling.

Figure 3C:
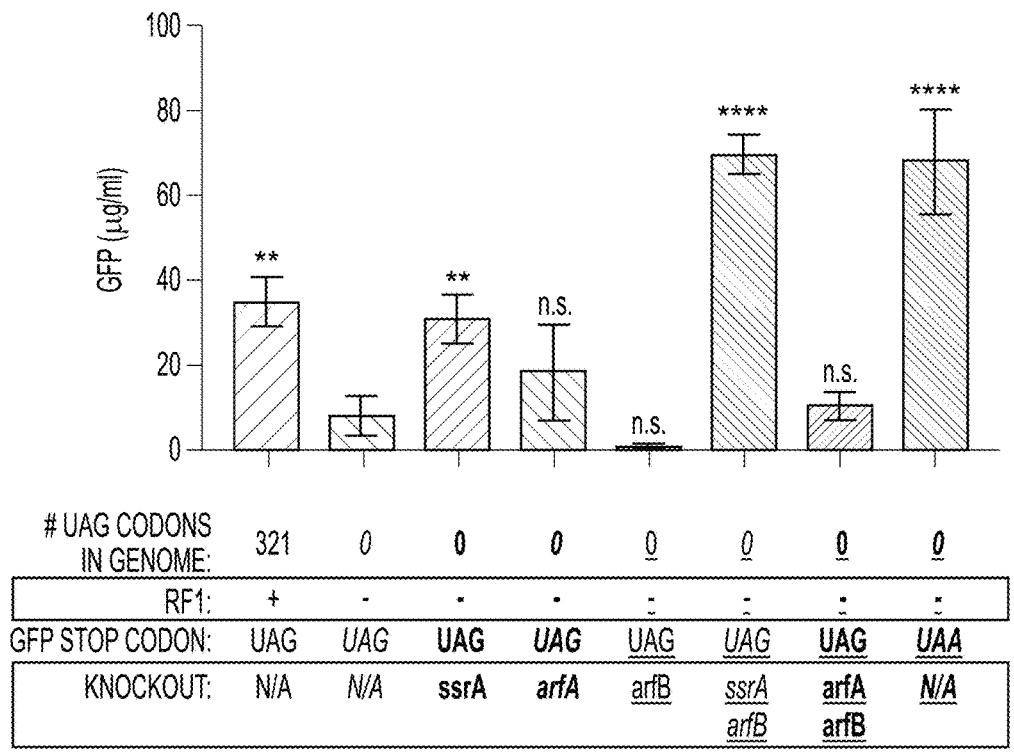
Figure 3D:
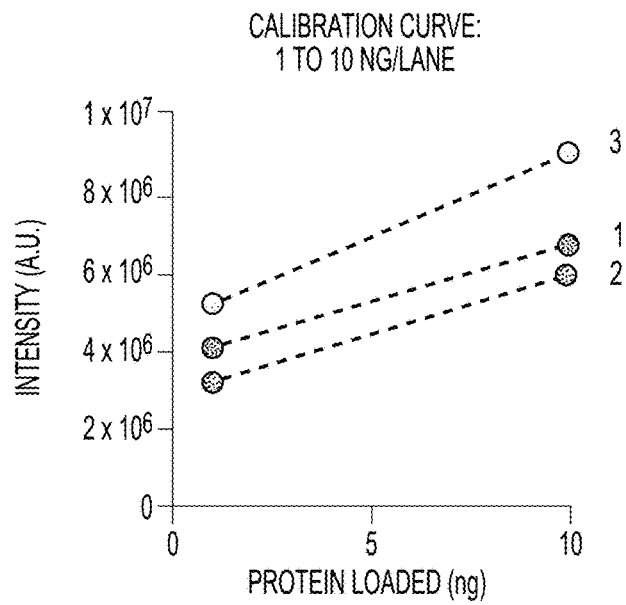
FIGS. 3D and 3E are line graphs showing linear calibration curves used to quantify GFP abundance for each replicate experiment. p-values are calculated in relation to the GRO containing the UAG-ending GFP (GRO-UAG) and are as follows: * is $p \leq 00.05$,  is $p \leq 0.01$, * is $p \leq 0.001$, and **** is $p \leq 0.0001$.
Figure 3E:
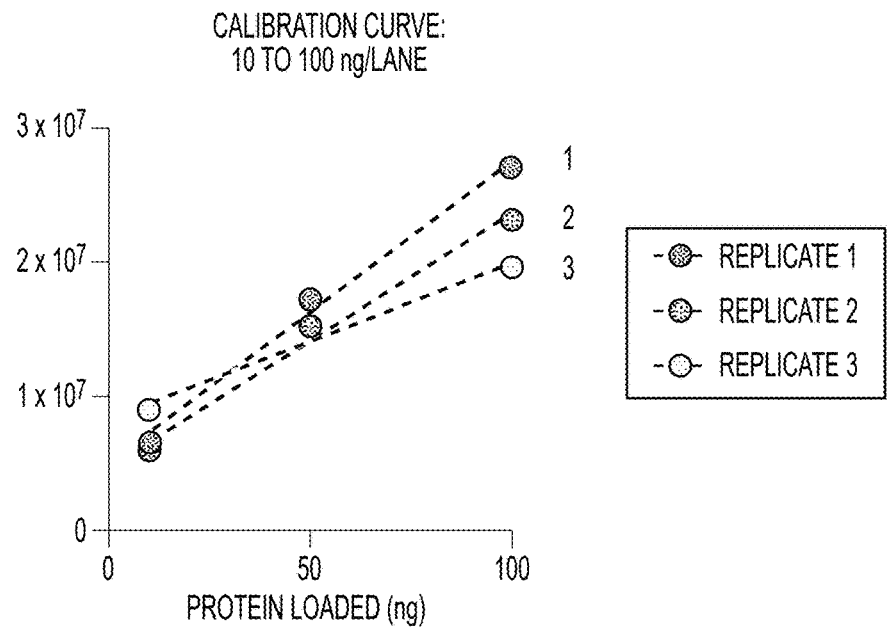

The impact of unassigned codons on protein production was investigated using western blot densitometry, and found that the GRO expressing UAG-GFP produced less than one-fourth of the protein amount than does ECNR2 expressing UAG-GFP (FIG. 3C, 8.0 mg/ml for the GRO versus 35 mg/ml for ECNR2, p=0.0014). GRO.AA expressing UAA-GFP produced nearly nine times more protein than did GRO.AA expressing UAG-GFP (68 mg/ml for GRO.AA [pUAA-GFP] versus 8.0 mg/ml for GRO.AA [pUAG-GFP], p<0.0001), indicating that the UAG codon in pUAG-GFP is the cause of reduced protein expression in the GRO. Deletion of ssrA in the UAG-GFP-expressing GRO partially restored protein production to levels seen in its UAA-GFP-expressing counterpart with no knockouts (31 mg/ml for GRO.AA.ΔssrA [pUAG-GFP] versus 68 mg/ml for GRO.AA [pUAA-GFP]) and deletion of both ssrA and arfB fully restored protein production (70. mg/ml). These ssrA deletion strains demonstrate increased GFP expression and reduced growth rate (FIG. 3A) and cell density (FIG. 3B) because translation of GFP transcripts sequesters cellular resources at the expense of cellular replication, producing GFP peptides that are freed from nonstop ribosomes via ArfA or ArfB without addition of a degradation tag.

A deletion of arfB leads to strikingly low-protein abundances from UAG-GFP transcripts that approach the lower limit of detection of the assay, although this apparent reduction in protein production was not statistically significant in comparison to protein production by GRO.AA [pUAG-GFP]. These ArfB deletion data, together with the fitness reduction observed in the GRO, indicate that ArfB is constitutively expressed and relieving low levels of ribosomal stalling in *E. coli*. These data also indicate that while deletion of ssrA partially recovers protein production from UAG-ending transcripts in the GRO, deletion of both ssrA and arfB is necessary to fully recover protein expression from UAG-ending transcripts to levels seen from the translation of UAA-ending transcripts in the GRO.

Example 3. Deletion of ssrA Restores Conjugative Plasmid Propagation and Viral Infection in the GRO Materials and Methods To determine whether deletions of ssrA or arfB could restore propagation of horizontally-transferred genetic elements in the GRO, conjugation efficiency and growth rate from plasmids RK2 and F on GRO strains was assessed with single and double deletions of ssrA, arfA, and arfB. Previous research indicates that the UAG stop codon in the trfA gene on RK2 leads to impaired conjugation efficiency and replication in the GRO (Ma & Isaacs, *Cell Systems* 3:199-207 (2016)), likely because the TrfA protein is required to initiate plasmid replication (Pansegrau et al., *Journal of molecular biology* 239:623-663 (1994)). Phenotypically, this manifests as reduced efficiency of plasmid transfer in conjugation experiments and increased doubling times for RK2+ strains in media selecting for plasmid maintenance due to loss of plasmid and concomitant antibiotic resistance genes.

Results

Figure 4A:
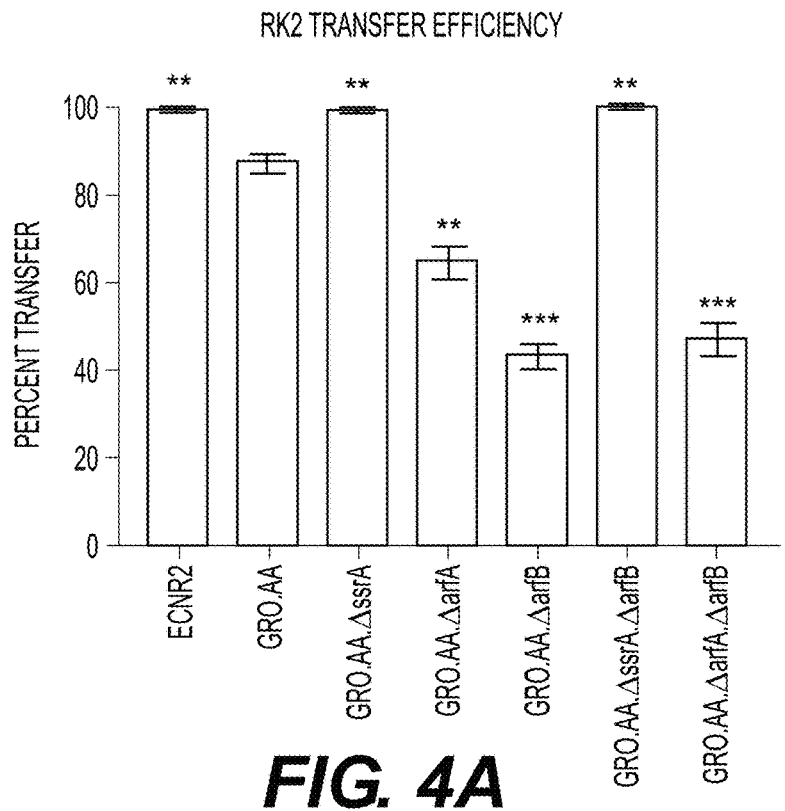
FIGS. 4A-4D are bar graphs and FIGS. 4E and 4F are diagrams showing deleting ssrA restores propagation of both viruses and conjugative plasmids in the genomically recoded organism.
Figure 4B:
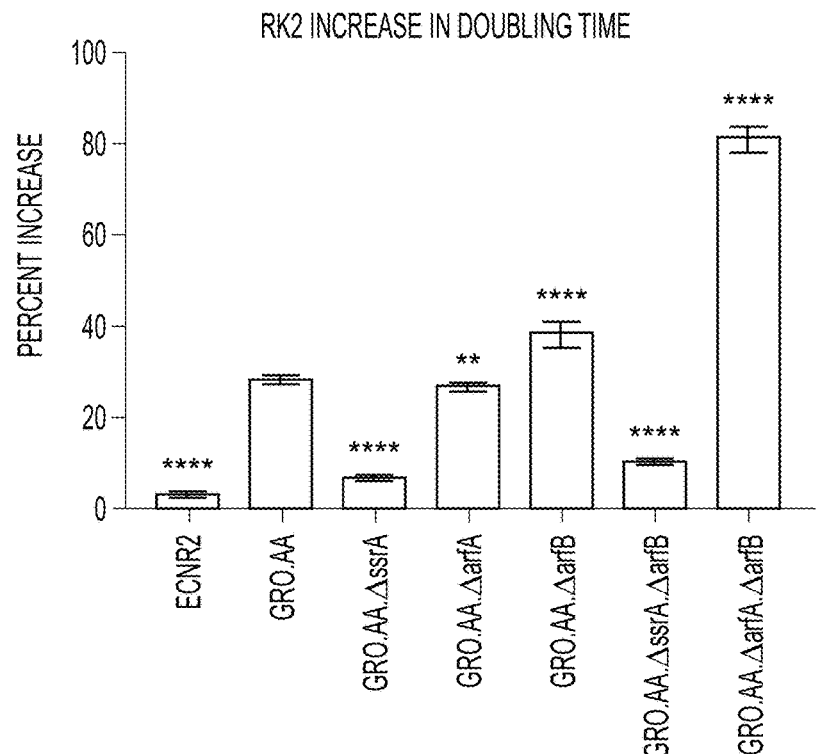
Figure 4C:
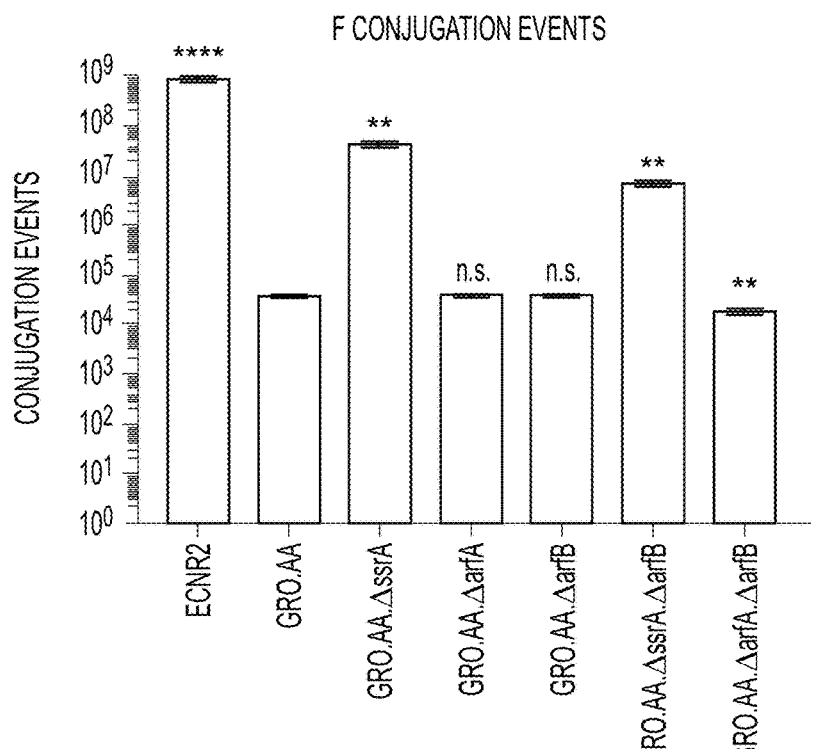

It was found that deletion of ssrA increased the ability of the GRO to both receive (FIG. 4A) and replicate RK2 (FIG. 4B). RK2 conjugation efficiency in GRO.AA.ΔssrA improved to 99% (compared to 87% in GRO.AA), and the strain showed an increase in doubling time of only 6% compared to a 28% increase for GRO.AA (p<0.0001). Similar results were observed for GRO.AA.ΔssrA.ΔarfB. However, single deletion of arfB halved RK2 conjugative efficiency (FIG. 4A, p=0.0002). This strain also exhibited a 38% increase in doubling time when bearing RK2, compared to the 28% increase in doubling time seen in the GRO with no ribosomal rescue gene deletions (FIG. 4B, p<0.0001).

Figure 4D:
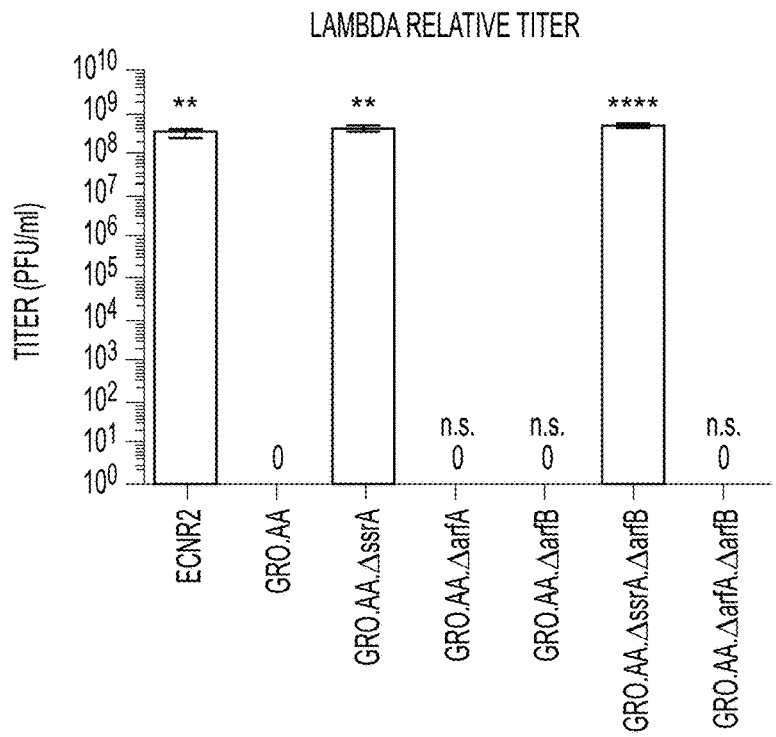
Figures 4E, 4F:
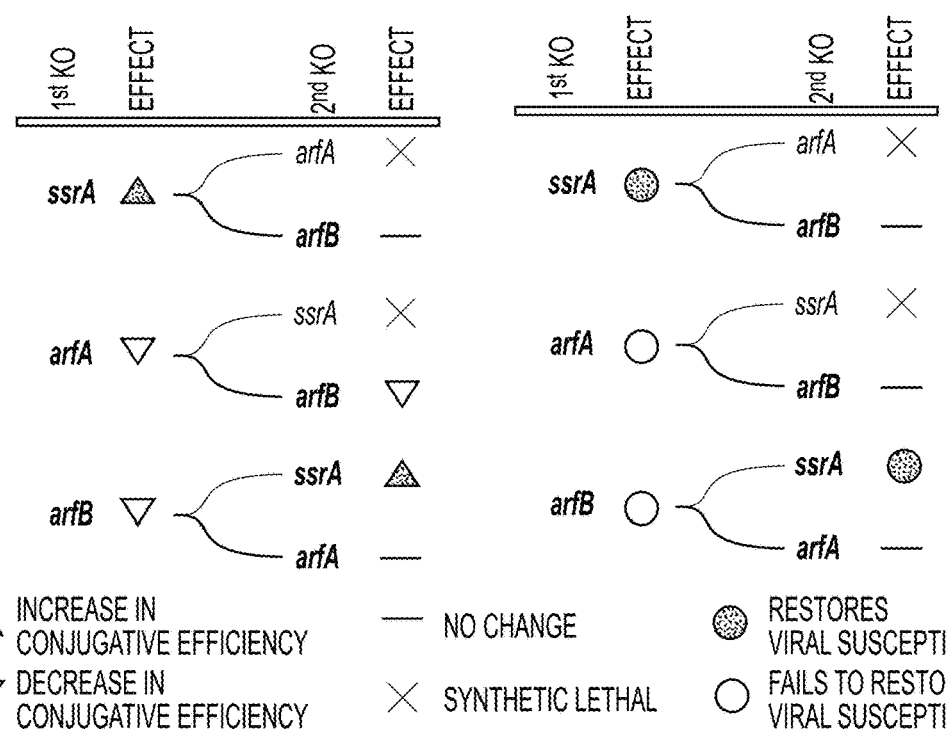

For plasmid F (FIG. 4C), which contains UAG-ending genes traY and traL that are essential for conjugation between cells (Ma & Isaacs, *Cell Systems* 3:199-207 (2016)), it was found that deletion of ssrA increased conjugation events from the GRO donor 1,000-fold to $3.56 \times 10^7$ (p=0.0015) compared to GRO.AA ($3.30 \times 10^4$ events), arfA deletion ($3.41 \times 10^4$ events), and arfB deletion ($3.47 \times 10^4$ events). GRO.AA.ΔssrA.ΔarfB and GRO.AA.ΔarfA.ΔarfB exhibited 5.2- and 2.3-fold decrease in conjugative efficiency when compared to GRO.AA.ΔssrA and GRO.AA.ΔarfA single deletion strains, respectively (p<0.01 for each, FIG. 4C). These reductions in RK2 and F conjugative efficiency attributable to arfB deletion indicate that ArfB likely contributes to relief of nonstop ribosomes when encoded in its native ribosomal context, supporting evidence of ArfB's ribosomal rescue activity previously validated in vitro (Handa et al., *Nucleic Acids Research* 39:1739-1748 (2011)) and when over-expressed in the absence of ssrA and arfA in vivo (Chadani et al., *Molecular Microbiology* 78:796-808 (2010)). However, deletion of ssrA is sufficient to restore both conjugation and propagation of RK2 and F in the GRO. Infection with phage 2 on the suite of deletion strains (FIG. 4D) was conducted. Although deletion of arfA or arfB does not recover viral infection, deletion of the ssrA gene—either alone (p=0.0016) or alongside deletion of arfB (p<0.0001)—recovers 2 infection of the GRO to levels similar to wild-type, with about $10^8$ plaque forming units per mL (PFU/mL) (FIG. 4D). These results showed that removal of ssrA has the greatest influence in restoring conjugative and plasmid transfer efficiency and viral susceptibility in the GRO (FIGS. 4E and 4F).

In this study, a genomically recoded organism (GRO) containing an unassigned UAG codon was used as a model to investigate the molecular mechanisms that obstruct the propagation of HTGEs in organisms with alternative genetic codes. It is demonstrated that unassigned stop codons elicit near-cognate suppression, frameshifting, and the action of ribosomal rescue mechanisms (FIGS. 2A and 2B). tmRNA-mediated ribosomal rescue prompted by the unassigned codon resulted in the degradation of nascent peptides translated from UAG-ending transcripts and obstructed the propagation of HTGEs (FIGS. 3A-3C, FIGS. 4A-4F). Additionally, ssrA deletion strains exhibited both significantly increased UAG-GFP yields (FIG. 3C) and recovered propagation of HTGEs (FIGS. 4A-4F), consistent with evidence that deletion of ssrA removes inhibition of ArfA production and releases nascent peptides from stalled ribosomes without degradation (Chadani et al., *Systems* 86:151-163 (2011), Garza-Sánchez et al., *Molecular Microbiology* 80:1204-1219 (2011), Schaub et al., *Journal of Biological Chemistry* 287:29765-29775 (2012)). The GRO model thus sheds light on the functional significance of previously described regulatory relationships while elucidating the unique mechanistic contributions of different ribosomal rescue systems in resolving translation at unassigned stop codons.

The mass spectrometry data collected from the GRO model demonstrated the striking proclivity for the ribosome to undergo un-programmed frameshifting at unassigned stop codons and represents, the first in vivo study to examine such frameshifting. Prior studies have revealed programmed ribosomal frameshifting from −4 to +50 nucleotides (Atkins et al., *Nucleic Acids Research* 243:gkw530 (2016), Baranov et al., *Nature Reviews Genetics* 16:517-529 (2015), Huang et al., *Science* 239:1005-1012 (1988), Yan et al., *Cell* 160:870-881 (2015)), but these studies focused on frame-shifts programmed into mRNA transcripts through combinations of four mechanisms: (1) use of rare codons to slow translation speed at the skip site, (2) weak base pairing of the P-site tRNA anticodon and mRNA codon, (3) strong base pairing of the P-site tRNA anticodon to the location where the ribosome will re-bind the mRNA, and (4) a region six bases upstream of the re-binding site that mimics a Shine-Dalgarno sequence and offsets the energetic cost of frameshifting (Pech et al., *New York: Springer*. p. 345-362 (2010)). Although the UAG codon in the GFP transcript slows translation, the P-site codon-anticodon pair for the codon immediately upstream of UAG is exact (CAC codon and GUGHis-tRNA anticodon) (Hsu et al., *Journal of Bacteriology* 158:934-942 (1984)) and any frameshift except backward would incur greater mispairing between the P site codon and anticodon. Additionally, no Shine Dalgarno-like sequence (AGGAGG) (Shine & Dalgarno, *PNAS* 71:1342-1346 (1974), Vimberg et al., *BMC Molecular Biology* 8:100 (2007)) exists upstream, indicating that the GFP construct used contains only one of the four elements required for programmed ribosomal frameshifting. From the construct, frameshifts of potentially up to −6 and +19 nucleotides in response to the unassigned UAG codon were observed (FIGS. 2A and 2B). Collectively, this work uncovered a wide variety of frameshifting events that can occur in response to ribosomal stalling in vivo, highlighting the capacity of the ribosome to continue translation despite missing an important translational component.

Mass spectrometry analysis also revealed truncated mistranslation products that possibly represent loss of translational fidelity and termination by RF2 downstream of an initial mistranslation event at the UAG codon, known as post-peptidyl transfer quality control (Petropoulos et al., *Journal of Biological Chemistry* 289:17589-17596 (2014), Zaher & Green, *Nature* 457:161-166 (2009)), a result previously only observed in vitro. Although prior studies decades ago revealed premature truncation products in vivo (Manley, *Journal of Molecular Biology* 125:407-432 (1978)), they lacked the technical capability to determine whether these peptides arose from a single mistranslation event or demonstrated loss of translational fidelity after the ribosome encounters a rare or unassigned codon. The detected mistranslation products here showed repeated mistranslation events that could not have been produced by suppression, ribosomal rescue, or frameshifting, unless the ribosome frameshifted multiple times after resolving stalling at the UAG codon (FIG. 2B). These events may be followed by ribosomal rescue via ArfA or ArfB, spontaneous ribosomal dissociation, or termination via release factor 2, though the technique use here was not capable of distinguishing between these fates. Previous in vitro studies using purified ribosome complexes determined that a mistranslation event destabilized the P-site helix, reducing the ability of the A-site to discriminate between anticodons and resulting in further mistranslation events and rapid termination by RF2 with the assistance of release factor 3 (Zaher & Green, *Nature* 457:161-166 (2009), Zaher & Green, *RNA* 16:1980-1989 (2010)). The researchers predicted that a single mistranslation event would also lead to prematurely truncated peptides with two or three miscoded C-terminal amino acids appended in vivo (Zaher & Green, *Nature* 457:161-166 (2009)). These findings, together with the results from the Examples here, highlight the GRO as a model for elucidating translational fidelity in vivo.

The GRO demonstrates that general ribosomal rescue mechanisms resolve ribosomal stalling at unassigned stop codons. As most sequenced bacterial species contain a homolog of the tmRNA, ArfA, or ArfB ribosomal rescue systems (Hudson et al., *Frontiers in Microbiology* 5:421 (2014), Keiler, *Nature Reviews Microbiology* 13:285-297 (2015)) and eukaryotic cells contain analogous pathways that rescue stalled ribosomes (Graille & Séraphin, *Nature Reviews Molecular Cell Biology* 13:727-735 (2012)), it is believed that translational stalling at unassigned codons can be resolved similarly in these organisms. Accordingly, organisms beyond *E. coli* should tolerate unassigned codons as intermediates toward codon reassignments in genomic recoding, efforts for which are underway in numerous prokaryotic and eukaryotic species (Lau et al., *Nucleic Acids Research* 45:6971-6980 (2017), Napolitano et al., *PNAS* 113:E5588-E5597 (2016), Ostrov et al., *Science* 353:819-822 (2016), Richardson et al., *Science* 355:1040-1044 (2017)). Additional barriers to codon reassignment exist, such as regulatory roles of codons in gene expression (Lajoie et al., *Science* 342:361-363 (2013a)), but the findings here indicate that unassigned codons are tolerable in the absence of specialized translational machinery to address them, both as intermediate steps towards codon reassignment and as permanent parts of the genetic code.

The findings here indicate the use of unassigned codons to engineer organisms with broad resistance to HTGEs and impart genetic isolation, increasing engineered organisms' stability in biotechnology applications. Since tmRNA homologs are found in >99% of all sequenced bacterial genomes (Hudson et al., *Frontiers in Microbiology* 5:421 (2014), Keiler, *Nature Reviews Microbiology* 13:285-297 (2015)), it is believed that other organisms engineered to contain unassigned codons would exhibit immunity to horizontally transferred genetic elements. As researchers pursue further efforts in whole genome recoding (Boeke et al., *Science* 353:126-127 (2016), Lau et al., *Nucleic Acids Research* 45:6971-6980 (2017); Napolitano et al., *PNAS* 113:E5588-E5597 (2016), Ostrov et al., *Science* 353:819-822 (2016), Richardson et al., *Science* 355:1040-1044 (2017)) and engineer organisms for use in open environments, strategies to genetically isolate such organisms from their surrounding environment would be required to ensure robust function, both individually (Moe-Behrens et al., *Frontiers in Microbiology* 4:5 (2013)) and as members of microbial communities (Grosskopf & Soyer, *Current Opinion in Microbiology* 18:72-77 (2014), Hillesland & Stahl, *PNAS* 107:2124-2129 (2010)). Genomically recoded organisms with unassigned codons would possess reduced susceptibility to exploitation by HTGEs, increasing their stability in open environments. Although this work demonstrates that an unassigned stop codon acts as a barrier to HGT, this current barrier can be breached by mutation or deletion of the tmRNA to produce a functional protein. In contrast, it is believed that an organism with an unassigned sense codon would have even greater barriers to HGT, as premature termination at an unassigned sense codon would likely produce a nonfunctional, truncated peptide. It is believed that further genomic recoding to engineer additional unassigned sense and nonsense codons may be a broadly applicable strategy to confer genetic isolation in living systems, facilitating the safe use of engineered organisms in complex open environments.

Example 4: tmRNA Expression Levels can be Used to Tune the Level of HTGE Resistance Usually, DNA passes from parent to offspring, vertically down the generations. In some cases, it can move directly from one organism to another by a process called horizontal gene transfer. In bacteria, this happens when DNA segments pass through a bacterium's cell wall, which can then be picked up by another bacterium. Because the vast majority of organisms share the same genetic code, the bacteria can read this DNA with ease, as it is in the same biological language. Horizontal gene transfer helps bacteria adapt and evolve to their surroundings, letting them swap and share genetic information that could be useful. The process also poses a threat to human health. The DNA that bacteria share can help spread antibiotic resistance. However, some organisms use an alternative genetic code, which obstructs horizontal gene transfer. They cannot read the DNA transmitted to them, because it is in a different 'biological language'. The mechanism of how this language barrier works has been poorly understood until now.

Materials and Methods

A genomically recoded organism (GRO)—an *E. coli* strain possessing an alternative genetic code lacking the UAG codon and release factor 1 (RF1)—was used to study how a cell resolves a mRNA transcript possessing an alternative genetic code (i.e., one or more codons not present in the host cell. RF1 catalyzes the termination of UAG-ending viral transcripts, resulting in the propagation of horizontally transferred genetic elements (HTGEs) such as viruses and conjugative plasmids in GROs. The Examples above show that tmRNA tags and degrades non-stop viral transcripts, enabling viral resistance in GROs that lack RF1. tmRNA and RF1 thus demonstrate opposing effects with regard to the viral susceptibility of GROs.

A GRO that lacks genomic copies of both RF1 and tmRNA (C31.ΔprfA.ΔλRed.ssrA::tolC) was constructed. A plasmid (p15A origin, low-medium copy) that contains copies of ssrA and prfA under orthogonal synthetic, titratable inducible promoters was constructed and introduced into the GRO. ssrA (coding for tmRNA) is under a pLtetO promoter, and its expression is induced with the addition of anhydrotetracycline (aTc) to the growth medium. prfA (coding for RF1) is under a pVanR promoter, and its expression is induced with the addition of vanillic acid (VA). See FIG. 5A.

Results

To assess the robustness of tmRNA expression in conferring viral resistance in GROs, the viral susceptibility of the GRO was assessed under controlled tmRNA and RF1 expression conditions. The GRO harboring the tmRNA and RF1 expression plasmid were challenged with lambda phage infection in the presence of a range of concentrations of both aTc and VA, and plaque forming units (PFUs) resulting from the infection were counted (FIG. 5A). The Phage X genome possesses 73 genes, of which four terminate in UAG, 29 in UAA, and 40 in UGA. In the absence of tmRNA expression ([aTc]=0), the GRO is susceptible to lambda infection, underscoring the need for functional tmRNA to confer resistance to HTGEs in the GRO that lacks UAG termination functionality.

The expression of ssrA enables resistance to lambda phage infection in the absence of RF1 ([VA]=0) and in the presence of low-level RF1 expression ([VA]=1 µM) (FIG. 5B). At moderate levels of RF1 expression ([VA]=4 µM), low-level tmRNA expression ([aTc]=1.9 ng/ml) fails to confer complete resistance to lambda infection, but higher-level expression enables full resistance. At high levels of RF1 expression ([VA]=16 µM), tmRNA is incapable of conferring resistance to infection. These results confirm the existence of a trade-off between tmRNA expression and RF1 abundance, and demonstrate the ability of robustly-expressed tmRNA to confer GRO resistance to HTGEs even in the presence of moderate levels of native UAG codon termination. These results support the conclusion that tmRNA expression levels can be tuned using synthetic promoters to confer optimal levels of HTGE resistance across a wide range of applications.

These findings highlight the value and effectiveness of tmRNA for conferring resistance to HTGEs in the GRO, and establish the conditions necessary for supporting HTGE resistance in any organism with an alternative genetic code (e.g, with any arbitrary codon recoding scheme). Such resistant organisms preferably include (1) at least one open codon that does not occur within the open coding regions of the GRO's genome, (2) the deletion of native cellular genes associated with interpreting the open codon during translation (release factors for stop codons and all codon-specific tRNAs for sense codons), and (3) robust expression of functional tmRNAs. Given that tmRNA systems are highly conserved across bacterial strains, and that tmRNA homologues also exist within eukaryotic organisms, these conditions will likely impart HTGE resistance in a broad range of natural or engineered recoded organisms.

Applications for GROs that obstruct the transfer of HGTs are vast and include:

Establishing strains resistant to viruses for robust biomanufacturing processes immune from viral contamination. Using organisms with alternative genetic codes in industrial settings could increase stability and reduce the risk and cost of biological production (Calendar, et al. *The Bacteriophages*, 2nd ed. (Oxford University Press) (2006)). See also, e.g., Bethencourt, et al., *Nature Biotechnology*, volume 27, page 681(2009) and Barone, et al., *Nature Biotechnology*, volume 38, pages 563-572 (2020).

Endow 'genetic isolation' safeguard to stabilize genetically engineered organisms in open environment exposed to complex microorganisms, viruses and other natural species. Such an organism will not permit expression of exogenous genetic material, establishing genetic isolation.

Engineer communities of recoded organisms having alternative genetic codes fully isolated from environmental insults or HTGEs. Such properties render more robust solutions for diagnostic or therapeutic clinical applications that seek to monitor or perturb human microbiomes or ecological microbiomes (e.g., in the rhizosphere for remediation applications).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A prokaryotic cell comprising: a genome wherein at least one endogenous codon has been eliminated by reassignment of the codon to a synonymous or nonsynonymous codon, and one or more recombinant expression constructs for expression of one or more genes of one or more ribosomal rescue pathways, wherein the prokaryotic cell is a genomically recoded organism (GRO).

2. The cell of claim 1, wherein the gene encoding the cell's endogenous tRNA or tRNAs capable of decoding the eliminated sense codon is mutated or deleted to reduce or eliminate recognition of that codon.

3. The cell of claim 1, wherein the eliminated codon comprises a sense codon.

4. The cell of claim 1, further comprising one or more additional recombinant expression constructs encoding a protein of interest for recombinant protein expression, wherein the additional recombinant expression construct lacks the eliminated codon.

5. The cell of claim 1, wherein the cell's genome further comprises reassignment of a second codon to a synonymous or nonsynonymous codon.

6. The cell of claim 5, wherein the second codon is reassigned to a synonymous codon.

7. The cell of claim 6, wherein the second codon comprises a sense codon.

8. The cell of claim 7, wherein the gene encoding the cell's endogenous tRNA or tRNAs capable of decoding the sense second codon is mutated or deleted to reduce or eliminate recognition of that codon.

9. The cell of claim 5, wherein the second codon is a nonsense codon.

10. The cell of claim 9, wherein the gene encoding the cell's endogenous release factor or factors capable of terminating translation at the nonsense second codon is mutated or deleted to reduce or eliminate recognition of that codon.

11. The cell of claim 1, wherein the prokaryote is a bacterium, optionally wherein the bacterium is an *E. coli* or a Bacilli.

12. The cell of claim 1, wherein the cell is resistant to completed transfer, propagation, expression, and subsequent passage of a horizontally transferred genetic element (HTGE) compared the corresponding cell comprising a genome wherein the eliminated codon has not been eliminated, lacking the one or more recombinant expression constructs, or a combination thereof.

13. A culture system comprising a plurality of the cells of claim 1, wherein the culture system comprises a closed culture system.

14. The cell of claim 1, wherein the eliminated codon is a nonsense codon.

15. The cell of claim 14, wherein the gene encoding the cell's endogenous release factor or factors capable of terminating translation at the eliminated nonsense codon is mutated or deleted to reduce or eliminate recognition of that codon.

16. The cell of claim 1, wherein the gene(s) encode bacterial tmRNA-SmpB, ArfA, ArfB, or a combination thereof, or the corresponding gene or genes of another organism.

17. The cell of claim 16, wherein the gene(s) encode bacterial tmRNA-SmpB or the corresponding gene(s) of another organism.

18. The cell of claim 17, wherein at least one of the genes is ssrA.

19. The cell of claim 1, comprising at least 5 copies of at least one of the genes.

20. The cell of claim 1, wherein the eliminated codon is a nonsense codon, the gene encoding the cell's endogenous release factor or factors capable of terminating translation at the eliminated nonsense codon is mutated or deleted to reduce or eliminate recognition of that codon, and the gene(s) encode bacterial tmRNA-SmpB, optionally in further combination with ArfA and/or ArfB.

* * * * *

SEQUENCE LISTING

```
<160> NUMBER OF SEQ ID NOS: 42

<210> SEQ ID NO 1
<211> LENGTH: 11
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<223> OTHER INFORMATION: X = any amino acid
<220> FEATURE:
<221> NAME/KEY: misc_feature
<222> LOCATION: (9)..(11)
<223> OTHER INFORMATION: Xaa can be any naturally occurring amino acid

<400> SEQUENCE: 1

Leu Glu His His His His His His Xaa Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 2

Leu Glu His His His His His His Gln Gly Ala Arg
1               5                   10

<210> SEQ ID NO 3
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 3

Ala Leu Gly Asp Pro Met Val Arg
1               5
```

<210> SEQ ID NO 4
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 4

Leu Glu His His His His His His Gly Asp Ala Ala Asn Asp Glu Asn
1               5                   10                  15

Tyr Ala Leu Asp Asp
            20

<210> SEQ ID NO 5
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 5

Leu Glu His His His His His His Gln Leu Asp
1               5                   10

<210> SEQ ID NO 6
<211> LENGTH: 19
<212> TYPE: PRT
<213> ORGANISM: Artificial Sequence
<220> FEATURE:
<223> OTHER INFORMATION: synthetic polypeptide

<400> SEQUENCE: 6

Leu Glu His His His His His His Ala Ala Asn Asp Glu Asn Tyr Ala
1               5                   10                  15

Leu Asp Asp

<210> SEQ ID NO 7
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 7

Leu Glu His His His His His His
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic polynucleotide

<400> SEQUENCE: 8

Leu Glu His His His His His His His
1               5

<210> SEQ ID NO 9
<211> LENGTH: 11
<212> TYPE: PRT
<213> ORGANISM: Artificial Sequence
<220> FEATURE:
<223> OTHER INFORMATION: synthetic polypeptide

```
<400> SEQUENCE: 9

Leu Glu His His His His His His Met Val Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 10

Leu Glu His His His His His His His His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 11

Leu Glu His His His His His His Glu Lys Pro
1               5                   10

<210> SEQ ID NO 12
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 12

Leu Glu His His His His His His Gln Gln Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 13

Leu Glu His His His His His His Ser Leu Lys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 14

Leu Glu His His His His His His Tyr Gln Arg
1               5                   10

<210> SEQ ID NO 15
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 15
```

```
Ala Ala Asn Asp Glu Asn Tyr Ala Leu Asp Asp
1               5                   10

<210> SEQ ID NO 16
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 16

Ala Ala Asn Asp Glu Asn Tyr Ala Leu Ala Ala
1               5                   10

<210> SEQ ID NO 17
<211> LENGTH: 105
<212> TYPE: RNA
<213> ORGANISM: Artificial Sequence
<220> FEATURE:
<223> OTHER INFORMATION: synthetic polynucleotide

<400> SEQUENCE: 17
uagggcgcuc ggggauccca ugguacgcgu gcuagaggca ucaaauaaaa cgaaaggcuc      60
agucgaaaga cugggccuuu cguuuuaucu guuguuuguc gguga                    105

<210> SEQ ID NO 18
<211> LENGTH: 41
<212> TYPE: PRT
<213> ORGANISM: Artificial Sequence
<220> FEATURE:
<223> OTHER INFORMATION: synthetic polypeptide

<400> SEQUENCE: 18

Lys Leu Glu His His His His His His Gly Ala Arg Gly Ser His Gly
1               5                   10                  15

Thr Arg Ala Arg Gly Ile Lys Asn Glu Arg Leu Ser Arg Lys Thr Gly
            20                  25                  30

Pro Phe Val Leu Ser Val Val Cys Arg
        35                  40

<210> SEQ ID NO 19
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 19

Leu Glu His His His His His His Tyr Gly Ala Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 20

Gly Ser His Ala Ala Asn Asp Glu Asn Tyr Ala Leu Asp Asp
1               5                   10

<210> SEQ ID NO 21
<211> LENGTH: 15
```

```
<212> TYPE: PRT
<213> ORGANISM: Artificial Sequence
<220> FEATURE:
<223> OTHER INFORMATION: synthetic polypeptide

<400> SEQUENCE: 21

Gly Ser His Gly Ala Ala Asn Asp Glu Asn Tyr Ala Leu Asp Asp
1               5                   10                  15

<210> SEQ ID NO 22
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 22

Gly Ser His Gly Thr Arg
1               5

<210> SEQ ID NO 23
<211> LENGTH: 45
<212> TYPE: PRT
<213> ORGANISM: Artificial Sequence
<220> FEATURE:
<223> OTHER INFORMATION: synthetic polypeptide

<400> SEQUENCE: 23

Lys Leu Glu His His His His His Arg Ala Leu Gly Asp Pro Met
1               5                   10                  15

Val Arg Val Leu Glu Ala Ser Asn Lys Thr Lys Gly Ser Val Glu Arg
            20                  25                  30

Leu Gly Leu Ser Phe Tyr Leu Leu Phe Val Gly Glu Arg
        35                  40                  45

<210> SEQ ID NO 24
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 24

Leu Glu His His His His His His Gln Arg Ala Leu Gly Asp Pro Met
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 25

Val Leu Glu Ala Ser Asn Lys
1               5

<210> SEQ ID NO 26
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 26

Leu Gly Leu Ala Ala Asn Asp Glu Asn Tyr Ala Leu Asp Asp
```

<210> SEQ ID NO 27
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 27

Leu Gly Leu Ser Ala Ala Asn Asp Glu Asn Tyr Ala Leu Asp Asp
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 28

Leu Glu His His His His His His Gly Asp Pro Met Val Arg
1               5                   10

<210> SEQ ID NO 29
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 29

Leu Glu His His His His His His Gly Asp Ala Ala Asp Asn Tyr Ala
1               5                   10                  15

Asp Asp

<210> SEQ ID NO 30
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 30

Lys Leu Glu His His His His His His Gly Arg Ser Gly Ile Pro Trp
1               5                   10                  15

Tyr Ala Cys Arg His Gln Ile Lys Arg Lys Ala Gln Ser Lys Asp Trp
            20                  25                  30

Ala Phe Arg
        35

<210> SEQ ID NO 31
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 31

Leu Glu His His His His His His Asp Gly Ala Ala Asn Asp Glu Asn
1               5                   10                  15

Tyr Ala Leu Asp Asp
            20

```
<210> SEQ ID NO 32
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 32

Ser Gly Ala Ala Asn Asp Glu Asn Tyr Ala Leu Asp Asp
1               5                   10

<210> SEQ ID NO 33
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 33

Leu Glu His His His His His His Ser Gly Ile Pro Trp Tyr Ala Cys
1               5                   10                  15

<210> SEQ ID NO 34
<211> LENGTH: 12
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (10)..(12)
<223> OTHER INFORMATION: X = any amino acid

<400> SEQUENCE: 34

Lys Leu Glu His His His His His His Xaa Xaa Xaa
1               5                   10

<210> SEQ ID NO 35
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 35

His His His His His His
1               5

<210> SEQ ID NO 36
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 36

Ala Ala Asp Glu Asn Tyr Ala Leu Asp Asp
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 37

Leu Glu His His His His His His Gln Arg
```

```
<210> SEQ ID NO 38
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 38

Leu Glu His His His His His His Val Arg Ala Leu Gly Asp Pro Met
1               5                   10                  15

<210> SEQ ID NO 39
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 39

Leu Glu His His His His His His Gln Ala Leu Gly Asp Pro Met Val
1               5                   10                  15

Arg

<210> SEQ ID NO 40
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 40

Leu Glu His His His His His His Leu Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 41

Leu Glu His His His His His His Gly Arg
1               5                   10

<210> SEQ ID NO 42
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 42

Leu Glu His His His His His His Ser Gly Ala Ala Asn Asp Glu Asn
1               5                   10                  15

Tyr Ala Leu Asp Asp
                20
```